US012723262B2

(12) United States Patent
Kohn et al.

(10) Patent No.: US 12,723,262 B2
(45) Date of Patent: Sep. 1, 2026

(54) OPTIMIZED LENTIVIRAL VECTOR COMPROMISING MINIMAL ENHANCER ELEMENTS FOR STEM CELL GENE THERAPY OF HEMOGLOBINOPATHIES

(71) Applicant: The Regents of the University of California, Oakland, CA (US)

(72) Inventors: Donald B. Kohn, Tarzana, CA (US); Roger Paul Hollis, Los Angeles, CA (US); Richard A. Morgan, Santa Monica, CA (US); Aaron Ross Cooper, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1154 days.

(21) Appl. No.: 17/430,260

(22) PCT Filed: Feb. 12, 2020

(86) PCT No.: PCT/US2020/017998
§ 371 (c)(1),
(2) Date: Aug. 11, 2021

(87) PCT Pub. No.: WO2020/168004
PCT Pub. Date: Aug. 20, 2020

(65) Prior Publication Data

US 2022/0136007 A1 May 5, 2022

Related U.S. Application Data

(60) Provisional application No. 62/805,817, filed on Feb. 14, 2019.

(51) Int. Cl.
*C12N 15/86* (2006.01)
*A61P 7/06* (2006.01)
*C07K 14/805* (2006.01)

(52) U.S. Cl.
CPC ................ *C12N 15/86* (2013.01); *A61P 7/06* (2018.01); *C07K 14/805* (2013.01); *C12N 2740/16043* (2013.01)

(58) Field of Classification Search
CPC .............................. C12N 15/86; C12N 15/867
See application file for complete search history.

(56) References Cited

U.S. PATENT DOCUMENTS 11,326,183 B2* 5/2022 Bonner .................. C12N 15/85
2009/0273550 A1 11/2009 Vieri et al.
2009/0274671 A1 11/2009 Sadelain et al.
2017/0157270 A1 6/2017 Kohn et al.
2017/0173185 A1 6/2017 Sadelain et al.
2018/0008725 A1 1/2018 Rivella et al.
2018/0185415 A1 7/2018 Kohn et al.
2018/0223313 A1 8/2018 Uchida et al.

FOREIGN PATENT DOCUMENTS

WO WO-2018106724 A1 6/2018
WO WO-2020056400 A1 3/2020

OTHER PUBLICATIONS

Arnold CD, Gerlach D, Stelzer C, Boryn LM, Rath M, Stark A. Genome-wide quantitative enhancer activity maps identified by STARR-seq. Science. 2013;339:1074-7.
Breda, L., et al., "Therapeutic Hemoglobin Levels After Gene Transfer in B-thalassemia Mice and in Hematopoietic Cells of B-thalassemia and Sickle Cells Disease Patients," PloS one, 2012, vol. 7(3), pp. 1-16.
Chakalova, L., et al., "The Corfu Deltabeta Thalassemia Deletion Disrupts Gamma-globin Gene Silencing and Reveals Post-transcriptional Regulation of Hbf Expression," Blood, vol. 105(5), pp. 2154-2160.
Diao Y, Fang R, Li B, Meng Z, Yu J, Qiu Y, et al. A tiling-deletion-based genetic screen for cis-regulatory element identification in mammalian cells. Nat Methods. 2017;14:629-35.'.
Dickel DE, Zhu Y, Nord AS, Wylie JN, Akiyama JA, Afzal V, et al. Function-based identification of mammalian enhancers using site-specific integration. Nat Methods. 2014; 11:566-71.
Encode Project Consortium. An integrated encyclopedia of DNA elements in the human genome. Nature. 2012;489:57-74.
Extended European search report dated Nov. 10, 2022, in Application No. EP20756227.3.
Fulco CP, Munschauer M, Anyoha R, Munson G, Grossman SR, Perez EM, et al. Systematic mapping of functional enhancer-promoter connections with CRISPR interference. Science. 2016;354:769-73.
Gisselbrecht SS, Barrera LA, Porsch M, Aboukhalil A, Estep 3rd PW, Vedenko A, et al. Highly parallel assays of tissue-specific enhancers in whole *Drosophila* embryos. Nat Methods. 2013; 10:774-80.
Hanawa, H., et al., "Extended beta-globin locus control region elements promote consistent therapeutic expression of a gamma-globin lentiviral vector in murine beta-thalassemia," Blood, 2004, vol. 104(8), pp. 2281-2290.

(Continued)

*Primary Examiner* — Christopher M Babic
*Assistant Examiner* — Jennifer S Spence
(74) *Attorney, Agent, or Firm* — Mark S. Cohen; PEARL COHEN LLP

(57) ABSTRACT

In certain embodiments a lentiviral vector having optimized reduced size LCR with improved enhancer activity is provided. In certain embodiments direct treatment of a subject by direct introduction of the vector(s) described herein is contemplated. The lentiviral compositions may be formulated for delivery by any available route including, but not limited to parenteral (e.g., intravenous), intradermal, subcutaneous, oral (e.g., inhalation), transdermal (topical), transmucosal, rectal, and vaginal.

16 Claims, 11 Drawing Sheets

Specification includes a Sequence Listing.

(56) References Cited

OTHER PUBLICATIONS

Heinz S, Romanoski CE, Benner C, Glass CK. The selection and function of cell type-specific enhancers. Nat Rev Mol Cell Biol. 2015; 16:144-54.
Inoue F, Ahituv N. Decoding enhancers using massively parallel reporter assays. Genomics. 2015;106:159-64.
International Preliminary Report on Patentability dated Aug. 10, 2021 in PCT Application PCT/US2020/017998.
International Search Report and Written Opinion dated Jun. 23, 2020, in PCT Application PCT/US2020/017998.
Kheradpour P, Ernst J, Melnikov A, Rogov P, Wang L, Zhang X, et al. Systematic dissection of regulatory motifs in 2000 predicted human enhancers using a massively parallel reporter assay. Genome Res. 2013;23:800-11.
Kwasnieski JC, Fiore C, Chaudhari HG, Cohen BA. High-throughput functional testing of Encode segmentation predictions. Genome Res. 2014;24:1595-602.
Levasseur, D.N., et al., “Correction of a Mouse Model of Sickle Cell Disease: Lentiviral/antisickling Beta-globin Gene Transduction of Unmobilized, Purified Hematopoietic Stem Cells”, Blood, 2003, vol. 102(13), pp. 4312-4319.
Liu et al. (2017) Functional assessment of human enhancer activities using whole-genome STARR sequencing, Genome Biology, 18, 219 https://doi.org/10.1186/s13059-017-1345-5.
Liu Y, Yu S, Dhiman VK, Brunetti T et al. Functional assessment of human enhancer activities using whole-genome STARR-sequencing. Genome Biol Nov. 20, 2017;18(1):219. PMID: 29151363 [2 Pages] https://www.ncbi.nlm.nih.gov/geo/query/acc.cgi?acc=GSE82204.
May, C., et al., “Therapeutic haemoglobin synthesis in beta-thalassaemic mice expressing lentivirus-encoded human beta-globin,” Nature, 2000, vol. 406(6791), pp. 82-86.
Miccio, A., et al., “In vivo selection of genetically modified erythroblastic progenitors leads to long-term correction of beta-thalassemia,” Proceedings of the National Academy of Sciences of the United States of America, 2008, vol. 105(30), pp. 10547-10552.
Murtha M, Tokcaer-Keskin Z, Tang Z, Strino F, Chen X, Wang Y, et al. FIREWACh: high-throughput functional detection of transcriptional regulatory modules in mammalian cells. Nat Methods. 2014;11:559-65.
Patwardhan RP, Hiatt JB, Witten DM, Kim MJ, Smith RP, May D, et al. Massively parallel functional dissection of mammalian enhancers in vivo. Nat Biotechnol. 2012;30:265-70.
Pawliuk, R., et al., “Correction of sickle cell disease in transgenic mouse models by gene therapy,” Science, 2001, vol. 294(5550), pp. 2368-2371.
Persons, D., et al., “The Degree of Phenotypic Correction of Murine Beta-thalassemia Intermedia Following Lentiviral-mediated Transfer of a Human Gamma-globin Gene is Influenced by Chromosomal Position Effects and Vector Copy Number,” Blood, vol. 101(6), pp. 2175-2183.
Perumbeti, A., et al., A Novel Human Gamma-globin Gene Vector for Genetic Correction of Sickle Cell Anemia in a Humanized Sickle Mouse Model: Critical Determinants for Successful Correction, Blood, 2009, vol. 114(6), pp. 1174-1185.
Pestina, T., et al., “Correction of Murine Sickle Cell Disease Using Gamma-globin Lentiviral Vectors to Mediate High-level Expression of Fetal Hemoglobin,” 2009, vol. 17(2), pp. 245-252.
Platt et al. (1994) N. Engl. J. Med. 330(23): 1639-1644.
Puthenveetil, G., et al., “Successful correction of the human beta-thalassemia major phenotype using a lentiviral vector,” Blood, 2004, vol. 104(12), pp. 3445-3453.
Roadmap Epigenomics Consortium, Kundaje A, Meuleman W, Ernst J, Bilenky M, Yen A, et al. Integrative analysis of 111 reference human epigenomes. Nature. 2015;518:317-30.’\.
Russell, J., et al., “A Post-transcriptional Process Contributes to Efficient Gamma-globin Gene Silencing in Definitive Erythroid Cells,” European Journal of Haematology, 2007, vol. 79(6), pp. 516-525.
Sanjana NE, Wright J, Zheng K, Shalem O, Fontanillas P, Joung J, et al. High-resolution interrogation of functional elements in the noncoding genome. Science. 2016;353:1545-9.
Shlyueva D, Stampfel G, Stark A. Transcriptional enhancers: from properties to genome-wide predictions. Nat Rev Genet. 2014;15:272-86.
Vanhille L, Griffon A, Maqbool MA, Zacarias-Cabeza J, Dao LT, Fernandez N, et al. High-throughput and quantitative assessment of enhancer activity in mammals by CapStarr-seq. Nat Commun. 2015;6:6905.
Voskaridou et al. (2010) Blood, 115(12): 2354-2363.
Yanez-Cuna JO, Kvon EZ, Stark A. Deciphering the transcriptional cis-regulatory code. Trends Genet. 2013;29:11-22.

* cited by examiner

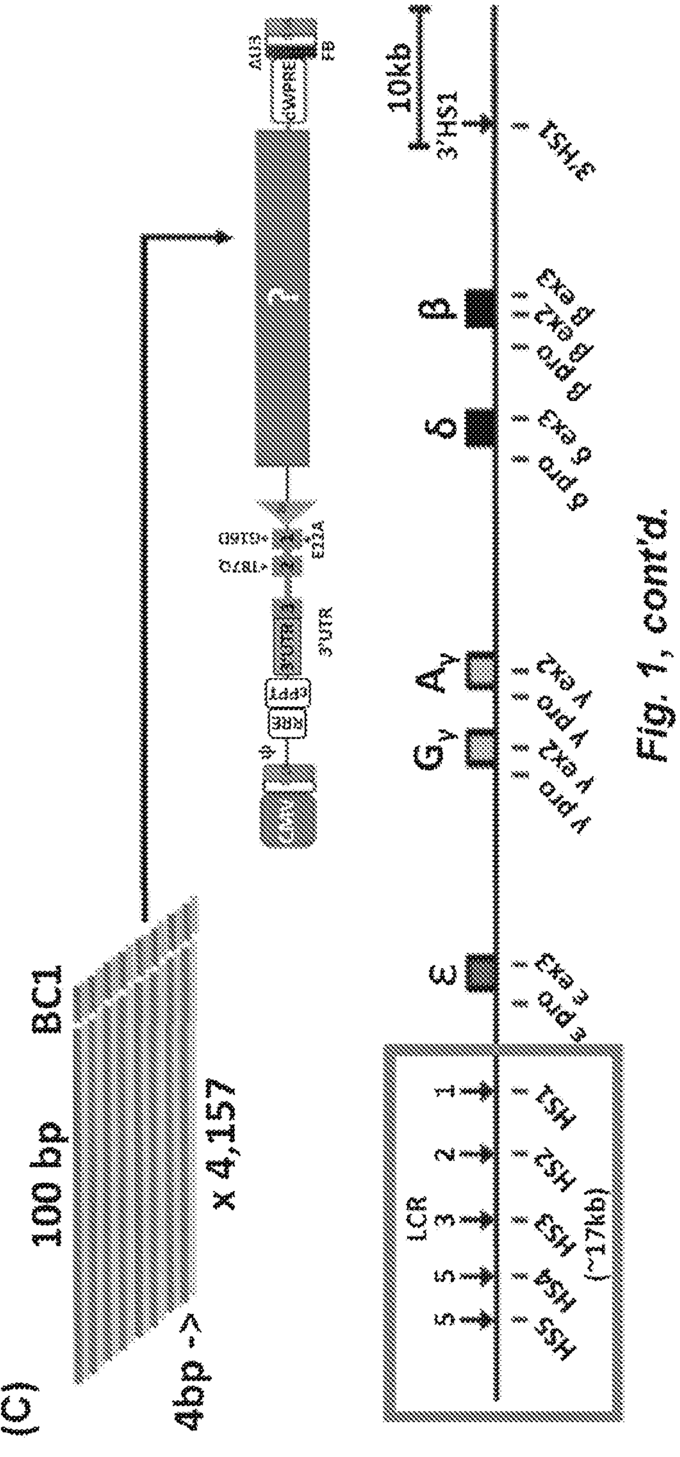
Fig. 1, cont'd.

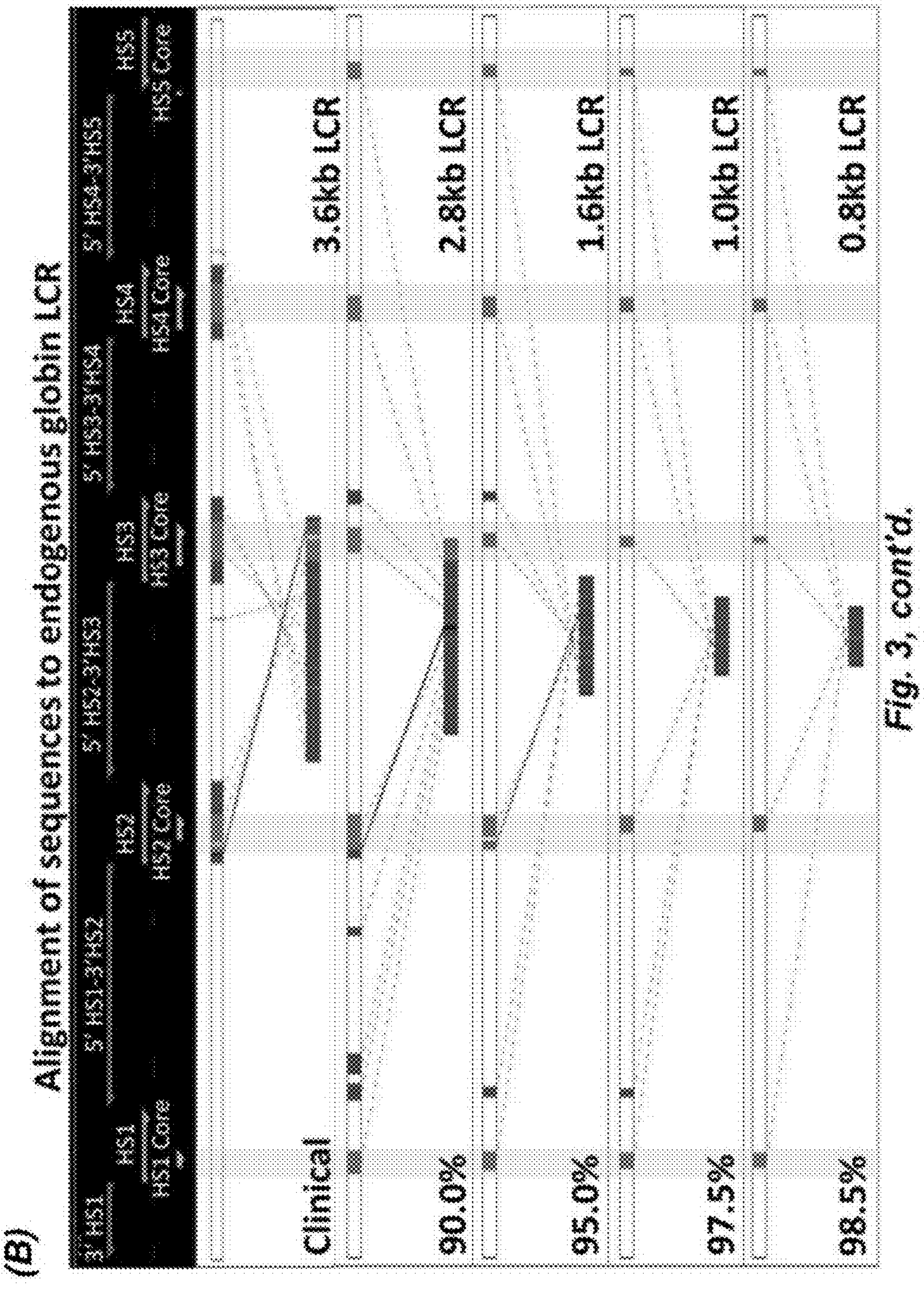
*Fig. 3, cont'd.*

OPTIMIZED LENTIVIRAL VECTOR COMPROMISING MINIMAL ENHANCER ELEMENTS FOR STEM CELL GENE THERAPY OF HEMOGLOBINOPATHIES

CROSS-REFERENCE TO RELATED APPLICATIONS

This application is U.S. 371 National Phase of PCT/US2020/017998, filed on Feb. 12, 2020, which claims benefit of and priority to U.S. Ser. No. 62/805,817, filed on Feb. 14, 2019, both of which is are incorporated herein by reference in their entirety for all purposes.

STATEMENT OF GOVERNMENTAL SUPPORT

[Not Applicable]

INCORPORATION BY REFERENCE OF SEQUENCE LISTING PROVIDED AS A TEXT FILE

A Sequence Listing is provided herewith as a text file, "UCLA-P207P_ST25.txt" created on Feb. 13, 2019 and having a size of 95,997 bytes. The contents of the text file are incorporated by reference herein in their entirety.

BACKGROUND

Sickle cell disease (SCD) is one of the most common monogenic disorders worldwide and is a major cause of morbidity and early mortality (Hoffman et al. (2009) Hematology: Basic Principles and Practice. 5th ed. London, United Kingdom, Churchill Livingstone). SCD affects approximately 80,000 Americans, and causes significant neurologic, pulmonary, and renal injury, as well as severe acute and chronic pain that adversely impacts quality of life. It is estimated that approximately 240,000 children are born annually in Africa with SCD and 80% die by their second birthday. The average lifespan of subjects with SCD in the United States is approximately 40 years and this has remained unchanged over the last 3-4 decades.

SCD is caused by a single amino acid change in β-globin (Glu 6 to Val 6) which leads to hemoglobin polymerization and red blood cell (rbc) sickling. SCD typically results in continual low-grade ischemia and episodic exacerbations or "crises" resulting in tissue ischemia, organ damage, and premature death.

Although SCD is well characterized, there is still no ideal long-term treatment. Current therapies are based on induction of fetal hemoglobin (HbF) to inhibit polymerization of sickle hemoglobin (HbS) (Voskaridou et al. (2010) *Blood,* 115(12): 2354-2363) and cell dehydration (Eaton and Hofrichter (1987) *Blood,* 70(5): 1245-1266) or reduction of the percentage of HbS by transfusions (Stamatoyannopoulos et al., eds. (2001) *Molecular Basis of Blood Diseases.* 3rd ed. Philadelphia, Pennsylvania, USA: WB Saunders). Allogeneic human stem cell transplantation (HSCT) from bone marrow (BM) or umbilical cord blood (UCB) or mobilized peripheral blood stem cells (mPBSC) is a potentially curative therapy, although only a small percentage of patients have undergone this procedure, mostly children with severe symptoms who had HLA-matched sibling donors (Bolaños-Meade and Brodsky (2009) *Curr. Opin. Oncol.* 21(2): 158-161; Rees et al. (2010) *Lancet,* 376(9757): 2018-2031; *Shenoy* (2011) *Hematology Am Soc Hematol Educ Program.* 2011: 273-279).

Transplantation of allogeneic cells carries the risk of graft-versus host disease (GvHD), which can be a cause of extensive morbidity. HSCT using UCB from matched unrelated donors holds reduced risk of acute or chronic GvHD compared with using BM; however, there is a higher probability of engraftment failure using UCB as a result of its lower cell dose and immunologic immaturity (Kamani et al. (2012) *Biol. Blood Marrow Transplant.* 18(8): 1265-1272; Locatelli and Pagliara (2012) *Pediatr. Blood Cancer.* 59(2): 372-376).

Gene therapy with autologous human stem cells (HSCs) is an alternative to allogeneic HSCT, since it avoids the limitations of finding a matched donor and the risks of GvHD and graft rejection. For gene therapy application in SCD patients, one source for autologous HSC would be BM, due to the complications previously described when G-CSF was used to collect autologous peripheral blood stem cells (PBSCs) in SCD patients (Abboud et al. (1998) *Lancet* 351(9107): 959; Adler et al. (2001) *Blood,* 97(10): 3313-3314; Fitzhugh et al. (2009) *Cytotherapy,* 11(4): 464-471). However, more recently, plerixafor, an immunostimulat, can be used to mobilize hematopoietic stem cells into the blood stream. The stem cells can then be extracted from the blood and use. Although general anesthesia imposes a risk for SCD patients as well, current best medical practices can minimize these (Neumayr et al. (1998) *Am. J. Hematol.* 57(2): 101-108).

The development of integrating vectors for β-globin gene transfer has been challenging due to the complex regulatory elements needed for high-level, erythroid-specific expression (Lisowski a& Sadelain (2008) *Br. J. Haematol.* 141(3): 335-345). γ-Retroviral vectors were unable to transfer these β-globin expression cassettes intact (Gelinas et al. (1989) *Adv. Exp. Med. Biol.* 271: 135-148; Gelinas et al. (1989) *Prog. Clin. Biol. Res.* 316B: 235-249). In contrast, lentiviral vectors (LV) can transfer β-globin cassettes intact with relatively high efficiency, although the titers of these vectors are reduced compared with those of vectors bearing simpler cassettes (see, e.g., May et al. (2000) *Nature* 406(6791): 82-86; Pawliuk et al. (2001) *Science,* 294(5550): 2368-2371). In the last decade, many groups have developed different β-globin LV for targeting β-hemoglobinopathies, with successful therapeutic results following transplantation of ex vivo-modified HSC in mouse models (May et al. (2000) *Nature* 406(6791): 82-86; Pawliuk et al. (2001) *Science,* 294(5550): 2368-2371; Levasseur et al. (2003) *Blood,* 102(13):4312-4319; Hanawa et al. (2004) *Blood,* 104(8): 2281-2290; Puthenveetil et al. (2004) *Blood,* 104 (12): 3445-3453; Miccio et al. (2008) *Proc. Natl. Acad. Sci. USA,* 105(30):10547-10552; Pestina et al. (2008) *Mol. Ther.* 17(2): 245-252). Recently, Bluebird Bio, updated trial results with longer follow-up from lentiviral vector treated patients with beta-thalassemia and sickle cell disease. Across three small studies testing the gene therapy in the two blood diseases, patients given LentiGlobin saw their levels of the crucial oxygen-carrying protein hemoglobin rise to approach normal, eliminating the need for blood transfusions in most over the studied period.

Sickle patients with hereditary persistence of fetal hemoglobin (HbF) (HPFH) have improved survival and amelioration of clinical symptoms, with maximal clinical benefits observed when the HbF is elevated above threshold values (e.g., 8%-15% of the total cellular Hb) (Voskaridou et al. (2010) *Blood,* 115(12): 2354-2363; Platt et al. (1994) *N. Engl. J. Med.* 330(23): 1639-1644). Therefore, some gene therapy strategies have employed viral vectors carrying the human γ-globin gene (HBG1/2). However, these constructs expressed HbF poorly in adult erythroid cells, since fetal-specific transcription factors are required for high-level expression of the γ-globin gene (Chakalova et al. (2005) *Blood* 105(5): 2154-2160; Russell (2007) *Eur. J. Haematol.* 79(6): 516-525). These limitations have been overcome by embedding the exons encoding human γ-globin within the human β-globin gene 5' promoter and 3' enhancer elements (Hanawa et al. (2004) *Blood,* 104(8): 2281-2290; Persons et al. (2002) *Blood,* 101(6): 2175-2183; Perumbeti et al. (2009) *Blood,* 114(6): 1174-1185). Breda et al. (2012) *PLoS One,* 7(3): e32345 used an LV vector encoding the human hemoglobin (HBB) gene to increase the expression of normal HbA in $CD34^+$-derived erythroid cells from SCD patients, however, the expression level needed when the HBB gene is used would be higher than would be required for HBG1/2 gene expression to achieve therapeutic benefits in SCD patients.

Another approach is to modify β-globin genes to confer antisickling activity by substituting key amino acids from γ-globin. The modified β-globin cassette should yield the necessary high-level, erythroid-specific expression in adult erythroid cells. Pawliuk et al. (2001) *Science,* 294(5550): 2368-2371 designed an LV carrying a human β-globin gene with the amino acid modification T87Q. The glutamine at position 87 of γ-globin has been implicated in the anti-sickling activity of HbF (Nagel et al. (1979) *Proc. Natl. Acad. Sci., USA,* 76(2): 670-672). This anti-sickling construct corrected SCD in 2 murine models of the disease, and a similar LV has been used in a clinical trial for β-thalassemia and SCD in France (Cavazzana-Calvo et al. (2010) *Nature,* 467(7313): 318-322).

Townes and colleagues have taken a similar approach, developing a recombinant human anti-sickling β-globin gene (HBBAS3) encoding a β-globin protein (HbAS3) that has 3 amino substitutions compared with the original (HbA): T87Q for blocking the lateral contact with the canonical Val 6 of HbS, E22A to disrupt axial contacts (McCune et al. (1994) *Proc. Natl. Acad. Sci. USA,* 91(21): 9852-9856) and G16D, which confers a competitive advantage over sickle-β-globin chains for interaction with the α-globin polypeptide. Functional analysis of the purified HbAS3 protein demonstrated that this recombinant protein had potent activity to inhibit HbS tetramer polymerization (Levasseur et al. (2004) *J. Biol. Chem.* 279(26): 27518-27524.). Levasseur et al. (2003) *Blood,* 102(13): 4312-4319, showed efficient transduction of BM stem cells from a murine model of SCD with a self-inactivating (SIN) LV carrying the HBBAS3 transgene that resulted in normalized rbc physiology and prevented the pathological manifestations of SCD.

Unfortunately, current β-globin expression vectors, suffer from low vector titer and sub-optimal gene transfer to hematopoietic stem cells, representing a major barrier toward the effective implementation of this gene therapy strategy to the clinic.

SUMMARY

Various embodiments contemplated herein may include, but need not be limited to, one or more of the following:

Embodiment 1: A recombinant lentiviral vector (LV) comprising: an expression cassette comprising a nucleic acid construct comprising:

- a human β-globin locus control region comprising a plurality of reduced length hypersensitive site (HS) sequences where the nucleic acid sequence of said reduced length hypersensitive site (HS) sequences consist of one or more sequences independently selected from the group consisting of vector A HS1.1, vector B HS1.1, vector C HS1.1, vector D HS1.1, vector E HS1.1, vector A HS1.2, vector B HS1.2, vector C HS1.2, vector D HS1.2, vector A HS1.3, vector B HS1.3, vector A HS1.4, vector B HS1.4, vector A HS2.1, vector B HS2.1, vector C HS2.1, vector D HS2.1, vector E HS2.1, vector C HS2.2, vector A HS3.1, vector B HS3.1, vector C HS3.1, vector D HS3.1, vector E HS3.1, vector A HS3.2, vector B HS3.2, vector C HS3.2, vector A HS4.1, vector B HS4.1, vector C HS4.1, vector D HS4.1, vector E HS4.1, vector A HS5.1, vector B HS5.1, vector C HS5.1, vector D HS5.1, and vector E HS5.1, or where the reduced length hypersensitive site sequences having at least 90%, or at least 95%, or at least 98%, or at least 99% sequence identify with the nucleotide sequence of the foregoing reduced length hypersensitive site sequences; and
- a heterologous gene to be expressed by said construct operably linked to said human β-globin locus control region; and where said LV is a TAT-independent and self-inactivating (SIN) lentiviral vector.

Embodiment 2: The vector of embodiment 1, wherein the nucleic acid sequence of said reduced length hypersensitive site (HS) sequences consist of sequences independently selected from the group consisting of vector A HS1.1, vector B HS1.1, vector C HS1.1, vector D HS1.1, vector E HS1.1, vector A HS2.1, vector B HS2.1, vector C HS2.1, vector D HS2.1, vector E HS2.1, vector A HS3.1, vector B HS3.1, vector C HS3.1, vector D HS3.1, vector E HS3.1, vector A HS4.1, vector B HS4.1, vector C HS4.1, vector D HS4.1, vector E HS4.1, vector A HS5.1, vector B HS5.1, vector C HS5.1, vector D HS5.1, and vector E HS5.1.

Embodiment 3: The vector according to any one of embodiments 1-2, wherein said β-globin locus control region comprises reduced length hypersensitive site (HS) sequences:

- consisting of or comprising the sequence of one of vector A HS1.1, vector B HS1.1, vector C HS1.1, vector D HS1.1, or vector E HS1.1;
- consisting of or comprising the sequence of one of vector a HS2.1, vector B HS2.1, vector C HS2.1, vector D HS2.1, or vector E HS2.1;
- consisting of or comprising the sequence of one of vector A HS3.1, vector B HS3.1, vector C HS3.1, vector D HS3.1, or vector E HS3.1;
- consisting of or comprising the sequence of one of vector A HS41, vector B HS4.1, vector C HS4.1, vector D HS4.1, or vector E HS4.1; and
- consisting of or comprising the sequence of one of vector A HS5.1, vector B HS5.1, vector C HS5.1, vector D HS5.1, or vector E HS5.1.

Embodiment 4: The vector according to any one of embodiments 1-3, wherein said β-globin locus control region comprises reduced length hypersensitive site (HS) sequence consisting of or comprising the sequence of HS1.1 of vector A.

Embodiment 5: The vector according to any one of embodiments 1-3, wherein said β-globin locus control region comprises reduced length hypersensitive site (HS) sequence consisting of or comprising the sequence of HS1.1 of vector B.

Embodiment 6: The vector according to any one of embodiments 1-3, wherein said β-globin locus control region comprises reduced length hypersensitive site (HS) sequence consisting of or comprising the sequence of HS1.1 of vector C.

Embodiment 7: The vector according to any one of embodiments 1-3, wherein said β-globin locus control region comprises reduced length hypersensitive site (HS) sequence consisting of or comprising the sequence of HS1.1 of vector D.

Embodiment 8: The vector according to any one of embodiments 1-3, wherein said β-globin locus control region comprises reduced length hypersensitive site (HS) sequence consisting of or comprising the sequence of HS1.1 of vector E.

Embodiment 9: The vector according to any one of embodiments 1-8, wherein said β-globin locus control region comprises reduced length hypersensitive site (HS) sequence consisting of or comprising the sequence of HS2.1 of vector A.

Embodiment 10: The vector according to any one of embodiments 1-8, wherein said β-globin locus control region comprises reduced length hypersensitive site (HS) sequence consisting of or comprising the sequence of HS2.1 of vector B.

Embodiment 11: The vector according to any one of embodiments 1-8, wherein said β-globin locus control region comprises reduced length hypersensitive site (HS) sequence consisting of or comprising the sequence of HS2.1 of vector C.

Embodiment 12: The vector according to any one of embodiments 1-8, wherein said β-globin locus control region comprises reduced length hypersensitive site (HS) sequence consisting of or comprising the sequence of HS2.1 of vector D.

Embodiment 13: The vector according to any one of embodiments 1-8, wherein said β-globin locus control region comprises reduced length hypersensitive site (HS) sequence consisting of or comprising the sequence of HS2.1 of vector E.

Embodiment 14: The vector according to any one of embodiments 1-13, wherein said β-globin locus control region comprises reduced length hypersensitive site (HS) sequence consisting of or comprising the sequence of HS3.1 of vector A.

Embodiment 15: The vector according to any one of embodiments 1-13, wherein said β-globin locus control region comprises reduced length hypersensitive site (HS) sequence consisting of or comprising the sequence of HS3.1 of vector B.

Embodiment 16: The vector according to any one of embodiments 1-13, wherein said β-globin locus control region comprises reduced length hypersensitive site (HS) sequence consisting of or comprising the sequence of HS3.1 of vector C.

Embodiment 17: The vector according to any one of embodiments 1-13, wherein said β-globin locus control region comprises reduced length hypersensitive site (HS) sequence consisting of or comprising the sequence of HS3.1 of vector D.

Embodiment 18: The vector according to any one of embodiments 1-13, wherein said β-globin locus control region comprises reduced length hypersensitive site (HS) sequence consisting of or comprising the sequence of HS3.1 of vector E.

Embodiment 19: The vector according to any one of embodiments 1-18, wherein said β-globin locus control region comprises reduced length hypersensitive site (HS) sequence consisting of or comprising the sequence of HS4.1 of vector A.

Embodiment 20: The vector according to any one of embodiments 1-18, wherein said β-globin locus control region comprises reduced length hypersensitive site (HS) sequence consisting of or comprising the sequence of HS4.1 of vector B.

Embodiment 21: The vector according to any one of embodiments 1-18, wherein said β-globin locus control region comprises reduced length hypersensitive site (HS) sequence consisting of or comprising the sequence of HS4.1 of vector C.

Embodiment 22: The vector according to any one of embodiments 1-18, wherein said β-globin locus control region comprises reduced length hypersensitive site (HS) sequence consisting of or comprising the sequence of HS4.1 of vector D.

Embodiment 23: The vector according to any one of embodiments 1-18, wherein said β-globin locus control region comprises reduced length hypersensitive site (HS) sequence consisting of or comprising the sequence of HS4.1 of vector E.

Embodiment 24: The vector according to any one of embodiments 1-23, wherein said β-globin locus control region comprises reduced length hypersensitive site (HS) sequence consisting of or comprising the sequence of HS5.1 of vector A.

Embodiment 25: The vector according to any one of embodiments 1-23, wherein said β-globin locus control region comprises reduced length hypersensitive site (HS) sequence consisting of or comprising the sequence of HS5.1 of vector B.

Embodiment 26: The vector according to any one of embodiments 1-23, wherein said β-globin locus control region comprises reduced length hypersensitive site (HS) sequence consisting of or comprising the sequence of HS5.1 of vector C.

Embodiment 27: The vector according to any one of embodiments 1-23, wherein said β-globin locus control region comprises reduced length hypersensitive site (HS) sequence consisting of or comprising the sequence of HS5.1 of vector D.

Embodiment 28: The vector according to any one of embodiments 1-23, wherein said β-globin locus control region comprises reduced length hypersensitive site (HS) sequence consisting of or comprising the sequence of HS5.1 of vector E.

Embodiment 29: The vector according to any one of embodiments 1-28, wherein said β-globin locus control region comprises reduced length hypersensitive site (HS) sequence consisting of or comprising the sequence of HS1.2 of vector A.

Embodiment 30: The vector according to any one of embodiments 1-28, wherein said β-globin locus control region comprises reduced length hypersensitive site (HS) sequence consisting of or comprising the sequence of HS1.2 of vector B.

Embodiment 31: The vector according to any one of embodiments 1-28, wherein said β-globin locus control region comprises reduced length hypersensitive site (HS) sequence consisting of or comprising the sequence of HS1.2 of vector C.

Embodiment 32: The vector according to any one of embodiments 1-28, wherein said β-globin locus control region comprises reduced length hypersensitive site (HS) sequence consisting of or comprising the sequence of HS1.2 of vector D.

Embodiment 33: The vector according to any one of embodiments 1-32, wherein said β-globin locus control region comprises reduced length hypersensitive site (HS) sequence consisting of or comprising the sequence of HS1.3 of vector A.

Embodiment 34: The vector according to any one of embodiments 1-32, wherein said β-globin locus control region comprises reduced length hypersensitive site (HS) sequence consisting of or comprising the sequence of HS1.3 of vector B.

Embodiment 35: The vector according to any one of embodiments 1-34, wherein said β-globin locus control region comprises reduced length hypersensitive site (HS) sequence consisting of or comprising the sequence of HS1.4 of vector A.

Embodiment 36: The vector according to any one of embodiments 1-34, wherein said β-globin locus control region comprises reduced length hypersensitive site (HS) sequence consisting of or comprising the sequence of HS1.4 of vector B.

Embodiment 37: The vector according to any one of embodiments 1-36, wherein said wherein said β-globin locus control region comprises reduced length hypersensitive site (HS) sequence consisting of or comprising the sequence of HS2.2 of vector C.

Embodiment 38: The vector according to any one of embodiments 1-37, wherein said wherein said β-globin locus control region comprises reduced length hypersensitive site (HS) sequence consisting of or comprising the sequence of HS3.2 of vector A.

Embodiment 39: The vector according to any one of embodiments 1-37, wherein said wherein said β-globin locus control region comprises reduced length hypersensitive site (HS) sequence consisting of or comprising the sequence of HS3.2 of vector B.

Embodiment 40: The vector according to any one of embodiments 1-39, wherein said wherein said β-globin locus control region comprises reduced length hypersensitive site (HS) sequence consisting of or comprising the sequence of HS3.3 of vector C.

Embodiment 41: The vector of embodiment 1, wherein said β-globin locus control region comprises or consists of reduced length hypersensitive site (HS) sequences: vector A HS1.1, vector A HS1.2, vector A HS1.3, vector A HS1.4, vector A HS2.1, vector A HS3.1, vector A HS3.2, vector A HS4.1, and vector A HS5.1.

Embodiment 42: The vector of embodiment 1, wherein said β-globin locus control region comprises or consists of reduced length hypersensitive site (HS) sequences: vector B HS1.1, vector B HS1.2, vector B HS1.3, vector B HS1.4, vector B HS2.1, vector B HS3.1, vector B HS3.2, vector B HS4.1, and vector B HS5.1.

Embodiment 43: The vector of embodiment 1, wherein said β-globin locus control region comprises or consists of reduced length hypersensitive site (HS) sequences: vector C HS1.1, vector C HS1.2, vector C HS2.1, vector C HS2.2, vector C HS3.1, vector C HS3.2, vector C HS4.1, and vector C HS5.1.

Embodiment 44: The vector of embodiment 1, wherein said β-globin locus control region comprises or consists of reduced length hypersensitive site (HS) sequences: vector D HS1.1, vector D HS1.2, vector D HS2.1, vector D HS3.1, vector D HS4.1, and vector D HS51.

Embodiment 45: The vector of embodiment 1, wherein said β-globin locus control region comprises or consists of reduced length hypersensitive site (HS) sequences: vector E HS1.1, vector E HS2.1, vector E HS3.1, vector E HS 4.1, and vector E HS 51.

Embodiment 46: The vector according to any one of embodiments 1-45, wherein the reduced length hypersensitive site (HS) sequences are concatenated in order of increasing HS number: HS1.1 (when present)-HS 1.2 (when present)-HS1.3 (when present)-HS1.4 (when present-HS2 (when present)-HS2.1 (when present)-HS 2.2 (when present)-HS 3.1 (when present)-HS3.2 (when present)-HS4.1 (when present)-HS5.1 (when present).

Embodiment 47: The vector of embodiment 1, wherein said β-globin locus control region comprises or consists of the LCR sequence of vector A.

Embodiment 48: The vector of embodiment 1, wherein said β-globin locus control region comprises or consists of the LCR sequence of vector B.

Embodiment 49: The vector of embodiment 1, wherein said β-globin locus control region comprises or consists of the LCR sequence of vector C.

Embodiment 50: The vector of embodiment 1, wherein said β-globin locus control region comprises or consists of the LCR sequence of vector D.

Embodiment 51: The vector of embodiment 1, wherein said β-globin locus control region comprises or consists of the LCR sequence of vector E.

Embodiment 52: The vector according to any one of embodiments 1-51, wherein said heterologous gene comprises a recombinant human beta globin gene encoding a beta globin polypeptide.

Embodiment 53: The vector of embodiment 52, wherein said human beta globin gene comprises a wild-type beta globin gene.

Embodiment 54: The vector of embodiment 52, wherein said human beta globin gene comprises an anti-sickling human beta globin gene encoding an anti-sickling beta globin polypeptide.

Embodiment 55: The vector of embodiment 54, wherein said anti-sickling human beta globin gene encoding an anti-sickling-beta globin polypeptide comprise one or more mutations selected from the group consisting of Gly16Asp, Glu22Ala and Thr87Gln.

Embodiment 56: The vector of embodiment 55, wherein said beta globin gene comprises the mutation Gly16Asp.

Embodiment 57: The vector according to any one of embodiments 55-56, wherein said beta globin gene comprises the mutation Glu22Ala.

Embodiment 58: The vector according to any one of embodiments 55-57, wherein said beta globin gene comprises the mutation Thr87Gln.

Embodiment 59: The vector of embodiment 55, wherein said anti-sickling human β-globin gene comprises about 2.3 kb of recombinant human β-globin gene including exons and introns under the control of said human β-globin locus control region.

Embodiment 60: The vector according to any one of embodiments 1-59, wherein said β-globin gene comprises β-globin intron 2 with a 375 bp RsaI deletion from IVS2.

Embodiment 61: The vector according to any one of embodiments 1-60, wherein said β-globin gene comprises an SspI (S) to RsaI (R) deletion (~220 bp).

Embodiment 62: The vector according to any one of embodiments 1-61, wherein said vector comprises a human Ankyrin insulator element.

Embodiment 63: The vector according to any one of embodiments 1-62, further comprising an insulator in the 3' LTR.

Embodiment 64: The vector of embodiment 63, wherein said insulator comprises FB (FII/BEAD-A), a 77 bp insulator element, which contains the minimal CTCF binding site enhancer-blocking components of the chicken β-globin 5' DnaseI-hypersensitive site 4 (5' HS4).

Embodiment 65: The vector according to any one of embodiments 1-64, wherein said vector comprises a ψ region vector genome packaging signal.

Embodiment 66: The vector according to any one of embodiments 1-65, wherein the 5' LTR comprises a CMV enhancer/promoter.

Embodiment 67: The vector according to any one of embodiments 1-66, wherein said vector comprises a Rev Responsive Element (RRE).

Embodiment 68: The vector according to any one of embodiments 1-67, wherein said vector comprises a central polypurine tract.

Embodiment 69: The vector according to any one of embodiments 1-68, wherein said vector comprises a post-translational regulatory element.

Embodiment 70: The vector of embodiment 69, wherein the posttranscriptional regulatory element is modified Woodchuck Post-transcriptional Regulatory Element (WPRE).

Embodiment 71: The vector of embodiment 1, wherein said vector comprises the nucleic acid sequence of vector A.

Embodiment 72: The vector of embodiment 1, wherein said vector comprises the nucleic acid sequence of vector B.

Embodiment 73: The vector of embodiment 1, wherein said vector comprises the nucleic acid sequence of vector C.

Embodiment 74: The vector of embodiment 1, wherein said vector comprises the nucleic acid sequence of vector D.

Embodiment 75: The vector of embodiment 1, wherein said vector comprises the nucleic acid sequence of vector E.

Embodiment 76: The vector according to any one of embodiments 1-75, wherein said vector is incapable of reconstituting a wild-type lentivirus through recombination.

Embodiment 77: A host cell transduced with a vector according to any one of embodiments 1-76.

Embodiment 78: The host cell of embodiment 77, wherein the cell is a stem cell.

Embodiment 79: The host cell of embodiment 78, wherein said cell is a stem cell derived from bone marrow, and/or from umbilical cord blood, and/or from peripheral blood.

Embodiment 80: The host cell of embodiment 77, wherein the cell is a 293T cell.

Embodiment 81: The host cell of embodiment 77, wherein, wherein the cell is a human hematopoietic progenitor cell.

Embodiment 82: The host cell of embodiment 81, wherein the human hematopoietic progenitor cell is a $CD34^+$ cell.

Embodiment 83: A method of treating a hemoglobinopathy, in a subject, said method comprising: transducing a stem cell and/or progenitor cell from said subject with a vector according to any one of embodiments 1-76; and transplanting said transduced cell or cells derived therefrom into said subject where said cells or derivatives therefrom express said anti-sickling human beta globin gene.

Embodiment 84: The method of embodiment 83, wherein the cell is a stem cell.

Embodiment 85: The host cell of embodiment 83, wherein said cell is a stem cell derived from bone marrow.

Embodiment 86: The method of embodiment 83, wherein, wherein the cell is a human hematopoietic progenitor cell.

Embodiment 87: The method of embodiment 86, wherein the human hematopoietic progenitor cell is a $CD34^+$ cell.

Embodiment 88: The method according to any one of embodiments 83-87, wherein said hemoglobinopathy is sickle cell disease.

Embodiment 89: The method according to any one of embodiments 83-87, wherein said hemoglobinopathy is β-thalassemia.

Definitions

A "reduced length hypersensitive site (HS) sequence" refers to an HS sequence that is shorter in length than the corresponding wild type HS sequence, e.g., HS2, HS3, and HS4 as previously defined (e.g., HS2 (~1.20 kb), HS3 (~1.28 kb), and HS4 (~1.1 kb)) (see, e.g., Forrester et al. (1986) *Proc. Natl. Acad. Sci. USA,* 83: 1359-1363). In certain embodiments the reduced length HS sequence expressly excludes one or more of the HS core sequence(s) as described in PCT Publication No: WO 2013/071309 (PCT/US2012/064878) which is incorporated herein by reference for the core HS sequences described therein (e.g., core HS2 (~420 bp), core HS3 (~340 bp), and/or core HS4 (~410 bp)).

"Recombinant" is used consistently with its usage in the art to refer to a nucleic acid sequence that comprises portions that do not naturally occur together as part of a single sequence or that have been rearranged relative to a naturally occurring sequence. A recombinant nucleic acid is created by a process that involves the hand of man and/or is generated from a nucleic acid that was created by hand of man (e.g., by one or more cycles of replication, amplification, transcription, etc.). A recombinant virus is one that comprises a recombinant nucleic acid. A recombinant cell is one that comprises a recombinant nucleic acid.

As used herein, the term "recombinant lentiviral vector" or "recombinant LV) refers to an artificially created polynucleotide vector assembled from an LV and a plurality of additional segments as a result of human intervention and manipulation.

By "globin nucleic acid molecule" is meant a nucleic acid molecule that encodes a globin polypeptide. In various embodiments the globin nucleic acid molecule may include regulatory sequences upstream and/or downstream of the coding sequence.

By "globin polypeptide" is meant a protein having at least 85%, or at least 90%, or at least 95%, or at least 98% amino acid sequence identity to a human alpha, beta or gamma globin.

The term "therapeutic functional globin gene" refers to a nucleotide sequence the expression of which leads to a globin that does not produce a hemoglobinopathy phenotype, and which is effective to provide therapeutic benefits to an individual with a defective globin gene. The functional globin gene may encode a wild-type globin appropriate for a mammalian individual to be treated, or it may be a mutant form of globin, preferably one which provides for superior properties, for example superior oxygen transport properties or anti-sickling properties. The functional globin gene includes both exons and introns, as well as globin promoters and splice donors/acceptors.

By "an effective amount" is meant the amount of a required agent or composition comprising the agent to ameliorate or eliminate symptoms of a disease relative to an untreated patient. The effective amount of composition(s) used to practice the methods described herein for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991); and the like.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is typically represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison).

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. In various embodiments "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™. (Version 10; Genetics Computer Group, Inc., Madison, Wis.). "Gap" utilizes the algorithm of Needleman and Wunsch (1970) *J. Mol. Biol.* 48: 443-453, to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (1981) *Adv. Appl. Math.,* 2: 482-489, Smith et al. (1983) *Nucleic Acids Res.* 11: 2205-2220. Useful methods for determining sequence identity are also disclosed in Guide to Huge Computers (Martin J. Bishop, ed., Academic Press, San Diego (1994)), and Carillo et al. (1988) *Appl. Math,* 48: 1073). Certain illustrative computer programs for determining sequence identity include, but are not limited to, the Basic Local Alignment Search Tool (BLAST) programs, that are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., J. Mol. Biol. 215:403-410 (1990)); version 2.0 or higher of BLAST programs allows the introduction of gaps (deletions and insertions) into alignments; for peptide sequence, BLASTX can be used to determine sequence identity; and for polynucleotide sequence, BLASTN can be used to determine sequence identity.

DETAILED DESCRIPTION

It is believed that autologous stem cell gene therapy for sickle cell disease (SCD) or other hemoglobinopathies (e.g., β-thalassemia, etc.) has the potential to treat these illnesses without the need for immune suppression of current allogeneic hematopoietic stem cell transplantation (HSCT) approaches. In particular, it is believed that autologous stem cell gene therapy that introduces, for example, anti-sickling human beta globin into hematopoietic cells (or progenitors thereof) can provide effective therapy for SCD (including, for example, normalized red blood cell (RBC) physiology and prevention of the manifestations of SCD) or certain other hemoglobinopathies.

Current β-globin expression vectors, however, suffer from low vector titer and sub-optimal gene transfer to hematopoietic stem cells, representing a major barrier toward the effective implementation of this gene therapy strategy to the clinic. Without being bound to a particular theory, it is believed that the predominant factor most likely affecting vector performance is overall vector length.

One solution to reducing LCR size has been to use protein binding and histone marking data to redefine boundaries of HS fragments and reduce size. This problem suffers from two defects: 1) This approach may fail to identify enhancer sequences due for example to transient protein binding or histone marking; and 2) This approach may over or under estimate enhancer boundaries as the identified boundaries reflect the footprint of protein bound to DNA during immunoprecipitation.

Figure 1:
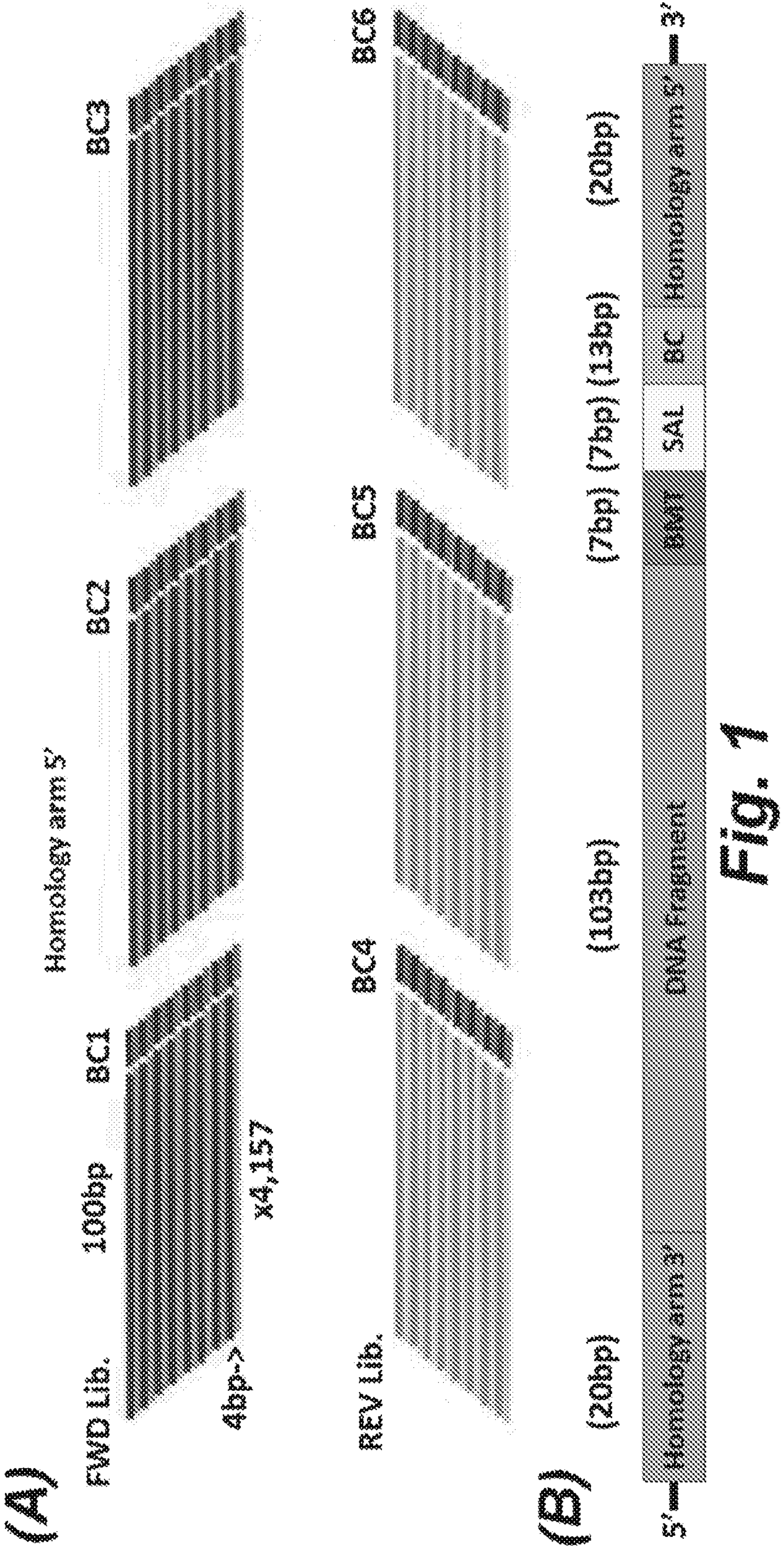
FIG. 1, panels A-C, illustrate the library and oligonucleotide design: Panel A) Each sequence is composed of 100 bp and each subsequent sequence is offset by four nucleotides. The entire library is duplicated three times by assigning three unique barcodes to each sequence. An antisense library is then designed in similar fashion. Panel B) Each oligonucleotide includes 55 bp of "backend" sequence needed for downstream cloning into a lentiviral reporter vector. Cloning results in the placement of the enhancer fragment upstream of the promoter and barcode upstream of the polyadenylation signal. Panel C) Sliding 100 bp window that moves 4 bp at a time across large DNA regions in the context of a lentiviral vector to assay for enhancer activity. Added benefit of selecting for sequences that are successfully packaged and transferred to target cell.

Our solution has been to identify "sequence intrinsic" enhancers (actual DNA sequences that provide enhancer activity) of LCR in the context of a lentiviral vector. As illustrated in FIG. 1, panels A-C, a sliding 100 bp window that moves 4 bp at a time across large DNA regions in the context of a lentiviral vector was used to assay for enhancer activity. This provides the added benefit of selecting for sequences that are successfully packaged and transferred to target cell.

More specifically, we have harnessed the power of massively parallel automated DNA synthesis and next-generation sequencing to map enhancer activity across large DNA regions (~16 kb) in cell types of choice. Our DNA enhancer mapping method can be used to generate novel synthetic enhancers of minimal size to drive tissue specific expression of transgenes. A current limitation to developing tissue-specific enhancers of minimal length is a lack of knowledge regarding the exact boundaries of sequence intrinsic enhancers (the actual DNA sequence that provides enhancer function) in a given cell type. Current technologies such as ChIP-sequencing (ChIP-seq) and its variants, provide vague boundaries of enhancer location based on protein binding and often fail to identify sequence intrinsic enhancers when proteins transiently bind, modify local chromatin structure, and dissociate before they can be fixed in place by DNA-protein crosslinking (a key step in implementing the above-mentioned technologies).

By generating targeted enhancer maps spanning large DNA regions, we can construct streamlined enhancers by concatenating those regions that are (for example) in the 95th, 90th, or 85th percentile of relative enhancer strength. Moreover, this approach is superior to current methods used to identify tissue-specific enhancers as the exact boundaries (+/−4 bp) of enhancer sequences are provided.

We have used this targeted enhancer mapping approach to map sequence intrinsic enhancer function of the endogenous human globin locus region (LCR) in HUDEP2 cells (an erythrocyte-like cell line). The map revealed regions of the LCR unknown to possess enhancer activity and assisted in defining the intrinsic boundaries of the LCR's known enhancer regions. We then set a 95% cutoff based on enhancer strength and concatenated the strongest enhancer sequences to produce a synthetic "mini-LCR" of minimal length (1.6 kb) that possesses sequences from various combinations of the LCR's HS1, HS2, HS3, HS4, HS5, and intervening sequences.

To generate a targeted enhancer map, we started by designing an oligonucleotide that contains base pair positions 1-100 derived from the larger (~16 kb) DNA sequence being interrogated. The subsequent oligonucleotide contained positions 4-104, the next 8-108, and so on until complete coverage of the larger DNA sequence was achieved (total of ~4e3 oligos). The library was duplicated a total of three times by assigning three unique ~13 bp barcodes to each sequence (total of ~1.2e4 oligos) and an antisense library was made doubling the total size of the library (total of ~2.4e4 oligos). Each oligo included ~55 bp of "backend" sequence required for downstream cloning into a lentiviral reporter vector (FIG. 1, panels A-C). Our library construction strategy allowed for placement of the 100 bp "interrogation sequence" upstream of the promoter, and placement of the barcode between the transgene and polyadenylation signal (allowing for expression of the barcode in mRNA).

Figure 2:
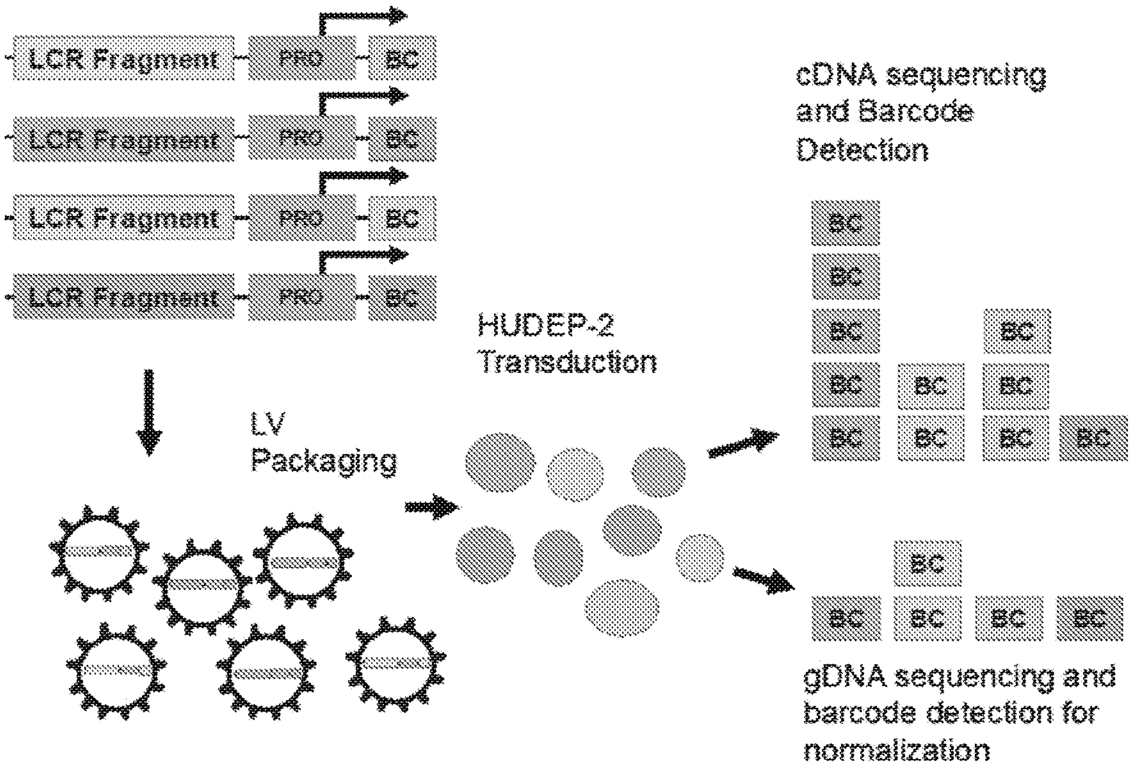
FIG. 2. After microarray oligonucleotide synthesis the plasmid library is assembled, packaged into lentiviral vector particles and transferred to Human Umbilical Derived Cord Blood 2 (HUDEP2:HD2) cells. Cells are harvested for RNA and DNA after culture under erythroid conditions to induce globin expression. gDNA and RNA are extracted, RNA is converted to cDNA, barcodes amplified from plasmid, cDNA and gDNA, and PCR products sequenced. cDNA barcodes are normalized to plasmid or gDNA barcodes to create a normalized map of enhancer activity.
Figure 3:
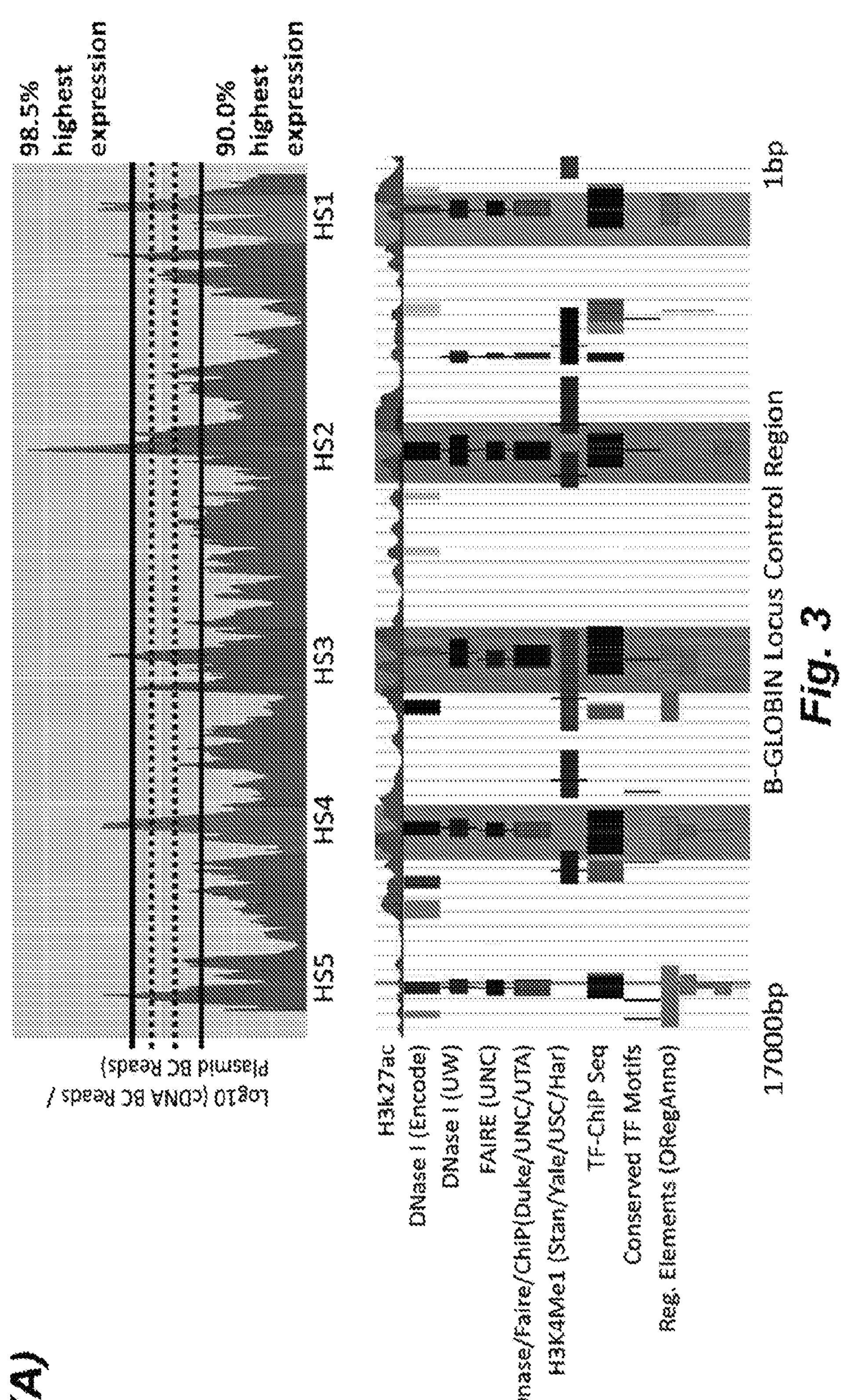
FIG. 3, panels A & B, shows maps of intrinsic enhancer regions across the endogenous glbin LCR. Panel A) Map of sequence intrinsic enhancer regions across the endogenous globin LCR overlaid with other ChhiP_Seq data sets. Panel B) Schema showing different cutoff levels and the lengths of concatenated mini-LCRs produced with alignment of sequence to dendogenous globin LCR.

After microarray oligonucleotide synthesis, the library was assembled and packaged into lentiviral vector particles and transferred to a cell-line of choice. In our example, we used the erythrocyte-like cell line, HUDEP2. Cells were harvested for RNA and DNA after they are partially differentiated down the erythroid lineage. The RNA was then used to make CDNA (using primers specific to the barcode containing reporter gene transcript), barcodes were then amplified from cDNA and gDNA, and PCR products were submitted for next generation sequencing to facilitate the computational quantification and analysis of barcode reads (FIG. 2). The cDNA barcode reads were then normalized to the DNA barcodes reads to generate a high-resolution map of enhancer activity across the large DNA region being interrogated. A 95% cutoff was then set and those regions displaying the strongest enhancer activity were then concatenated to produce a streamlined synthetic enhancer element (FIG. 3).

Figure 4:
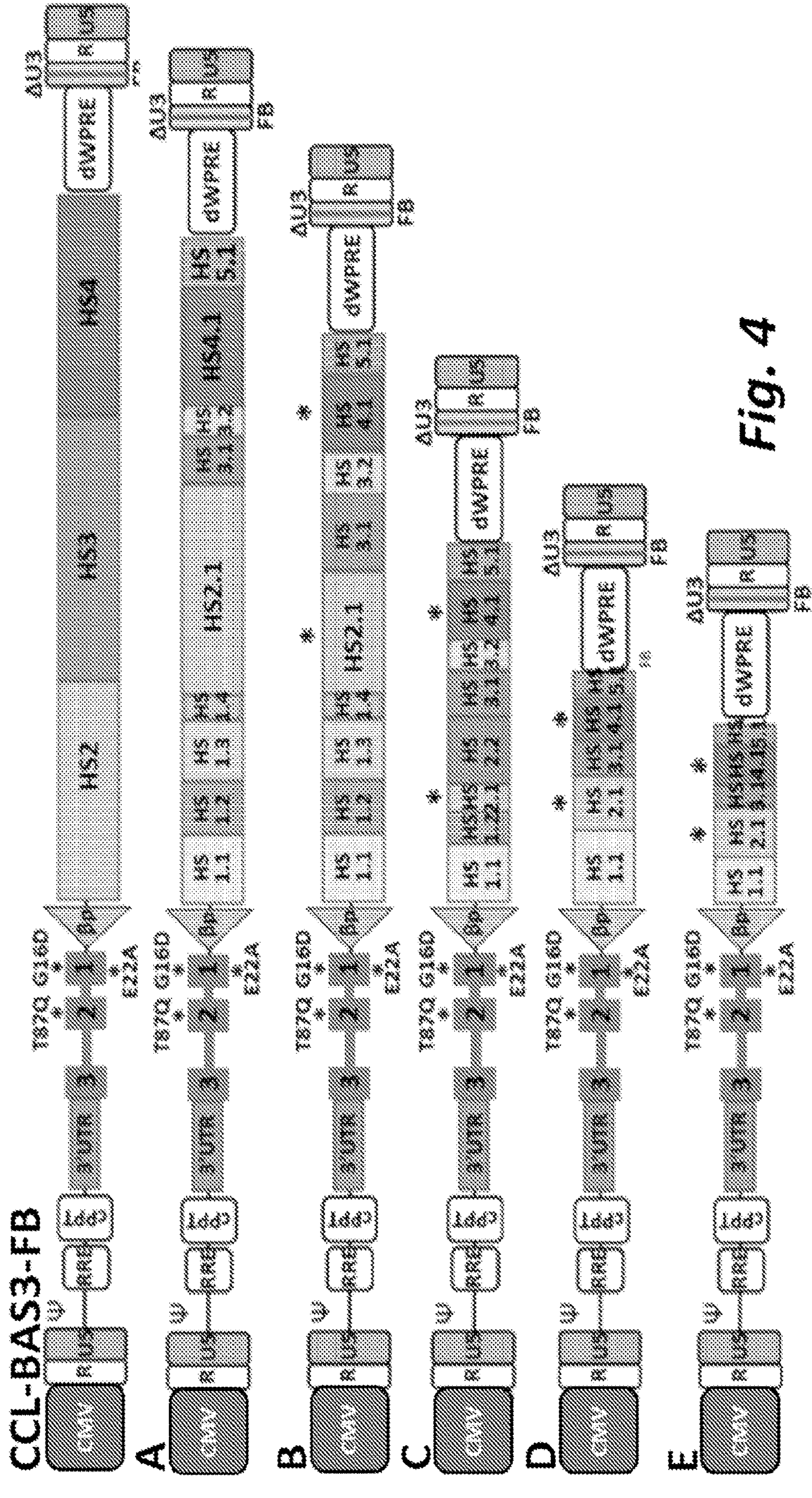
FIG. 4 illustrates the CCL-BASS-FB lentiviral vector along with 4 illustrative reduced length lentiviral vectors (vectors A (80) B (90), C (95), D (97.5), and E ((98.5)).

Our method for generating targeted enhancer maps in a given cell type has facilitated the creation of a synthetic enhancers capable of driving lineage specific expression of a therapeutic transgene. Lentiviral vectors comprising these synthetic enhancers are schematically illustrated in FIG. 4, which illustrates four novel constructs (designated vectors A-D) compared to the CCL-BAS3-FB construct.

Figure 5:
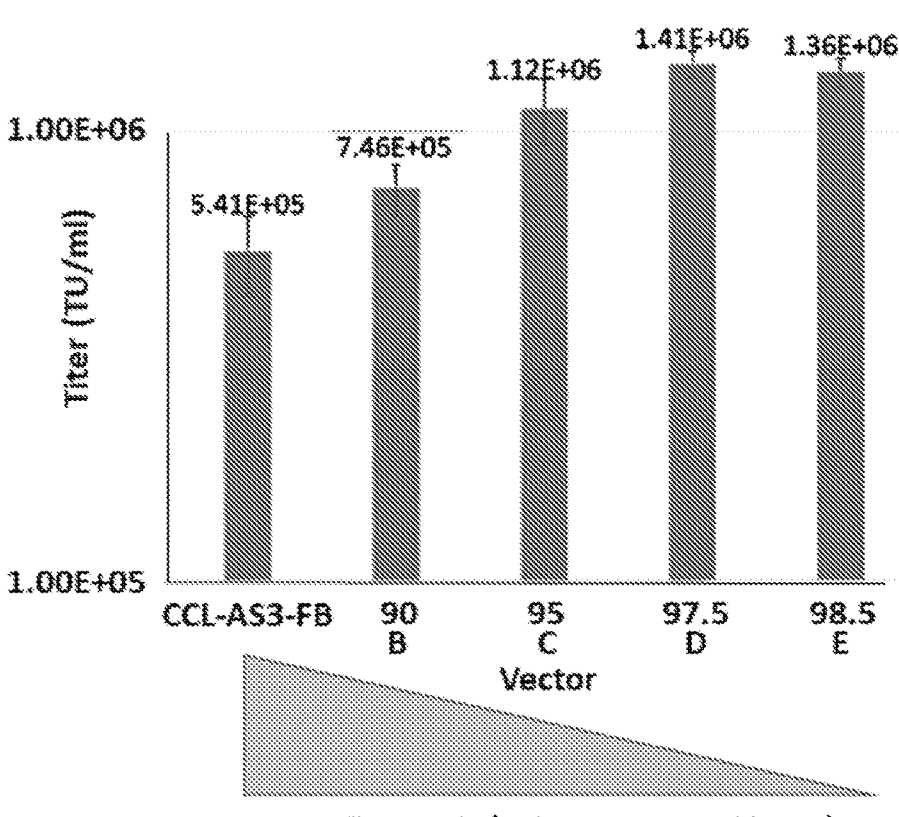
FIG. 5 shows the raw titer produced by vectors B, C, D, and E, compared to the CCL-BAS3-FB.
Figure 6:
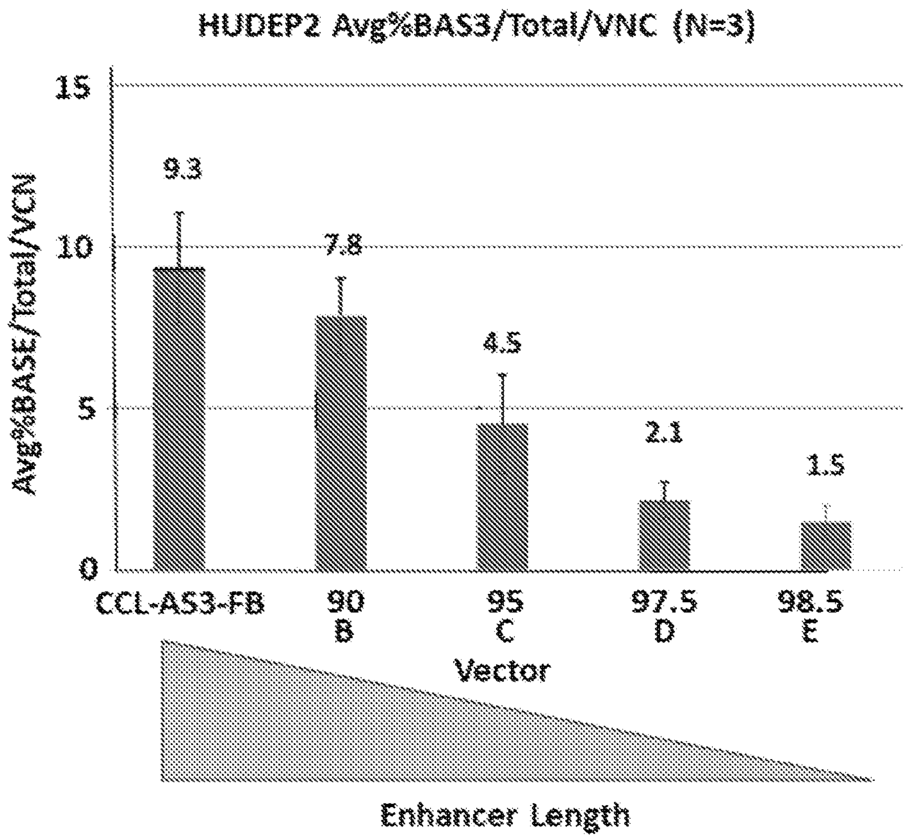
FIG. 6 shows the average % BAS3/total/VCN in HUDEP cells produced by vectors B, C, D, and ED, compared to the CCL-BAS3-FB.
Figure 7:
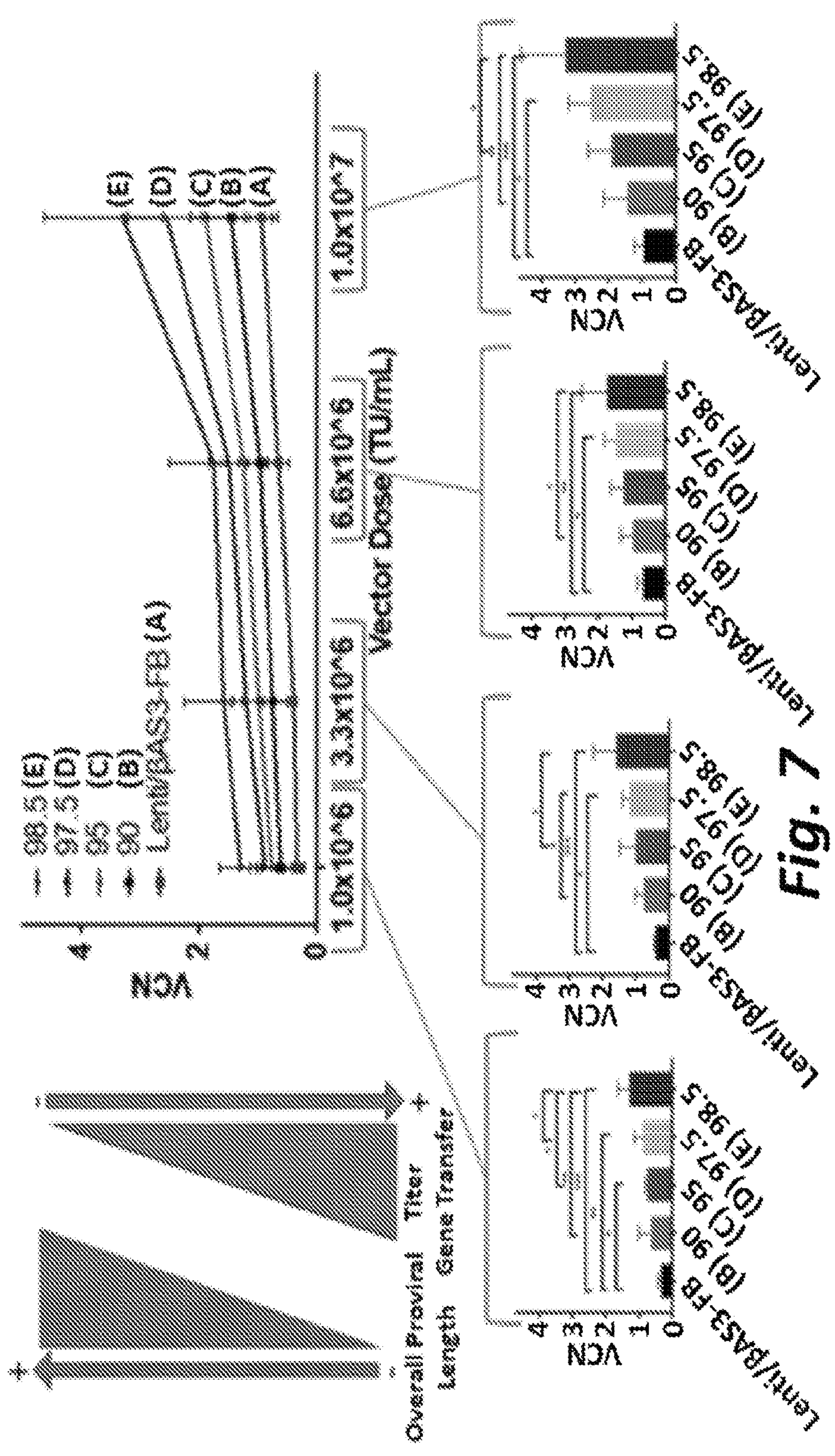
FIG. 7 shows the gene transfer efficiency at various multiplicities of infection (MOI) to CD34+ bone marrow derived HSPCs for vectors A, B, C, and D, compared to the CCL-BAS3-FB.
Figure 8:
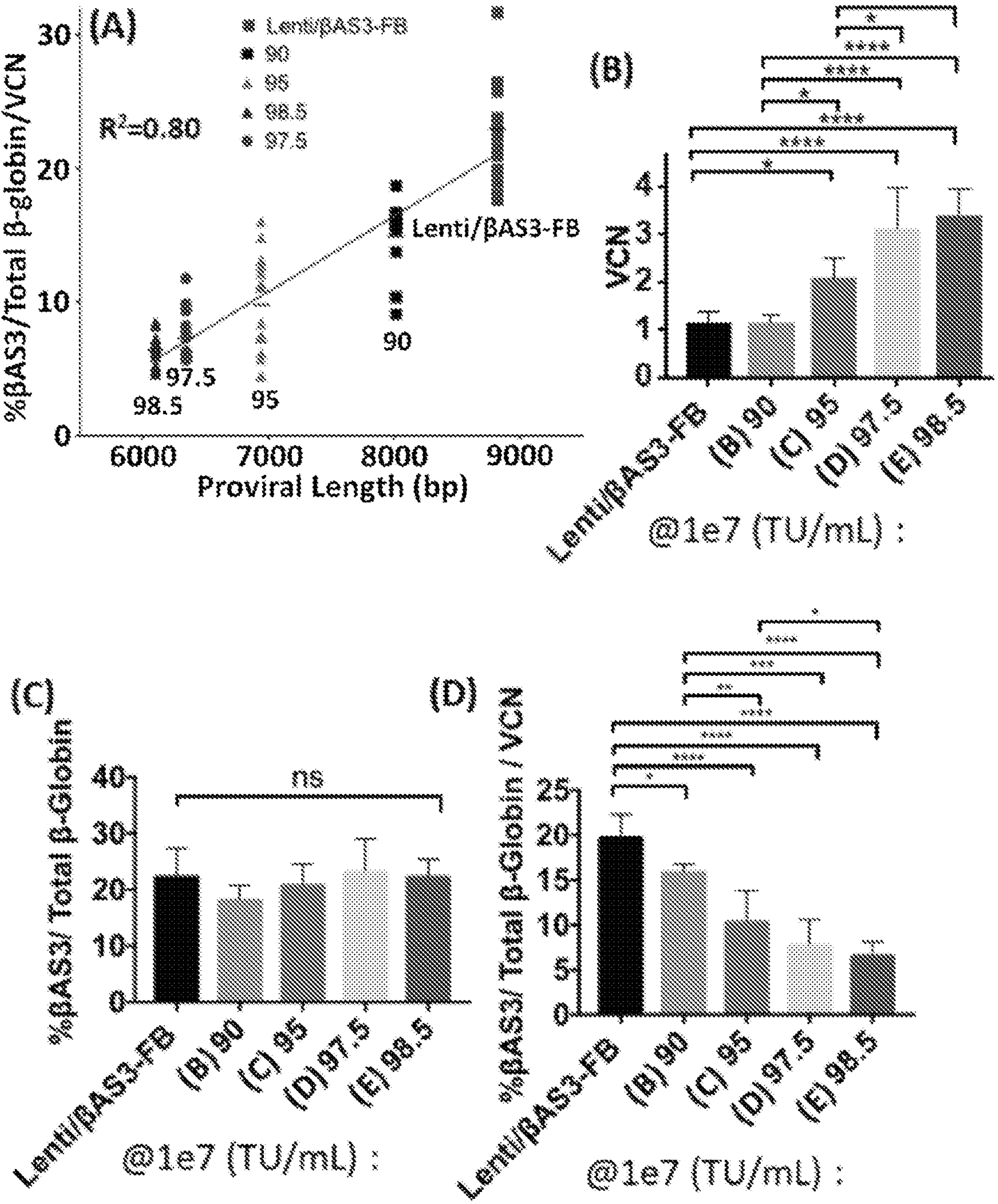
FIG. 8, panel A, shows the average % BAS3/total/VCN vs vector length for vectors B, C, D, and E, compared to the CCL-BAS3-FB when CD34+ HSPCs were transduced at various MOI and cultured under erythroid culture conditions. Panel A demonstrates that enhancer length correlates with % BAS3/total/VCN. Panel B shows the VCNs that were achieved at the $1.0\times10^{7}$ (TU/mL) transduction condition for the experiment shown in panel A. Panel C shows the average % BAS3/Total expression achieved at the $1.0\times10^{7}$ (TU/mL) transduction condition for the experiment shown in panel A. Panel D shows the % BAS3/total/VCN at the $1.0\times10^7$ (TU/mL) transduction condition for the experiment shown in panel A.

FIG. 5 illustrates vector titer produced by each of these constructs and it is noted that vectors A-D all produce a higher titer than CCL-BAS3-FB. As shown in FIG. 6, the average % BAS3/Total/VCN decreased with decreasing enhancer length, indicating that (as expected) as you increase the cut-off of functional DNA sequences to reduce concatenated sequence length you begin to remove some of the sequences required for maximal enhancer function. FIG. 7 illustrates the results of primary cell studies. As shown therein, vector B produced higher vector copy number (VCN) and as a result higher % BAS3/Total than the CCL-AS3-FB construct. However the % BAS3/Total/VCN was lower for vector B than CCL-AS3-FB, which is expected as this vector B does not have all of the strong enhancer sequences present in its concantenated LCR sequence. Similarly, FIG. 8 shows that gene transfer of vector B is linear, resulting in a linear increase of total expression, and that the expression per VCN is predictable unlike the CCL-AS3-FB construct.

Figure 9:
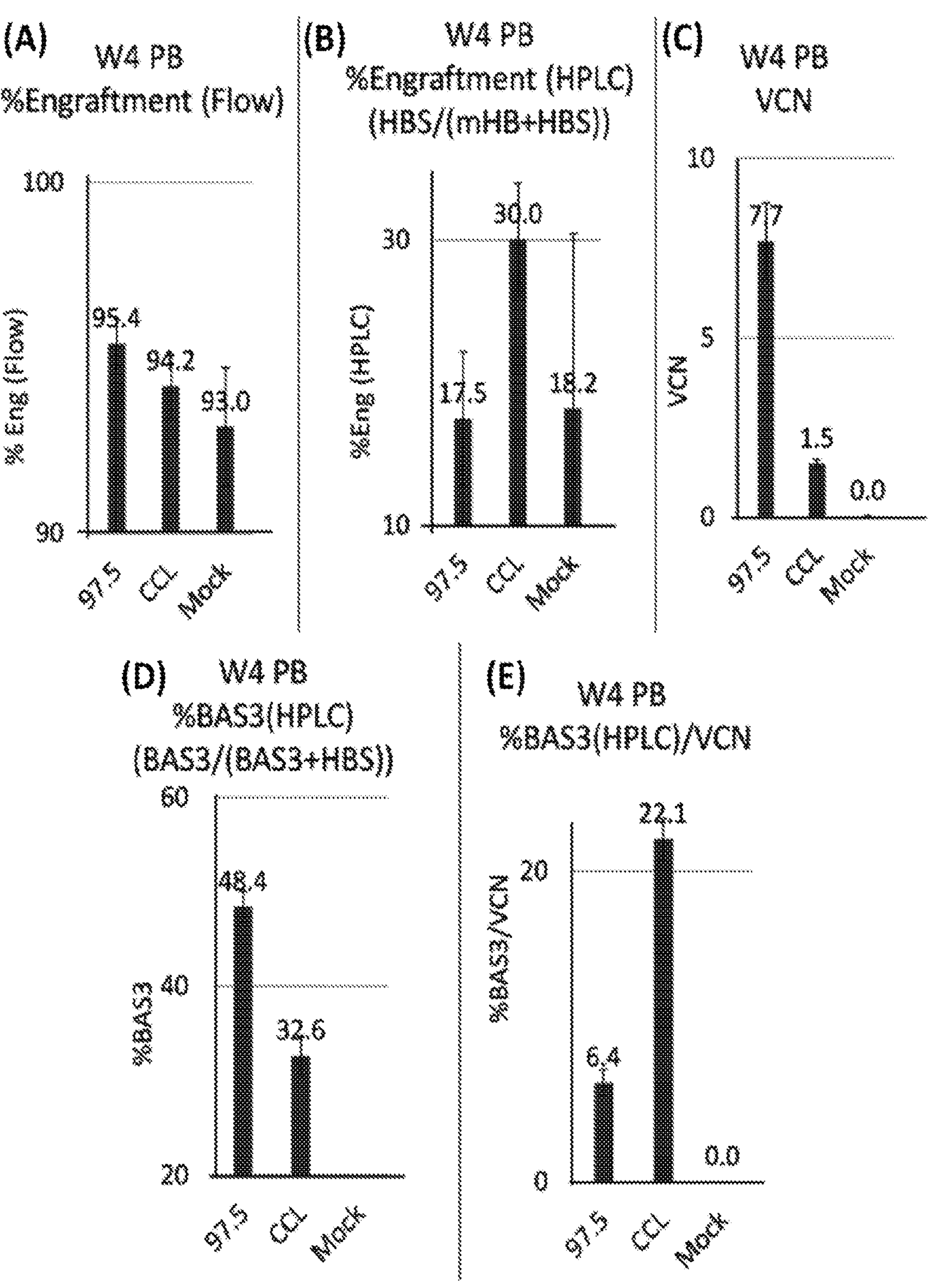
FIG. 9 shows week 4 in vivo data produce after transplanting Lin(~) bone marrow cells derived from SCD mouse model into lethally irradiated recipient mice. Lin(~) bone marrow cells were transduced using vector C (97.5) or CCL-BAS3-FB. Panel A shows % Engraftment of mononuclear cells in peripheral blood, Panel B shows % engraftment of the red blood cell compartment by HPLC, Panel C shows VCNs seen in peripheral blood, Panel D shows % Hb BAS3/Total Hb expression seen in peripheral blood by HPLC, Pandel E shows % HB BAS3/Total Hb normalized to VCN.

FIG. 9 illustrates the results of an in vivo study using transduced Lin(−) bone marrow cells from an SCD mouse model. Cells were transfected with vector C (97.5) and CCL-BASS-FB at equal vector doses demonstrating that the findings from in vitro generated data in primary human cells (FIG. 8) can also be recapitulated in a mouse model of SCD. Vector C displayed superior gene transfer and as a result superior total AS3 expression, however the expression per VCN is reduced as this vector does not contain all of the enhancer sequences that are present in CCL-AS3-FB.

In view of these and other data, we have created reduced size synthetic enhancers capable of driving lineage specific (hematopoietic cell specific) expression of a therapeutic transgene (e.g., a transgene for the treatment of hemoglobinopathies). However, in certain embodiments, the synthetic enhancers can also be redefined sequences, as well as sequences not included or larger than those initially identified.

Accordingly, in certain embodiments, a recombinant lentiviral vector (LV) is provided where the vector comprises a human β-globin locus control region comprising a plurality of reduced length hypersensitive site (HS) sequences where the nucleic acid sequence of the reduced length hypersensitive site (HS) sequences consists of (or comprises) one or more sequences independently selected from the group consisting of vector A HS1.1, vector B HS1.1, vector C HS1.1, vector D HS1.1, vector E HS1.1, vector A HS1.2, vector B HS1.2, vector C HS1.2, vector A HS1.3, vector B HS1.3, vector A HS1.4, vector B HS1.4, vector A HS2.1, vector B HS2.1, vector C HS2.1, vector D HS2.1, vector E HS2.1, vector C HS2.2, vector A HS3.1, vector B HS3.1, vector C HS3.1, vector D HS3.1, vector E HS3.1, vector A HS3.2, vector B HS3.2, vector C HS3.2, vector A HS4.1, vector B HS4.1, vector C HS4.1, vector D HS4.1, vector E HS4.1, vector A HS5.1, vector B HS5.1, vector C HS5.1, vector D HS5.1, and vector E HS5.1 (see, e.g., FIG. 4, and Sequence Listing provided herein), or where the reduced length hypersensitive site sequences having at least 90%, or at least 95%, or at least 98%, or at least 99% sequence identify with the nucleotide sequence of the foregoing reduced length hypersensitive site sequences. In certain embodiments the nucleic acid sequence of said reduced length hypersensitive site (HS) sequences consists of sequences independently selected from the group consisting of vector A HS1.1, vector B HS1.1, vector C HS1.1, vector D HS1.1, vector E HS1.1, vector A HS2.1, vector B HS2.1, vector C HS2.1, vector D HS2.1, vector E HS2.1, vector A HS3.1, vector B HS3.1, vector C HS3.1, vector D HS3.1, vector E HS3.1, vector A HS4.1, vector B HS4.1, vector C HS4.1, vector D HS4.1, vector E HS4.1, vector A HS5.1, vector B HS5.1, vector C HS5.1, vector D HS5.1, and vector E HS5.1.

In certain embodiments the β-globin locus control region comprises (or consists of) reduced length hypersensitive site (HS) sequences:

- consisting of or comprising the sequence of one of vector A HS1.1, vector B HS1.1, vector C HS1.1, vector D HS1.1, or vector E HS1.1;
- consisting of or comprising the sequence of one of vector a HS2.1, vector B HS2.1, vector C HS2.1, vector D HS2.1, or vector E HS2.1;
- consisting of or comprising the sequence of one of vector A HS3.1, vector B HS3.1, vector C HS3.1, vector D HS3.1, or vector E HS3.1;
- consisting of or comprising the sequence of one of vector A HS41, vector B HS4.1, vector C HS4.1, vector D HS4.1, or vector E HS4.1; and
- consisting of or comprising the sequence of one of vector A HS5.1, vector B HS5.1, vector C HS5.1, vector D HS5.1, or vector E HS5.1 (see, e.g., Sequence Listing provided herein).

In certain embodiments the β-globin locus control region comprises reduced length hypersensitive site (HS) sequence consisting of or comprising the sequence of HS1.1 of vector A. In certain embodiments the β-globin locus control region comprises reduced length hypersensitive site (HS) sequence consisting of or comprising the sequence of HS1.1 of vector B. In certain embodiments the β-globin locus control region comprises reduced length hypersensitive site (HS) sequence consisting of or comprising the sequence of HS1.1 of vector C. In certain embodiments the β-globin locus control region comprises reduced length hypersensitive site (HS) sequence consisting of or comprising the sequence of HS1.1 of vector D. In certain embodiments the β-globin locus control region comprises reduced length hypersensitive site (HS) sequence consisting of or comprising the sequence of HS1.1 of vector E.

In certain embodiments the the β-globin locus control region comprises (or further comprises) a reduced length hypersensitive site (HS) sequence consisting of or comprising the sequence of HS2.1 of vector A. In certain embodiments the the β-globin locus control region comprises (or further comprises) a reduced length hypersensitive site (HS) sequence consisting of or comprising the sequence of HS2.1 of vector B. In certain embodiments the the β-globin locus control region comprises (or further comprises) a reduced length hypersensitive site (HS) sequence consisting of or comprising the sequence of HS2.1 of vector C. In certain embodiments the the β-globin locus control region comprises (or further comprises) a reduced length hypersensitive site (HS) sequence consisting of or comprising the sequence of HS2.1 of vector D. In certain embodiments the the β-globin locus control region comprises (or further comprises) a reduced length hypersensitive site (HS) sequence consisting of or comprising the sequence of HS2.1 of vector E.

In certain embodiments the the β-globin locus control region comprises (or further comprises) a reduced length hypersensitive site (HS) sequence consisting of or comprising the sequence of HS3.1 of vector A. In certain embodiments the the β-globin locus control region comprises (or further comprises) a reduced length hypersensitive site (HS) sequence consisting of or comprising the sequence of HS3.1 of vector B. In certain embodiments the the β-globin locus control region comprises (or further comprises) a reduced length hypersensitive site (HS) sequence consisting of or comprising the sequence of HS3.1 of vector C. In certain embodiments the the β-globin locus control region comprises (or further comprises) a reduced length hypersensitive site (HS) sequence consisting of or comprising the sequence of HS3.1 of vector D. In certain embodiments the the β-globin locus control region comprises (or further comprises) a reduced length hypersensitive site (HS) sequence consisting of or comprising the sequence of HS3.1 of vector E.

In certain embodiments the the β-globin locus control region comprises (or further comprises) a reduced length hypersensitive site (HS) sequence consisting of or comprising the sequence of HS4.1 of vector A. In certain embodiments the the β-globin locus control region comprises (or further comprises) a reduced length hypersensitive site (HS) sequence consisting of or comprising the sequence of HS4.1 of vector B. In certain embodiments the the β-globin locus control region comprises (or further comprises) a reduced length hypersensitive site (HS) sequence consisting of or comprising the sequence of HS4.1 of vector C. In certain embodiments the the β-globin locus control region comprises (or further comprises) a reduced length hypersensitive site (HS) sequence consisting of or comprising the sequence of HS4.1 of vector D. In certain embodiments the the β-globin locus control region comprises (or further comprises) a reduced length hypersensitive site (HS) sequence consisting of or comprising the sequence of HS4.1 of vector E.

In certain embodiments the the β-globin locus control region comprises (or further comprises) a reduced length hypersensitive site (HS) sequence consisting of or comprising the sequence of HS5.1 of vector A. In certain embodiments the the β-globin locus control region comprises (or further comprises) a reduced length hypersensitive site (HS) sequence consisting of or comprising the sequence of HS5.1 of vector B. In certain embodiments the the β-globin locus control region comprises (or further comprises) a reduced length hypersensitive site (HS) sequence consisting of or comprising the sequence of HS5.1 of vector C. In certain embodiments the the β-globin locus control region comprises (or further comprises) a reduced length hypersensitive site (HS) sequence consisting of or comprising the sequence of HS5.1 of vector D. In certain embodiments the the β-globin locus control region comprises (or further comprises) a reduced length hypersensitive site (HS) sequence consisting of or comprising the sequence of HS5.1 of vector E.

In certain embodiments the the β-globin locus control region comprises (or further comprises) a In certain embodiments the the β-globin locus control region comprises (or further comprises) a reduced length hypersensitive site (HS) sequence consisting of or comprising the sequence of HS1.2 of vector A. In certain embodiments the the β-globin locus control region comprises (or further comprises) a reduced length hypersensitive site (HS) sequence consisting of or comprising the sequence of HS1.2 of vector B. In certain embodiments the the β-globin locus control region comprises (or further comprises) a reduced length hypersensitive site (HS) sequence consisting of or comprising the sequence of HS1.2 of vector C.

In certain embodiments the the β-globin locus control region comprises (or further comprises) a reduced length hypersensitive site (HS) sequence consisting of or comprising the sequence of HS1.3 of vector A. In certain embodiments the the β-globin locus control region comprises (or further comprises) a reduced length hypersensitive site (HS) sequence consisting of or comprising the sequence of HS1.3 of vector B.

In certain embodiments the the β-globin locus control region comprises (or further comprises) a reduced length hypersensitive site (HS) sequence consisting of or comprising the sequence of HS1.4 of vector A. In certain embodiments the the β-globin locus control region comprises (or further comprises) a reduced length hypersensitive site (HS) sequence consisting of or comprising the sequence of HS1.4 of vector B.

In certain embodiments the the β-globin locus control region comprises (or further comprises) a reduced length hypersensitive site (HS) sequence consisting of or comprising the sequence of HS2.2 of vector C.

In certain embodiments the the β-globin locus control region comprises (or further comprises) a reduced length hypersensitive site (HS) sequence consisting of or comprising the sequence of HS3.2 of vector A. In certain embodiments the the β-globin locus control region comprises (or further comprises) a reduced length hypersensitive site (HS) sequence consisting of or comprising the sequence of HS3.2 of vector B.

In certain embodiments the the β-globin locus control region comprises (or further comprises) a reduced length hypersensitive site (HS) sequence consisting of or comprising the sequence of HS3.3 of vector C.

In certain embodiments the β-globin locus control region comprises or consists of reduced length hypersensitive site (HS) sequences: vector A HS1.1, vector A HS1.2, vector A HS1.3, vector A HS1.4, vector A HS2.1, vector A HS3.1, vector A HS3.2, vector A HS4.1, and vector A HS5.1.

In certain embodiments the β-globin locus control region comprises or consists of reduced length hypersensitive site (HS) sequences: vector B HS1.1, vector B HS1.2, vector B HS1.3, vector B HS1.4, vector B HS2.1, vector B HS3.1, vector B HS3.2, vector B HS4.1, and vector B HS5.1.

In certain embodiments the β-globin locus control region comprises or consists of reduced length hypersensitive site (HS) sequences: vector C HS1.1, vector C HS1.2, vector C HS2.1, vector C HS2.2, vector C HS3.1, vector C HS3.2, vector C HS4.1, and vector C HS5.1.

In certain embodiments the β-globin locus control region comprises or consists of reduced length hypersensitive site (HS) sequences: vector D HS1.1, vector D HS2.1, vector D HS3.1, vector D HS4.1, and vector D HS51.

In certain embodiments the β-globin locus control region comprises or consists of reduced length hypersensitive site (HS) sequences: vector E HS1.1, vector E HS2.1, vector E HS3.1, vector E HS 4.1, and vector E HS 51.

In certain embodiments the reduced length hypersensitive site (HS) sequences are concatenated in order of increasing HS number: HS1.1 (when present)-HS 1.2 (when present)-HS1.3 (when present)-HS1.4 (when present-HS2 (when present)-HS2.1 (when present)-HS 2.2 (when present)-HS 3.1 (when present)-HS3.2 (when present)-HS4.1 (when present)-HS5.1 (when present).

In certain embodiments the β-globin locus control region comprises or consists of the LCR sequence of vector A. In certain embodiments the β-globin locus control region comprises or consists of the LCR sequence of vector B. In certain embodiments the β-globin locus control region comprises or consists of the LCR sequence of vector C. In certain embodiments the β-globin locus control region comprises or consists of the LCR sequence of vector D. In certain embodiments the β-globin locus control region comprises or consists of the LCR sequence of vector E.

In certain embodiments the vector comprises or consists of the nucleic acid sequence of vector A (recognizing that the transgene can be altered, e.g., can be a wild type globin gene, etc.). In certain embodiments the vector comprises or consists of the nucleic acid sequence of vector B (recognizing that the transgene can be altered, e.g., can be a wild type globin gene, etc.). In certain embodiments the vector comprises or consists of the nucleic acid sequence of vector C (recognizing that the transgene can be altered, e.g., can be a wild type globin gene, etc.). In certain embodiments the vector comprises or consists of the nucleic acid sequence of vector D (recognizing that the transgene can be altered, e.g., can be a wild type globin gene, etc.). In certain embodiments the vector comprises or consists of the nucleic acid sequence of vector E (recognizing that the transgene can be altered, e.g., can be a wild type globin gene, etc.).

In view of the foregoing, an improved LV is provided for the introduction of a normal wild-type or an anti-sickling beta globin into stem and progenitor cells (e.g., hematopoietic stem and progenitor cells) that can then be transplanted into a subject in need thereof (e.g., a subject that has the sickle cell mutation, a subject with β-thalassemia, etc.).

In various embodiments the improved vectors described herein are capable of driving lineage-restricted expression of an anti-sickling β-globin like gene (βAS3), a wild-type β-globin gene, or any other heterologous gene it is desired to express. Optimization of the LCR, as described above, with the primary goal of reducing length provides smaller effective vectors with improved enhancer activity.

Additionally, in certain embodiments, elements can be added to the optimized vectors such as the murine GATA1. In certain embodiments a human Ankyrin insulator (~150 bp) element can be included. These vectors, rationally-designed for reduced sizes of the LCR fragments and added transcriptional enhancing elements are believed to be produced at higher titers than the original β-globin lentiviral vector and have improved gene transfer to human HSC while retaining strong erythroid-specific gene expression. Such improved lentiviral vectors can be effective for gene therapy of hemoglobinopathies such as sickle cell disease and β-thalassemia.

In certain embodiments, one or more of the reduced HS sequences described herein can be used in combination with a full-length (e.g., wildtype) HS sequence. Thus, for example, in certain embodiments, a reduced length HS2.1 may be used in combination with a reduced length HS3.1 and/or HS3.2, or with a wildtype HS3, or with a reduced length HS4.1 or a wildtype HS4, or with a reduced length HS3.1 and/or HS3.2 and a wildtype HS4, or with a wildtype HS3 and a reduced length HS4.1. In certain embodiments, a reduced length HS3.1 and/or HS3.2 may be used in combination with a reduced length HS2.1 and/or HS2.2, or with a wildtype HS2, or with a reduced length HS4.1 or a wildtype HS4, or with a reduced length HS2.1 and/or HS2.2 and a wildtype HS4, or with a wildtype HS2 and a reduced length HS4.1. Thus, for example, in certain embodiments, a reduced length HS4.1 may be used in combination with a reduced length HS2.1 and/or HS2.2, or with a wildtype HS2, or with a reduced length HS3.1 and/or HS3.2 or a wildtype HS3, or with a reduced length HS2.1 and/or HS2.2 and a wildtype HS3, or with a wildtype HS2 and a reduced length HS3. In certain embodiments, particularly where a mGATA1q-HS2 and/or human ankyrin insulator element is present, the hypersensitive sites can comprise or consist of a wildtype HS3 and a wildtype HS2. The foregoing combinations of reduce enhancer regions are illustrative and non-limiting. Thus, for example, any of the fragments described herein can either be reduced or redefined (i.e., of a similar size to the original but consisting of a non contigious concatenated sequence). Using the teaching provided herein, numerous other reduced LCR regions are available to one of skill in the art.

In certain embodiments the human β-globin gene in the vectors contemplated herein comprises an anti-sickling human β-globin gene encoding an anti-sickling β-globin polypeptide. In certain embodiments the anti-sickling version of a human β-globin gene used in the vector comprises one, two, or three mutations selected from the group consisting of Gly16Asp, Glu22Ala and Thr87Gln (see, e.g., Levasseur (2004) *J. Biol. Chem.* 279(26): 27518-27524). Without being bound to a particular theory, it is believed the Glu22Ala mutation increases affinity to α-chain, the Thr87Gln mutation blocks lateral contact with Val6 of βS protein, and the Gly16Asp mutation decreases axial contact between globin chains.

In certain embodiments the vectors described herein comprise a human Ankyrin insulator element In certain embodiments the vectors described herein comprise a murine GATA1-HS2.

In various embodiments, the LVs described herein can have additional safety features that can include, for example, the presence of an insulator (e.g., an FB insulator in the 3'LTR). Additionally, or alternatively, in certain embodiments, the HIV LTR has been substituted with an alternative promoter (e.g., a CMV) to yield a higher titer vector without the inclusion of the HIV TAT protein during packaging. Other strong promoters (e.g., RSV, and the like can also be used).

In certain embodiments the vectors contemplated herein include the various elements shown in the vectors (vectors A, B, C, D, or E) illustrated in FIG. 4.

As shown above, the vectors described herein are effective to transduce cells at high titer and to also provide high levels of expression.

In view of these results, it is believed that LVs described herein, e.g., recombinant TAT-independent, SIN LVs that express a human beta-globin gene can be used to effectively treat hemoglobinopathies in subjects (e.g., human and non-human mammals). Such hemoglobinopathies include, but are not limited to sickle cell disease (SCD) and β-thalassemia. It is believed these vectors can be used for the modification of stem cells (e.g., hematopoietic stem and progenitor cells) that can be introduced into a subject in need thereof for the treatment of, e.g., SCD or β-thalassemia. Moreover, it appears that the resulting cells will produce enough of the transgenic β-globin protein to demonstrate significant improvement in subject health. It is also believed the vectors can be directly administered to a subject to achieve in vivo transduction of the target (e.g., hematopoietic stem or progenitor cells) and thereby also effect a treatment of subjects in need thereof.

As noted above, in various embodiments the LVs described herein can comprise various safety features. For example, the HIV LTR has been substituted with a CMV promoter to yield higher titer vector without the inclusion of the HIV TAT protein during packaging. In certain embodiments an insulator (e.g., the FB insulator) is introduced into the 3'LTR for safety. The LVs are also constructed to provide efficient transduction and high titer.

It will be appreciated that the foregoing elements are illustrative and need not be limiting. In view of the teachings provided herein, suitable substitutions for these elements will be recognized by one of skill in the art and are contemplated within the scope of the teachings provided herein.

Anti-sickling β-globin gene and expression cassette.

As indicated above, in various embodiments the LV described herein comprise an expression cassette encoding a wild-type β-globin gene, or an anti-sickling human β-globin gene. On illustrative, but non-limiting cassette is βAS3 which comprises an ~2.3 kb recombinant human β-globin gene (exons and introns) with three amino acid substitutions (Thr87Gln; Gly16Asp; and Glu22A1a) under the control of transcriptional control elements (e.g., the human β-globin gene 5' promoter (e.g., ~266 bp), the human β-globin 3' enhancer (e.g., ~260 by), β-globin intron 2 with a ~375 bp RsaI deletion from IVS2, and a ~3.4 kb composite human β-globin locus control region (e.g., HS2 ~1203 bp; HS3 ~1213 bp; HS4 ~954 bp). One embodiment of a βAS3 cassette is described by Levasseur (2003) *Blood* 102: 4312-4319.

In certain embodiments the β-globin gene comprises a SspI (S) to RsaI (R) deletion (~220 bp), e.g., as described by Antoniou et al. 1998) *Nucl. Acids Res.,* 26(3): 721-729.

The βAS3 cassette, however, is illustrative and need not be limiting. Using the teaching provided herein, numerous variations will be available to one of skill in the art. Such variations include, for example, use of a gene encoding a wild-type β-globin, use of a gene comprising one or two mutations selected from the group consisting of Thr87Gln, Gly16Asp, and Glu22Ala, and/or further or alternative mutations to the β-globin to further enhance non-sickling properties, alterations in the transcriptional control elements (e.g., promoter and/or enhancer), variations on the intron size/structure, and the like.

TAT-Independent and Self Inactivating Lentiviral Vectors.

To further improve safety, in various embodiments, the lentiviral vectors described herein comprise a TAT-independent, self-inactivating (SIN) configuration. Thus, in various embodiments it is desirable to employ in the LVs described herein an LTR region that has reduced promoter activity relative to wild-type LTR. Such constructs can be provided that are effectively "self-inactivating" (SIN) which provides a biosafety feature. SIN vectors are ones in which the production of full-length vector RNA in transduced cells is greatly reduced or abolished altogether. This feature minimizes the risk that replication-competent recombinants (RCRs) will emerge. Furthermore, it reduces the risk that that cellular coding sequences located adjacent to the vector integration site will be aberrantly expressed.

Furthermore, a SIN design reduces the possibility of interference between the LTR and the promoter that is driving the expression of the transgene. SIN LVs can often permit full activity of the internal promoter.

The SIN design increases the biosafety of the LVs. The majority of the HIV LTR is comprised of the U3 sequences. The U3 region contains the enhancer and promoter elements that modulate basal and induced expression of the HIV genome in infected cells and in response to cell activation. Several of these promoter elements are essential for viral replication. Some of the enhancer elements are highly conserved among viral isolates and have been implicated as critical virulence factors in viral pathogenesis. The enhancer elements may act to influence replication rates in the different cellular target of the virus As viral transcription starts at the 3' end of the U3 region of the 5' LTR, those sequences are not part of the viral mRNA and a copy thereof from the 3' LTR acts as template for the generation of both LTR's in the integrated provirus. If the 3' copy of the U3 region is altered in a retroviral vector construct, the vector RNA is still produced from the intact 5' LTR in producer cells, but cannot be regenerated in target cells. Transduction of such a vector results in the inactivation of both LTR's in the progeny virus. Thus, the retrovirus is self-inactivating (SIN) and those vectors are known as SIN transfer vectors.

In certain embodiments self-inactivation is achieved through the introduction of a deletion in the U3 region of the 3' LTR of the vector DNA, i.e., the DNA used to produce the vector RNA. During RT, this deletion is transferred to the 5' LTR of the proviral DNA. Typically, it is desirable to eliminate enough of the U3 sequence to greatly diminish or abolish altogether the transcriptional activity of the LTR, thereby greatly diminishing or abolishing the production of full-length vector RNA in transduced cells. However, it is generally desirable to retain those elements of the LTR that are involved in polyadenylation of the viral RNA, a function typically spread out over U3, R and U5. Accordingly, in certain embodiments, it is desirable to eliminate as many of the transcriptionally important motifs from the LTR as possible while sparing the polyadenylation determinants.

The SIN design is described in detail in Zufferey et al. (1998) *J Virol.* 72(12): 9873-9880, and in U.S. Pat. No. 5,994,136. As described therein, there are, however, limits to the extent of the deletion at the 3' LTR. First, the 5' end of the U3 region serves another essential function in vector transfer, being required for integration (terminal dinucleotide+att sequence). Thus, the terminal dinucleotide and the att sequence may represent the 5' boundary of the U3 sequences which can be deleted. In addition, some loosely defined regions may influence the activity of the downstream polyadenylation site in the R region. Excessive deletion of U3 sequence from the 3'LTR may decrease polyadenylation of vector transcripts with adverse consequences both on the titer of the vector in producer cells and the transgene expression in target cells.

Additional SIN designs are described in U.S. Patent Publication No: 2003/0039636. As described therein, in certain embodiments, the lentiviral sequences removed from the LTRs are replaced with comparable sequences from a non-lentiviral retrovirus, thereby forming hybrid LTRs. In particular, the lentiviral R region within the LTR can be replaced in whole or in part by the R region from a non-lentiviral retrovirus. In certain embodiments, the lentiviral TAR sequence, a sequence which interacts with TAT protein to enhance viral replication, is removed, preferably in whole, from the R region. The TAR sequence is then replaced with a comparable portion of the R region from a non-lentiviral retrovirus, thereby forming a hybrid R region. The LTRs can be further modified to remove and/or replace with non-lentiviral sequences all or a portion of the lentiviral U3 and U5 regions.

Accordingly, in certain embodiments, the SIN configuration provides a retroviral LTR comprising a hybrid lentiviral R region that lacks all or a portion of its TAR sequence, thereby eliminating any possible activation by TAT, wherein the TAR sequence or portion thereof is replaced by a comparable portion of the R region from a non-lentiviral retrovirus, thereby forming a hybrid R region. In a particular embodiment, the retroviral LTR comprises a hybrid R region, wherein the hybrid R region comprises a portion of the HIV R region (e.g., a portion comprising or consisting of the nucleotide sequence shown in SEQ ID NO: 10 in US 2003/0039636) lacking the TAR sequence, and a portion of the MoMSV R region (e.g., a portion comprising or consisting of the nucleotide sequence shown in SEQ ID NO: 9 in 2003/0039636) comparable to the TAR sequence lacking from the HIV R region. In another particular embodiment, the entire hybrid R region comprises or consists of the nucleotide sequence shown in SEQ ID NO: 11 in 2003/0039636.

Suitable lentiviruses from which the R region can be derived include, for example, HIV (HIV-1 and HIV-2), EIV, SIV and FIV. Suitable retroviruses from which non-lentiviral sequences can be derived include, for example, MoMSV, MoMLV, Friend, MSCV, RSV and Spumaviruses. In one illustrative embodiment, the lentivirus is HIV and the non-lentiviral retrovirus is MoMSV.

In another embodiment described in US 2003/0039636, the LTR comprising a hybrid R region is a left (5') LTR and further comprises a promoter sequence upstream from the hybrid R region. Preferred promoters are non-lentiviral in origin and include, for example, the U3 region from a non-lentiviral retrovirus (e.g., the MoMSV U3 region). In one particular embodiment, the U3 region comprises the nucleotide sequence shown in SEQ ID NO: 12 in US 2003/0039636. In another embodiment, the left (5') LTR further comprises a lentiviral U5 region downstream from the hybrid R region. In one embodiment, the U5 region is the HIV U5 region including the HIV att site necessary for genomic integration. In another embodiment, the U5 region comprises the nucleotide sequence shown in SEQ ID NO: 13 in US 2003/0039636. In yet another embodiment, the entire left (5') hybrid LTR comprises the nucleotide sequence shown in SEQ ID NO: 1 in US 2003/0039636.

In another illustrative embodiment, the LTR comprising a hybrid R region is a right (3') LTR and further comprises a modified (e.g., truncated) lentiviral U3 region upstream from the hybrid R region. The modified lentiviral U3 region can include the att sequence, but lack any sequences having promoter activity, thereby causing the vector to be SIN in that viral transcription cannot go beyond the first round of replication following chromosomal integration. In a particular embodiment, the modified lentiviral U3 region upstream from the hybrid R region consists of the 3' end of a lentiviral (e.g., HIV) U3 region up to and including the lentiviral U3 att site. In one embodiment, the U3 region comprises the nucleotide sequence shown in SEQ ID NO: 15 in US 2003/0039636. In another embodiment, the right (3') LTR further comprises a polyadenylation sequence downstream from the hybrid R region. In another embodiment, the polyadenylation sequence comprises the nucleotide sequence shown in SEQ ID NO: 16 in US 2003/0039636. In yet another embodiment, the entire right (5') LTR comprises the nucleotide sequence shown in SEQ ID NO: 2 or 17 of US 2003/0039636.

Thus, in the case of HIV based LV, it has been discovered that such vectors tolerate significant U3 deletions, including the removal of the LTR TATA box (e.g., deletions from −418 to −18), without significant reductions in vector titers. These deletions render the LTR region substantially transcriptionally inactive in that the transcriptional ability of the LTR in reduced to about 90% or lower.

It has also been demonstrated that the trans-acting function of Tat becomes dispensable if part of the upstream LTR in the transfer vector construct is replaced by constitutively active promoter sequences (see, e.g., Dull et al. (1998) *J Virol.* 72(11): 8463-8471. Furthermore, we show that the expression of rev in trans allows the production of high-titer HIV-derived vector stocks from a packaging construct which contains only gag and pol. This design makes the expression of the packaging functions conditional on complementation available only in producer cells. The resulting gene delivery system, conserves only three of the nine genes of HIV-1 and relies on four separate transcriptional units for the production of transducing particles.

In one embodiments illustrated in Example 1, the cassette expressing an anti-sickling β-globin (e.g., βAS3) is placed in the pCCL LV backbone, which is a SIN vector with the CMV enhancer/promoter substituted in the 5' LTR.

It will be recognized that the CMV promoter typically provides a high level of non-tissue specific expression. Other promoters with similar constitutive activity include, but are not limited to the RSV promoter, and the SV40 promoter. Mammalian promoters such as the beta-actin promoter, ubiquitin C promoter, elongation factor 1 αpromoter, tubulin promoter, etc., may also be used.

The foregoing SIN configurations are illustrative and non-limiting. Numerous SIN configurations are known to those of skill in the art. As indicated above, in certain embodiments, the LTR transcription is reduced by about 95% to about 99%. In certain embodiments LTR may be rendered at least about 90%, at least about 91%, at least about 92%, at least about 93%, at least about 94%, at least about 95% at least about 96%, at least about 97%, at least about 98%, or at least about 99% transcriptionally inactive.

Insulator Element

In certain embodiments, to further enhance biosafety, insulators are inserted into the lentiviral vectors described herein. Insulators are DNA sequence elements present throughout the genome. They bind proteins that modify chromatin and alter regional gene expression. The placement of insulators in the vectors described herein offer various potential benefits including, inter alia: 1) Shielding of the vector from positional effect variegation of expression by flanking chromosomes (i.e., barrier activity); and 2) Shielding flanking chromosomes from insertional trans-activation of gene expression by the vector (enhancer blocking). Thus, insulators can help to preserve the independent function of genes or transcription units embedded in a genome or genetic context in which their expression may otherwise be influenced by regulatory signals within the genome or genetic context (see, e.g., Burgess-Beusse et al. (2002) *Proc. Natl. Acad. Sci. USA,* 99: 16433; and Zhan et al. (2001) *Hum. Genet.,* 109: 471). In the present context insulators may contribute to protecting lentivirus-expressed sequences from integration site effects, which may be mediated by cis-acting elements present in genomic DNA and lead to deregulated expression of transferred sequences. In various embodiments LVs are provided in which an insulator sequence is inserted into one or both LTRs or elsewhere in the region of the vector that integrates into the cellular genome.

The first and best characterized vertebrate chromatin insulator is located within the chicken β-globin locus control region. This element, which contains a DNase-I hypersensitive site-4 (cHS4), appears to constitute the 5' boundary of the chicken β-globin locus (Prioleau et al. (1999) *EMBO J.* 18: 4035-4048). A 1.2-kb fragment containing the cHS4 element displays classic insulator activities, including the ability to block the interaction of globin gene promoters and enhancers in cell lines (Chung et al. (1993) *Cell,* 74: 505-514), and the ability to protect expression cassettes in *Drosophila* (Id.), transformed cell lines (Pikaart et al. (1998) *Genes Dev.* 12: 2852-2862), and transgenic mammals (Wang et al. (1997) *Nat. Biotechnol.,* 15: 239-243; Taboit-Dameron et al. (1999) *Transgenic Res.,* 8: 223-235) from position effects. Much of this activity is contained in a 250-bp fragment. Within this stretch is a 49-bp cHS4 core (Chung et al. (1997) *Proc. Natl. Acad. Sci., USA,* 94: 575-580) that interacts with the zinc finger DNA binding protein CTCF implicated in enhancer-blocking assays (Bell et al. (1999) *Cell,* 98: 387-396).

One illustrative and suitable insulator is FB (FII/BEAD-A), a 77 bp insulator element, that contains the minimal CTCF binding site enhancer-blocking components of the chicken β-globin 5' HS4 insulators and a homologous region from the human T-cell receptor alpha/delta blocking element alpha/delta I (BEAD-I) insulator described by Ramezani et al. (2008) *Stem Cell* 26: 3257-3266. The FB "synthetic" insulator has full enhancer blocking activity. This insulator is illustrative and non-limiting. Other suitable insulators may be used including, for example, the full-length chicken beta-globin HS4 or insulator sub-fragments thereof, the ankyrin gene insulator, and other synthetic insulator elements.

Packaging Signal.

In various embodiments the vectors described herein further comprise a packaging signal. A "packaging signal," "packaging sequence," or "psi sequence" is any nucleic acid sequence sufficient to direct packaging of a nucleic acid whose sequence comprises the packaging signal into a retroviral particle. The term includes naturally occurring packaging sequences and also engineered variants thereof. Packaging signals of a number of different retroviruses, including lentiviruses, are known in the art.

Rev Responsive Element (RRE).

In certain embodiments the lentiviral vectors described herein comprise a Rev response element (RRE) to enhance nuclear export of unspliced RNA. RREs are well known to those of skill in the art. Illustrative RREs include, but are not limited to RREs such as that located at positions 7622-8459 in the HIV NL4-3 genome (Genbank accession number AF003887) as well as RREs from other strains of HIV or other retroviruses. Such sequences are readily available from Genbank or from the database with URL hiv-web.lanl.gov/content/index.

Central PolyPurine Tract (cPPT).

In various embodiments the lentiviral vectors described herein further include a central polypurine tract. Insertion of a fragment containing the central polypurine tract (cPPT) in lentiviral (e.g., HIV-1) vector constructs is known to enhance transduction efficiency drastically, reportedly by facilitating the nuclear import of viral cDNA through a central DNA flap.

Expression-Stimulating Posttranscriptional Regulatory Element (PRE)

In certain embodiments the lentiviral vectors (LVs) described herein may comprise any of a variety of posttranscriptional regulatory elements (PREs) whose presence within a transcript increases expression of the heterologous nucleic acid (e.g., βAS3) at the protein level. PREs may be particularly useful in certain embodiments, especially those that involve lentiviral constructs with modest promoters.

One type of PRE is an intron positioned within the expression cassette, which can stimulate gene expression. However, introns can be spliced out during the life cycle events of a lentivirus. Hence, if introns are used as PRE's they are typically placed in an opposite orientation to the vector genomic transcript.

Posttranscriptional regulatory elements that do not rely on splicing events offer the advantage of not being removed during the viral life cycle. Some examples are the posttranscriptional processing element of herpes simplex virus, the posttranscriptional regulatory element of the hepatitis B virus (HPRE) and the woodchuck hepatitis virus (WPRE). Of these the WPRE is typically preferred as it contains an additional cis-acting element not found in the HPRE. This regulatory element is typically positioned within the vector so as to be included in the RNA transcript of the transgene, but outside of stop codon of the transgene translational unit.

The WPRE is characterized and described in U.S. Pat. No. 6,136,597. As described therein, the WPRE is an RNA export element that mediates efficient transport of RNA from the nucleus to the cytoplasm. It enhances the expression of transgenes by insertion of a cis-acting nucleic acid sequence, such that the element and the transgene are contained within a single transcript. Presence of the WPRE in the sense orientation was shown to increase transgene expression by up to 7- to 10-fold. Retroviral vectors transfer sequences in the form of cDNAs instead of complete intron-containing genes as introns are generally spliced out during the sequence of events leading to the formation of the retroviral particle. Introns mediate the interaction of primary transcripts with the splicing machinery. Because the processing of RNAs by the splicing machinery facilitates their cytoplasmic export, due to a coupling between the splicing and transport machineries, cDNAs are often inefficiently expressed. Thus, the inclusion of the WPRE in a vector results in enhanced expression of transgenes.

Transduced Host Cells and Methods of Cell Transduction.

The recombinant lentiviral vectors (LV) and resulting virus described herein are capable of transferring a heterologous nucleic acid (e.g., a nucleic acid encoding an anti-sickling β-globin) sequence into a mammalian cell. In various embodiments, for delivery to cells, vectors described herein are preferably used in conjunction with a suitable packaging cell line or co-transfected into cells in vitro along with other vector plasmids containing the necessary retroviral genes (e.g., gag and pol) to form replication incompetent virions capable of packaging the vectors of the present invention and infecting cells.

The recombinant LVs and resulting virus described herein are capable of transferring a nucleic acid (e.g., a nucleic acid encoding an anti-sickling β-globin or other sequence) into a mammalian cell. For delivery to cells, various vectors described herein are preferably used in conjunction with a suitable packaging cell line or co-transfected into cells in vitro along with other vector plasmids containing the necessary retroviral genes (e.g., gag and pol) to form replication incompetent virions capable of packaging the vectors of the present invention and infecting cells.

In certain embodiments the vectors are introduced via transfection into the packaging cell line. The packaging cell line produces viral particles that contain the vector genome. Methods for transfection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with or without a dominant selectable marker, such as neomycin, DHFR, Glutamine synthetase, followed by selection in the presence of the appropriate drug and isolation of clones. In certain embodiments the selectable marker gene can be linked physically to the packaging genes in the construct.

Stable cell lines wherein the packaging functions are configured to be expressed by a suitable packaging cell are known (see, e.g., U.S. Pat. No. 5,686,279, which describes packaging cells). In general, for the production of virus particles, one may employ any cell that is compatible with the expression of lentiviral Gag and Pol genes, or any cell that can be engineered to support such expression. For example, producer cells such as 293T cells and HT1080 cells may be used.

The packaging cells with a lentiviral vector incorporated therein form producer cells. Producer cells are thus cells or cell-lines that can produce or release packaged infectious viral particles carrying the therapeutic gene of interest (e.g., modified β-globin). These cells can further be anchorage dependent which means that these cells will grow, survive, or maintain function optimally when attached to a surface such as glass or plastic. Some examples of anchorage dependent cell lines used as lentiviral vector packaging cell lines when the vector is replication competent are HeLa or 293 cells and PERC.6 cells.

Accordingly, in certain embodiments, methods are provided of delivering a gene to a cell which is then integrated into the genome of the cell, comprising contacting the cell with a virion containing a lentiviral vector described herein. The cell (e.g., in the form of tissue or an organ) can be contacted (e.g., infected) with the virion ex vivo and then delivered to a subject (e.g., a mammal, animal or human) in which the gene (e.g., anti-sickling (3-globin) will be expressed. In various embodiments the cell can be autologous to the subject (i.e., from the subject) or it can be non-autologous (i.e., allogeneic or xenogenic) to the subject. Moreover, because the vectors described herein are capable of being delivered to both dividing and non-dividing cells, the cells can be from a wide variety including, for example, bone marrow cells, mesenchymal stem cells (e.g., obtained from adipose tissue), and other primary cells derived from human and animal sources. Alternatively, the virion can be directly administered in vivo to a subject or a localized area of a subject (e.g., bone marrow).

Of course, as noted above, the lentivectors described herein will be particularly useful in the transduction of human hematopoietic progenitor cells or a hematopoietic stem cells, obtained either from the bone marrow, the peripheral blood or the umbilical cord blood, as well as in the transduction of a $CD4^+$ T cell, a peripheral blood B or T lymphocyte cell, and the like. In certain embodiments particularly preferred targets are $CD34^+$ hematopoetic stem and progenitor cells.

Gene Therapy.

In still other embodiments, methods are provide for transducing a human hematopoietic stem cell. In certain embodiments the methods involve contacting a population of human cells that include hematopoietic stem cells with one of the foregoing lentivectors under conditions to effect the transduction of a human hematopoietic progenitor cell in said population by the vector. The stem cells may be transduced in vivo or in vitro, depending on the ultimate application. Even in the context of human gene therapy, such as gene therapy of human stem cells, one may transduce the stem cell in vivo or, alternatively, transduce in vitro followed by infusion of the transduced stem cell into a human subject. In one aspect of this embodiment, the human stem cell can be removed from a human, e.g., a human patient, using methods well known to those of skill in the art and transduced as noted above. The transduced stem cells are then reintroduced into the same or a different human Stem Cell/Progenitor Cell Gene Therapy.

In various embodiments the lentivectors described herein are particularly useful for the transduction of human hematopoietic progenitor cells or haematopoietic stem cells (HSCs), obtained either from the bone marrow, the peripheral blood or the umbilical cord blood, as well as in the transduction of a $CD4^+$ T cell, a peripheral blood B or T lymphocyte cell, and the like. In certain embodiments particularly preferred targets are $CD34^+$ hematopoietic stem and progenitor cells.

When cells, for instance $CD34^+$ cells, dendritic cells, peripheral blood cells or tumor cells are transduced ex vivo, the vector particles are incubated with the cells using a dose generally in the order of between 1 to 50 multiplicities of infection (MOI) which also corresponds to $1\times10^5$ to $50\times10^5$ transducing units of the viral vector per $10^5$ cells. This can include amounts of vector corresponding to 1, 2, 3, 4, 5, 6, 7, 8, 9, 10, 15, 20, 25, 30, 35, 40, 45, and 50 MOI. Typically, the amount of vector may be expressed in terms of HT-29 transducing units (TU).

In certain embodiments cell-based therapies involve providing stem cells and/or hematopoietic precursors, transduce the cells with the lentivirus encoding, e.g., an anti-sickling human β-globin, and then introduce the transformed cells into a subject in need thereof (e.g., a subject with the sickle cell mutation).

In certain embodiments the methods involve isolating population of cells, e.g., stem cells from a subject, optionally expand the cells in tissue culture, and administer the lentiviral vector whose presence within a cell results in production of an anti-sickling β-globin in the cells in vitro. The cells are then returned to the subject, where, for example, they may provide a population of red blood cells that produce the anti-sickling β globin.

In some illustrative, but non-limiting, embodiments, a population of cells, which may be cells from a cell line or from an individual other than the subject, can be used. Methods of isolating stem cells, immune system cells, etc., from a subject and returning them to the subject are well known in the art. Such methods are used, e.g., for bone marrow transplant, peripheral blood stem cell transplant, etc., in patients undergoing chemotherapy.

Where stem cells are to be used, it will be recognized that such cells can be derived from a number of sources including bone marrow (BM), cord blood (CB), mobilized peripheral blood stem cells (mPBSC), and the like. In certain embodiments the use of induced pluripotent stem cells (IPSCs) is contemplated. Methods of isolating hematopoietic stem cells (HSCs), transducing such cells and introducing them into a mammalian subject are well known to those of skill in the art.

In certain embodiments a lentiviral vector described herein (see, e.g., FIG. 4) is used in stem cell gene therapy for SCD by introducing the βAS3 anti-sickling β-globin gene into the bone marrow stem cells of patients with sickle cell disease followed by autologous transplantation.

Direct Introduction of Vector.

In certain embodiments direct treatment of a subject by direct introduction of the vector(s) described herein is contemplated. The lentiviral compositions may be formulated for delivery by any available route including, but not limited to parenteral (e.g., intravenous), intradermal, subcutaneous, oral (e.g., inhalation), transdermal (topical), transmucosal, rectal, and vaginal. Commonly used routes of delivery include inhalation, parenteral, and transmucosal.

In various embodiments pharmaceutical compositions can include an LV in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

In some embodiments, active agents, i.e., a lentiviral described herein and/or other agents to be administered together the vector, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such compositions will be apparent to those skilled in the art. Suitable materials can also be obtained commercially from Alza Corporation and Nova Pharmaceuticals, Inc. Liposomes can also be used as pharmaceutically acceptable carriers. These can be prepared according to methods known to those skilled in the art, for example, as described in U.S. Pat. No. 4,522,811. In some embodiments the composition is targeted to particular cell types or to cells that are infected by a virus. For example, compositions can be targeted using monoclonal antibodies to cell surface markers, e.g., endogenous markers or viral antigens expressed on the surface of infected cells.

It is advantageous to formulate compositions in dosage unit form for ease of administration and uniformity of dosage. Dosage unit form as used herein refers to physically discrete units suited as unitary dosages for the subject to be treated; each unit comprising a predetermined quantity of a LV calculated to produce the desired therapeutic effect in association with a pharmaceutical carrier.

A unit dose need not be administered as a single injection but may comprise continuous infusion over a set period of time. Unit dose of the LV described herein may conveniently be described in terms of transducing units (T.U.) of lentivector, as defined by titering the vector on a cell line such as HeLa or 293. In certain embodiments unit doses can range from $10^3$, $10^4$, $10^5$, $10^6$, $10^7$, $10^8$, $10^9$, $10^{10}$, $10^{11}$, $10^{12}$, $10^{13}$ T.U. and higher.

Pharmaceutical compositions can be administered at various intervals and over different periods of time as required, e.g., one time per week for between about 1 to about 10 weeks; between about 2 to about 8 weeks; between about 3 to about 7 weeks; about 4 weeks; about 5 weeks; about 6 weeks, etc. It may be necessary to administer the therapeutic composition on an indefinite basis. The skilled artisan will appreciate that certain factors can influence the dosage and timing required to effectively treat a subject, including but not limited to the severity of the disease or disorder, previous treatments, the general health and/or age of the subject, and other diseases present. Treatment of a subject with a LV can include a single treatment or, in many cases, can include a series of treatments.

Illustrative, but non-limiting, doses for administration of gene therapy vectors and methods for determining suitable doses are known in the art. It is furthermore understood that appropriate doses of a LV may depend upon the particular recipient and the mode of administration. The appropriate dose level for any particular subject may depend upon a variety of factors including the age, body weight, general health, gender, and diet of the subject, the time of administration, the route of administration, the rate: of excretion, other administered therapeutic agents, and the like.

In certain embodiments lentiviral gene therapy vectors described herein can be delivered to a subject by, for example, intravenous injection, local administration, or by stereotactic injection (see, e.g., Chen et al. (1994) *Proc. Natl. Acad. Sci. USA,* 91: 3054). In certain embodiments vectors may be delivered orally or inhalationally and may be encapsulated or otherwise manipulated to protect them from degradation, enhance uptake into tissues or cells, etc. Pharmaceutical preparations can include a LV in an acceptable diluent, or can comprise a slow release matrix in which a LV is imbedded. Alternatively or additionally, where a vector can be produced intact from recombinant cells, as is the case for retroviral or lentiviral vectors as described herein, a pharmaceutical preparation can include one or more cells which produce vectors. Pharmaceutical compositions comprising a LV described herein can be included in a container, pack, or dispenser, optionally together with instructions for administration.

The foregoing compositions, methods and uses are intended to be illustrative and not limiting. Using the teachings provided herein other variations on the compositions, methods and uses will be readily available to one of skill in the art.

The approach to generate reduced length enhance regions is superior to previous strategies for generating tissue-specific enhancers for, among other reasons: 1) The cost of goods is decreased due to a low number of outputs required to be tested, 2) Strength of synthetic enhancers may be superior to those produced with current methods, or they may be less active but more suitable for LV-mediated delivery, and 3). Enhancers can be of minimal length.

Additionally, without being bound to a particular theory, it is believed the enhancer mapping strategy described herein can be modified to generate genome-wide enhancer maps using a similar cloning strategy and sonicated human genomic DNA and that the mapping strategies can be used to generate synthetic enhancers responsive to an array of distinct cellular perturbations.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING

Vector A (80 Sense)

SEQ ID NO: 1

GCGCAACGCAATTAATGTGAGTTAGCTCACTCATTAGGCACCCCAGGCTTTACACTTTATGC

TTCCGGCTCGTATGTTGTGTGGAATTGTGAGCGGATAACAATTTCACACAGGAAACAGCTAT

GACCATGATTACGCCAAGCGCGCAATTAACCCTCACTAAAGGGAACAAAAGCTGGAGCTGCA

AGCTTGGCCATTGCATACGTTGTATCCATATCATAATATGTACATTTATATTGGCTCATGTC

CAACATTACCGCCATGTTGACATTGATTATTGACTAGTTATTAATAGTAATCAATTACGGGG

TCATTAGTTCATAGCCCATATATGGAGTTCCGCGTTACATAACTTACGGTAAATGGCCCGCC

-continued

TGGCTGACCGCCCAACGACCCCCGCCCATTGACGTCAATAATGACGTATGTTCCCATAGTAA

CGCCAATAGGGACTTTCCATTGACGTCAATGGGTGGAGTATTTACGGTAAACTGCCCACTTG

GCAGTACATCAAGTGTATCATATGCCAAGTACGCCCCCTATTGACGTCAATGACGGTAAATG

GCCCGCCTGGCATTATGCCCAGTACATGACCTTATGGGACTTTCCTACTTGGCAGTACATCT

ACGTATTAGTCATCGCTATTACCATGGTGATGCGGTTTTGGCAGTACATCAATGGGCGTGGA

TAGCGGTTTGACTCACGGGGATTTCCAAGTCTCCACCCCATTGACGTCAATGGGAGTTTGTT

TTGGCACCAAAATCAACGGGACTTTCCAAAATGTCGTAACAACTCCGCCCCATTGACGCAAA

TGGGCGGTAGGCGTGTACGGTGGGAGGTCTATATAAGCAGAGCTCGTTTAGTGAACCGGGGT

CTCTCTGGTTAGACCAGATCTGAGCCTGGGAGCTCTCTGGCTAACTAGGGAACCCACTGCTT

AAGCCTCAATAAAGCTTGCCTTGAGTGCTTCAAGTAGTGTGTGCCCGTCTGTTGTGTGACTC

TGGTAACTAGAGATCCCTCAGACCCTTTTAGTCAGTGTGGAAAATCTCTAGCAGTGGCGCCC

GAACAGGGACTTGAAAGCGAAAGGGAAACCAGAGGAGCTCTCTCGACGCAGGACTCGGCTTG

CTGAAGCGCGCACGGCAAGAGGCGAGGGGCGGCGACTGGTGAGTACGCCAAAAATTTTGACT

AGCGGAGGCTAGAAGGAGAGAGATGGGTGCGAGAGCGTCAGTATTAAGCGGGGGAGAATTAG

ATCGCGATGGGAAAAAATTCGGTTAAGGCCAGGGGGAAAGAAAAAATATAAATTAAAACATA

TAGTATGGGCAAGCAGGGAGCTAGAACGATTCGCAGTTAATCCTGGCCTGTTAGAAACATCA

GAAGGCTGTAGACAAATACTGGGACAGCTACAACCATCCCTTCAGACAGGATCAGAAGAACT

TAGATCATTATATAATACAGTAGCAACCCTCTATTGTGTGCATCAAAGGATAGAGATAAAAG

ACACCAAGGAAGCTTTAGACAAGATAGAGGAAGAGCAAAACAAAAGTAAGACCACCGCACAG

CAAGCGGCCGCTGATCTTCAGACCTGGAGGAGGAGATATGAGGGACAATTGGAGAAGTGAAT

TATATAAATATAAAGTAGTAAAAATTGAACCATTAGGAGTAGCACCCACCAAGGCAAAGAGA

AGAGTGGTGCAGAGAGAAAAAAGAGCAGTGGGAATAGGAGCTTTGTTCCTTGGGTTCTTGGG

AGCAGCAGGAAGCACTATGGGCGCAGCGTCAATGACGCTGACGGTACAGGCCAGACAATTAT

TGTCTGGTATAGTGCAGCAGCAGAACAATTTGCTGAGGGCTATTGAGGCGCAACAGCATCTG

TTGCAACTCACAGTCTGGGGCATCAAGCAGCTCCAGGCAAGAATCCTGGCTGTGGAAAGATA

CCTAAAGGATCAACAGCTCCTGGGGATTTGGGGTTGCTCTGGAAAACTCATTTGCACCACTG

CTGTGCCTTGGAATGCTAGTTGGAGTAATAAATCTCTGGAACAGATTTGGAATCACACGACC

TGGATGGAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGGCAAGTT

TGTGGAATTGGTTTAACATAACAAATTGGCTGTGGTATATAAAATTATTCATAATGATAGTA

GGAGGCTTGGTAGGTTTAAGAATAGTTTTTGCTGTACTTTCTATAGTGAATAGAGTTAGGCA

GGGATATTCACCATTATCGTTTCAGACCCACCTCCCAACCCCGAGGGGACCCGACGGGCCCG

AAGGAATAGAAGAAGAAGGTGGAGAGAGAGACAGAGACAGATCCATTCGATTAGTGAACGGA

TCTCGACGGTATCGATCTCGACACAAATGGCAGTATTCATCCACAATTTTAAAAGAAAAGGG

GGGATTGGGGGGTACAGTGCAGGGGAAAGAATAGTAGACATAATAGCAACAGACATACAAAC

TAAAGAATTACAAAAACAAATTACAAAAATTCAAAATTTTCGGGTTTATTACAGGGACAGCA

GAGATCCAGTTTGGGTCGAGGATATCGGATCGGAATTCTCTAGATGATCAGGATCCCTCGAG

CCCTTATCGATCACGAGACTAGCCTCGACTACTAGTGGAGATCCCCCGGGCTGCAGAGCCAG

AAGCACCATAAGGGACATGATAAGGGAGCCAGCAGACCTCTGATCTCTTCCTGAATGCTAAT

CTTAAACATCCTGAGGAAGAATGGGACTTCCATTTGGGGTGGGCCTATGATAGGGTAATAAG

-continued

ACAGTAGTGAATATCAAGCTACAAAAAGCCCCCTTTCAAATTCTTCTCAGTCCTAACTTTTC

ATACTAAGCCCAGTCCTTCCAAAGCAGACTGTGAAAGAGTGATAGTTCCGGGAGACTAGCAC

TGCAGATTCCGGGTCACTGTGAGTGGGGGAGGCAGGGAAGAAGGGCTCACAGGACAGTCAAA

CCATGCCCCCTGTTTTTCCTTCTTCAAGTAGACCTCTATAAGACAACAGAGACAACTAAGGC

TGAGTGGCCAGGCGAGGAGAAACCATCTCGCCGTAAAACATGGAAGGAACACTTCAGGGGAA

AGGTGGTATCTCTAAGCAAGAGAACTGAGTGGAGTCAAGGCTGAGAGATGCAGGATAAGCAA

ATGGGTAGTGAAAAGACATTCATGAGGACAGCTAAAACAATAAGTAATGTAAAATACAGCAT

AGCAAAACTTTAACCTCCAAATCAAGCCTCTACTTGAATCCTTTTCTGAGGGATGAATAAGG

CATAGGCATCAGGGGCTGTTGCCAATGTGCATTAGCTGTTTGCAGCCTCACCTTCTTTCATG

GAGTTTAAGATATAGTGTATTTTCCCAAGGTTTGAACTAGCTCTTCATTTCTTTATGTTTTA

AATGCACTGACCTCCCACATTCCCTTTTTAGTAAAATATTCAGAAATAATTTAAATACATCA

TTGCAATGAAAATAAATGTTTTTTATTAGGCAGAATCCAGATGCTCAAGGCCCTTCATAATA

TCCCCCAGTTTAGTAGTTGGACTTAGGGAACAAAGGAACCTTTAATAGAAATTGGACAGCAA

GAAAGCGAGCTTAGTGATACTTGTGGGCCAGGGCATTAGCCACACCAGCCACCACTTTCTGA

TAGGCAGCCTGCACTGGTGGGGTGAATTCTTTGCCAAAGTGATGGGCCAGCACACAGACCAG

CACGTTGCCCAGGAGCTGTGGGAGGAAGATAAGAGGTATGAACATGATTAGCAAAAGGGCCT

AGCTTGGACTCAGAATAATCCAGCCTTATCCCAACCATAAAATAAAAGCAGAATGGTAGCTG

GATTGTAGCTGCTATTAGCAATATGAAACCTCTTACATCAGTTACAATTTATATGCAGAAAT

ATTTATATGCAGAAATATTGCTATTGCCTTAACCCAGAAATTATCACTGTTATTCTTTAGAA

TGGTGCAAAGAGGCATGATACATTGTATCATTATTGCCCTGAAAGAAAGAGATTAGGGAAAG

TATTAGAAATAAGATAAACAAAAAAGTATATTAAAAGAAGAAAGCATTTTTTAAAATTACAA

ATGCAAAATTACCCTGATTTGGTCAATATGTGTACCCTGTTACTTCTCCCCTTCCTATGACA

TGAACTTAACCATAGAAAAGAAGGGGAAAGAAAACATCAAGGGTCCCATAGACTCACCCTGA

AGTTCTCAGGATCCACGTGCAGCTTGTCACAGTGCAGCTCACTCAGCTGGGCAAAGGTGCCC

TTGAGGTTGTCCAGGTGAGCCAGGCCATCACTAAAGGCACCGAGCACTTTCTTGCCATGAGC

CTTCACCTTAGGGTTGCCCATAACAGCATCAGGAGTGGACAGATCCCCAAAGGACTCAAAGA

ACCTCTGGGTCCAAGGGTAGACCACCAGCAGCCTAAGGGTGGGAAAATAGACCAATAGGCAG

AGAGAGTCAGTGCCTATCAGAAACCCAAGAGTCTTCTCTGTCTCCACATGCCCAGTTTCTAT

TGGTCTCCTTAAACCTGTCTTGTAACCTTGATACCAACCTGCCCAGGGCCTCACCACCAACG

GCATCCACGTTCACCTTGTCCCACAGGGCAGTAACGGCAGACTTCTCCTCAGGAGTCAGGTG

CACCATGGTGTCTGTTTGAGGTTGCTAGTGAACACAGTTGTGTCAGAAGCAAATGTAAGCAA

TAGATGGCTCTGCCCTGACTTTTATGCCCAGCCCTGGCTCCTGCCCTCCCTGCTCCTGGGAG

TAGATTGGCCAACCCTAGGGTGTGGCTCCACAGGGTGAGGTCTAAGTGATGACAGCCGTACC

TGTCCTTGGCTCTTCTGGCACTGGCTTAGGAGTTGGACTTCAAACCCTCAGCCCTCCCTCTA

AGATATATCTCTTGGCCCCATACCATCAGTACAAATTGCTACTAAAAACATCCTCCTTTGCA

AGTGTATTTACCCGACGCGTCGGCGATAAGCTTGATCCATCGATTATTGAGGCTAAGGCATC

TGTGAAGGAAAGAAACATCTCCTCTAAACCACTATGCTGCTAGAGCCTCTTTTCTGTACTCA

AGCCTCATTCAGACACTAGTGTCACCAGTCTCCTCATATACCTATTGTATTTTCTTCTTCTT

GCTGGTTTAGTCATGTTTTCTGGGAGCTTAGGGGCTTATTTTATTTTGTTTTGTTTTCTAAT

CAACAGAGATGGGCAAACCCATTATTTTTTTCTTTAGACTTGGGATGGTGATAGCTGGGCAG

CGTCAGAAACTGTGTGTGGATATAGATAAGAGCTCAGGACTATGCTGAGCTGTGATGAGGGA

-continued

GGGGCCTAGCTAAAGGCAGTGAGAGTCAGAATGCTCCTGCTATTGCCTTCTCAGTCCCCACG

CTTGGTTTCTACACAAGTAGATACATAGAAAAGGCTATAGGTTCATCCTTCCCATGAAGATG

GATGAATAAGCCATATCTGACACCTATGAAATAATGTTTACTTTAGTGGCATATTGCATTAG

GCTACCTGCCTTGGCACAGTTTTTCTTTACTTTTACCTGACTGATGAAACAATTAATTGCTT

ACATAAACATGAGTGCTCTAGTTATAAATTCCAGTGTAAAAAACACCCTGGTTTCGATATTC

ATCTTTTGAGCCTTTTATTTTGGTCAGAACAAGTTTTCAAGAGCAAATCTCAGCCTACAAAA

CAAATGAGTCCAATTCTAGAACTCTTTGTGTGTGCATAGCAGTGGATGTGTCAGCATACATC

CTTTTAATTATAGTTGTATATGTGTTTGACTGCTCATTCATTCATTCAAAATTGTAAAATTG

CTAAGAATACAGCACAAAAACAGAATAGAGGAATAAAGTTCCTGTTTTCATGGACTTGATAG

TGGAAAGAGCTTGACATTAAATAAGCAAATGAAACATGTTATATACCAATGAGATTAGGTGC

TATGGAGAAAAAAAAAAAACTGAAATGAAGGCCAGAGTGTGATTAGGACAGGGTGAAAGGGT

ATCGCTACTTTAAGTAGTATGGCAGGAAAGTCCTCACTATAAAGTTAACACCTGAGAGAGTA

CCCATAGATGATGAGGAACCCATTTATATGAAACTATGATTAATTCCTCAGGACCATCTACA

TAATTTCTAGGCCCAATATAAAATGAAAATGAATAGCCCCTTTGTCAAAAATTAAGGATTTC

ATGTCAGGAACAGCAAGGATGTTAAACCAAGCATGGGGCCATCAAGCTATATCTGCTATTCA

TGATACGAAAAAATAAAGAGTATTCTAGTTATTTAGCCACATATTTCAAGTTTAGTCTGATA

TCACCCTTTAAACACTGCCACTCAACCTAAAACAATGCTAGTCTGGCCTTTTGCCACCTAGC

TGTCCAGGGGTGCCTTAAAATGGCAAACAAGGTTTGTTTTCTTTTCCTGTTTTCATGCCTTC

CTCTTCCATATCCTTGTTTCATATTAATACATGTGTATAGATCCTAAAAATCTATACACATG

TATTAATAAAGCCTGATTCTGCCGCTTCTAGGTATAGAGGCCACCTGCAAGATAAATATTTG

ATTCACAATAACTAATCATTCTATGGCAATTGATAACAACAAATATATATATATATATATAT

ATACGTGTATGTGTATATATATATATATATATATTCAGGAAATAATATATTCTAGAATATGT

CACATTCTGTCTCAGGCATCCATTTTCTTTATGATGCCGTTTGAGGTGGAGTTTTAGTCAGG

TGGTCAGCTTCTCCTTTTTTTTGCCATCTGCCCTGTAAGCATCCTGCTGGGGACCCAGATAG

GAGTCATCACTCTAGGCTGAGAACATCTGGGCACACACCCTAAGCCTCAGCATGACTCATCA

TGACTCAGCATTGCTGTGCTTGAGCCAGAAGGTTTGCTTAGAAGGTTACACAGAACCAGAAG

GCGGGGGTGGGGCACTGACCCCGACAGGGGCCTGGCCAGAACTGCTCATGCTTGGACTATGG

GAGGTCACTAATGGAGACACACAGAAATGTAACAGGCCCTCTACTCATGGTCTATCTCTCCT

GGCTCCTGGGAGTCATGGACTCCACCCAGCACCACCAACCTGACCTAACCACCTATCTGAGC

CTGCCAGCCTATAACCCATCTGGGCCCTGATAGCTGGTGGCCAGCCCTGACCCCACCCCACC

CTCCCTGGAACCTCTGATAGACACATCTGGCACACCAGCTCGCAAAGTCACCGTGAGGGTCT

TGTGTTTGCTGAGTCAAAATTCCTTGAAATCCAAGTCCTTAGAGACTCCTGCTCCCAAATTT

ACAGTCATAGACTTCTTCATGGCTGTCTCCTTTATCCACAGAATGATTCCTTTGCTTCATTG

CCCCATCCATCTGATCCTCCTCATCAGTGCAGCACAGGGCCCATGAGCAGTATCCTCTTATT

ATATTCTTCTTATAGTGATTCTGGATATTAAAGTGGGAATGAGGGGCAGGCCACTAACGAAG

AAGATGTTTCTCAAAGAAGCCATTCTCCCCACATAGATCATCTCAGCAGGGTTCAGGAAGAT

AAAGGAGGATCAAGGTCGAAGGTAGGAACTAAGGAAGAACACTGGGCAAGTGGATCCAGGTT

GTCCAACGCTGAAAGTAGGAATCTAAGCACTAGTCTCTGGATGCTAGGAGGGCCTCTGCATG

GGTATCAGGCTTGGATTCAAAGCTCCTGACTTTCTGTCTAGTGTATGTGCAGTGAGCCCCTT

TTCCTCTAACTGAAAGAAGGAAAAAAAAAATGGAACCCAAAATATTCTACATAGTTTCCATGT

-continued

CACAGCCAGGGCTGGGCAGTCTCCTGTTATTTCTTTTAAAATAAATATATCATTTAAATGCA

TAAATAAGCAAACCCTGCTCGGGAATGGGAGGGAGAGTCTCTGGAGTCCACCCCTTCTCGGC

CCTGGCTCTGCAGATAGTGCTATCAAAGCCCTGACAGAGCCCTGCCCATTGCTGGGCCTTGG

AGTGAGTCAGCCTAGTAGAGAGGCAGGGCAAGCCATCTCATAGCTGCTGAGTGGGAGAGAGA

AAAGGGCTCATTGTCTATAAACTCAGGTCATGGCTATTCTTATTCTCACACTAAGAAAAAGA

ATGAGATGTCATCTTGGACCATTAGCTCCACAGGTATCTTCTTCCCTCTAGTGGTCATAACA

GCAGCTTCAGCTACCTCTCTAAAGAGTCCTGCCAGATATAGGTCAGGAAATATAATCCACTA

ATAAAAAGAGAAACATTTTGACTGTAGTTGTTTGTTTTTTGTCATTGTGACTATCAATAACA

TTCTCACTCTTTCATCAGTAATCACTCAGGTTATTCTGTGACCAACAGACTGTGGGAAAAAT

CAGAGAAGGAGGCATCCTCATGCTTACTAGCCTAAACTGAAATTGCTATAGCAGAGTGAACC

AGAAGGTTTACAGATATTTTCCACAAAGAGTAAAAGGATTGAAGCCTTCTCCAGATCAATGC

ATAGGAAATAATAATGGACCATAAAACCCATATTATGACGAACAACATTAGGATAAGTCGGC

CTACTCGACCACGAGGGAATTCCGATAATCAACCTCTGGATTACAAAATTTGTGAAAGATTG

ACTGGTATTCTTAACTATGTTGCTCCTTTTACGCTATGTGGATACGCTGCTTTAATGCCTTT

GTATCATGCTATTGCTTCCCGTATGGCTTTCATTTTCTCCTCCTTGTATAAATCCTGGTTGC

TGTCTCTTTATGAGGAGTTGTGGCCCGTTGTCAGGCAACGTGGCGTGGTGTGCACTGTGTTT

GCTGACGCAACCCCCACTGGTTGGGGCATTGCCACCACCTGTCAGCTCCTTTCCGGGACTTT

CGCTTTCCCCCTCCCTATTGCCACGGCGGAACTCATCGCCGCCTGCCTTGCCCGCTGCTGGA

CAGGGGCTCGGCTGTTGGGCACTGACAATTCCGTGGTGTTGTCGGGGAAATCATCGTCCTTT

CCTTGGCTGCTCGCCTGTGTTGCCACCTGGATTCTGCGCGGGACGTCCTTCTGCTACGTCCC

TTCGGCCCTCAATCCAGCGGACCTTCCTTCCCGCGGCCTGCTGCCGGCTCTGCGGCCTCTTC

CGCGTCTTCGCCTTCGCCCTCAGACGAGTCGGATCTCCCTTTGGGCCGCCTCCCCGCATCGA

TACCGTCGACCTCGAGACCTAGAAAAACATGGCCAATTCGAGCTCGGTACCTTTAAGACCAA

TGACTTACAAGGCAGCTGTAGATCTTAGCCACTTTTTAAAAGAAAAGGGGGGACTGGAAGGG

CTAATTCACTCCCAACGAAGACAAGATCCCAGGGATGTACGTCCCTAACCCGCTAGGGGGCA

GCACCCAGGCCTGCACTGCCGCCTGCCGGCAGGGGTCCAGTCCTGCTTTTTGCTTGTACTGG

GTCTCTCTGGTTAGACCAGATCTGAGCCTGGGAGCTCTCTGGCTAACTAGGGAACCCACTGC

TTAAGCCTCAATAAAGCTTGCCTTGAGTGCTTCAAGTAGTGTGTGCCCGTCTGTTGTGTGAC

TCTGGTAACTAGAGATCCCTCAGACCCTTTTAGTCAGTGTGGAAAATCTCTAGCAGTAGTAG

TTCATGTCATCTTATTATTCAGTATTTATAACTTGCAAAGAAATGAATATCAGAGAGTGAGA

GGAACTTGTTTATTGCAGCTTATAATGGTTACAAATAAAGCAATAGCATCACAAATTTCACA

AATAAAGCATTTTTTTCACTGCATTCTAGTTGTGGTTTGTCCAAACTCATCAATGTATCTTA

TCATGTCTGGCTCTAGCTATCCCGCCCCTAACTCCGCCCATCCCGCCCCTAACTCCGCCCAG

TTCCGCCCATTCTCCGCCCCATGGCTGACTAATTTTTTTTATTTATGCAGAGGCCGAGGCCG

CCTCGGCCTCTGAGCTATTCCAGAAGTAGTGAGGAGGCTTTTTTGGAGGCCTAGGCTTTTGC

GTCGAGACGTACCCAATTCGCCCTATAGTGAGTCGTATTACGCGCGCTCACTGGCCGTCGTT

TTACAACGTCGTGACTGGGAAAACCCTGGCGTTACCCAACTTAATCGCCTTGCAGCACATCC

CCCTTTCGCCAGCTGGCGTAATAGCGAAGAGGCCCGCACCGATCGCCCTTCCCAACAGTTGC

GCAGCCTGAATGGCGAATGGCGCGACGCGCCCTGTAGCGGCGCATTAAGCGCGGCGGGTGTG

GTGGTTACGCGCAGCGTGACCGCTACACTTGCCAGCGCCCTAGCGCCCGCTCCTTTCGCTTT

CTTCCCTTCCTTTCTCGCCACGTTCGCCGGCTTTCCCCGTCAAGCTCTAAATCGGGGGCTCC

-continued

CTTTAGGGTTCCGATTTAGTGCTTTACGGCACCTCGACCCCAAAAAACTTGATTAGGGTGAT

GGTTCACGTAGTGGGCCATCGCCCTGATAGACGGTTTTTCGCCCTTTGACGTTGGAGTCCAC

GTTCTTTAATAGTGGACTCTTGTTCCAAACTGGAACAACACTCAACCCTATCTCGGTCTATT

CTTTTGATTTATAAGGGATTTTGCCGATTTCGGCCTATTGGTTAAAAAATGAGCTGATTTAA

CAAAAATTTAACGCGAATTTTAACAAAATATTAACGTTTACAATTTCCCAGGTGGCACTTTT

CGGGGAAATGTGCGCGGAACCCCTATTTGTTTATTTTTCTAAATACATTCAAATATGTATCC

GCTCATGAGACAATAACCCTGATAAATGCTTCAATAATATTGAAAAAGGAAGAGTATGAGTA

TTCAACATTTCCGTGTCGCCCTTATTCCCTTTTTTGCGGCATTTTGCCTTCCTGTTTTTGCT

CACCCAGAAACGCTGGTGAAAGTAAAAGATGCTGAAGATCAGTTGGGTGCACGAGTGGGTTA

CATCGAACTGGATCTCAACAGCGGTAAGATCCTTGAGAGTTTTCGCCCCGAAGAACGTTTTC

CAATGATGAGCACTTTTAAAGTTCTGCTATGTGGCGCGGTATTATCCCGTATTGACGCCGGG

CAAGAGCAACTCGGTCGCCGCATACACTATTCTCAGAATGACTTGGTTGAGTACTCACCAGT

CACAGAAAAGCATCTTACGGATGGCATGACAGTAAGAGAATTATGCAGTGCTGCCATAACCA

TGAGTGATAACACTGCGGCCAACTTACTTCTGACAACGATCGGAGGACCGAAGGAGCTAACC

GCTTTTTTGCACAACATGGGGGATCATGTAACTCGCCTTGATCGTTGGGAACCGGAGCTGAA

TGAAGCCATACCAAACGACGAGCGTGACACCACGATGCCTGTAGCAATGGCAACAACGTTGC

GCAAACTATTAACTGGCGAACTACTTACTCTAGCTTCCCGGCAACAATTAATAGACTGGATG

GAGGCGGATAAAGTTGCAGGACCACTTCTGCGCTCGGCCCTTCCGGCTGGCTGGTTTATTGC

TGATAAATCTGGAGCCGGTGAGCGTGGGTCTCGCGGTATCATTGCAGCACTGGGGCCAGATG

GTAAGCCCTCCCGTATCGTAGTTATCTACACGACGGGGAGTCAGGCAACTATGGATGAACGA

AATAGACAGATCGCTGAGATAGGTGCCTCACTGATTAAGCATTGGTAACTGTCAGACCAAGT

TTACTCATATATACTTTAGATTGATTTAAAACTTCATTTTTAATTTAAAAGGATCTAGGTGA

AGATCCTTTTTGATAATCTCATGACCAAAATCCCTTAACGTGAGTTTTCGTTCCACTGAGCG

TCAGACCCCGTAGAAAAGATCAAAGGATCTTCTTGAGATCCTTTTTTTCTGCGCGTAATCTG

CTGCTTGCAAACAAAAAAACCACCGCTACCAGCGGTGGTTTGTTTGCCGGATCAAGAGCTAC

CAACTCTTTTTCCGAAGGTAACTGGCTTCAGCAGAGCGCAGATACCAAATACTGTCCTTCTA

GTGTAGCCGTAGTTAGGCCACCACTTCAAGAACTCTGTAGCACCGCCTACATACCTCGCTCT

GCTAATCCTGTTACCAGTGGCTGCTGCCAGTGGCGATAAGTCGTGTCTTACCGGGTTGGACT

CAAGACGATAGTTACCGGATAAGGCGCAGCGGTCGGGCTGAACGGGGGGTTCGTGCACACAG

CCCAGCTTGGAGCGAACGACCTACACCGAACTGAGATACCTACAGCGTGAGCTATGAGAAAG

CGCCACGCTTCCCGAAGGGAGAAAGGCGGACAGGTATCCGGTAAGCGGCAGGGTCGGAACAG

GAGAGCGCACGAGGGAGCTTCCAGGGGGAAACGCCTGGTATCTTTATAGTCCTGTCGGGTTT

CGCCACCTCTGACTTGAGCGTCGATTTTTGTGATGCTCGTCAGGGGGGCGGAGCCTATGGAA

AAACGCCAGCAACGCGGCCATTTTTACGGTTCCTGGCCTTTTGCTGGCCTTTTGCTCACATG

TTCTTTCCTGCGTTATCCCCTGATTCTGTGGATAACCGTATTACCGCCTTTGAGTGAGCTGA

TACCGCTCGCCGCAGCCGAACGACCGAGCGCAGCGAGTCAGTGAGCGAGGAAGCGGAAGAGC

GCCCAATACGCAAACCGCCTCTCCCCGCGCGTTGGCCGATTCATTAATGCAGCTGGCACGAC

AGGTTTCCCGACTGGAAAGCGGGCAGTGA

-continued

Vector A (80 Sense) HS1.1

SEQ ID NO: 2
TATTGAGGCTAAGGCATCTGTGAAGGAAAGAAACATCTCCTCTAAACCACTATGCTGCTAGA
GCCTCTTTTCTGTACTCAAGCCTCATTCAGACACTAGTGTCACCAGTCTCCTCATATACCTA
TTGTATTTTCTTCTTCTTGCTGGTTTAGTCATGTTTTCTGGGAGCTTAGGGGCTTATTTTAT
TTTGTTTTGTTTTCTAATCAACAGAGATGGGCAAACCCATTATTTTTTTCTTTAGACTTGGG
ATGGTGATAGCTGGGCAGCGTCAGAAACTGTGTGTGGATATAGATAAGAGCTCAGGACTATG
CTGAGCTGTGATGAGGGAGGGGCCTAGCTAAAGGCAGTGAGAGTCAGAATGCTCCTGCTATT
GCCTTCTCAGTCCCCACGCTTGGTTTCTACACAAGTAGATACATAGAAAAGGCTATAGGTT

Vector A (80 Sense) HS1.2

SEQ ID NO: 3
CATCCTTCCCATGAAGATGGATGAATAAGCCATATCTGACACCTATGAAATAATGTTTACTT
TAGTGGCATATTGCATTAGGCTACCTGCCTTGGCACAGTTTTTCTTTACTTTTACCTGACTG
ATGAAACAATTAATTGCTTACATAAACATGAGTGCTCTAGTTATAAATTCCAGTGTAAAAAA
CACCCTGGTTTCGATATTCATCTTTTGAGCCTTTTATTTTGGTCAGAACAAGTTTTCAAGAG
CAAATCTCAGCCTACAAAACAAATGAGTCCAATTCTAGAAC

Vector A (80 Sense) HS1.3

SEQ ID NO: 4
TCTTTGTGTGTGCATAGCAGTGGATGTGTCAGCATACATCCTTTTAATTATAGTTGTATATG
TGTTTGACTGCTCATTCATTCATTCAAAATTGTAAAATTGCTAAGAATACAGCACAAAAACA
GAATAGAGGAATAAAGTTCCTGTTTTCATGGACTTGATAGTGGAAAGAGCTTGACATTAAAT
AAGCAAATGAAACATGTTATATACCAATGAGATTAGGTGCTATGGAGAAAAAAAAAAAACTG
AAATGAAGGCCAGAGTGTGATTAGGACAGGGTGAAAGGGTATCGCTACTTTAAGTAGTATGG
CAGGAAAGTCCTCACTATAAAGTTAACACCTGAGAGAGTACCCATAGATGATGAGGAACCCA
TTTATATGAAACTATGATTA

Vector A (80 Sense) HS1.4

SEQ ID NO: 5
ATTCCTCAGGACCATCTACATAATTTCTAGGCCCAATATAAAATGAAAATGAATAGCCCCTT
TGTCAAAAATTAAGGATTTCATGTCAGGAACAGCAAGGATGTTAAACCAAGCATGGGGCCAT
CAAGCTATATCTGCTATTCATGATACGAAAAAATAAAGAGTATTCTAGTTATTTAGCCACAT
ATTTCAAGTTTAGTCTGATATCACCCTTTAAACACTGCCACTCAACCTAAAACAATGCTAGT
CT

Vector A (80 Sense) HS2.1

SEQ ID NO: 6
GGCCTTTTGCCACCTAGCTGTCCAGGGGTGCCTTAAAATGGCAAACAAGGTTTGTTTTCTTT
TCCTGTTTTCATGCCTTCCTCTTCCATATCCTTGTTTCATATTAATACATGTGTATAGATCC
TAAAAATCTATACACATGTATTAATAAAGCCTGATTCTGCCGCTTCTAGGTATAGAGGCCAC
CTGCAAGATAAATATTTGATTCACAATAACTAATCATTCTATGGCAATTGATAACAACAAAT
ATATATATATATATATATATACGTGTATGTGTATATATATATATATATATATTCAGGAAATA
ATATATTCTAGAATATGTCACATTCTGTCTCAGGCATCCATTTTCTTTATGATGCCGTTTGA
GGTGGAGTTTTAGTCAGGTGGTCAGCTTCTCCTTTTTTTTGCCATCTGCCCTGTAAGCATCC
TGCTGGGGACCCAGATAGGAGTCATCACTCTAGGCTGAGAACATCTGGGCACACACCCTAAG
CCTCAGCATGACTCATCATGACTCAGCATTGCTGTGCTTGAGCCAGAAGGTTTGCTTAGAAG
GTTACACAGAACCAGAAGGCGGGGGTGGGGCACTGACCCCGACAGGGGCCTGGCCAGAACTG
CTCATGCTTGGACTATGGGAGGTCACTAATGGAGACACACAGAAATGTAACAG

-continued

Vector A (80 Sense) HS3.1

SEQ ID NO: 7

GCCCTCTACTCATGGTCTATCTCTCCTGGCTCCTGGGAGTCATGGACTCCACCCAGCACCAC

CAACCTGACCTAACCACCTATCTGAGCCTGCCAGCCTATAACCCATCTGGGCCCTGATAGCT

GGTGGCCAGCCCTGACCCCACCCCACCCTCCCTGGAACCTCTGATAGACACATCTGGCACAC

CAGCTCGCAAAGTCACCGTGAGGGTCTTGTGTTTGCTGAGTCAAAATTCCTTGAAATCCAAG

TCCTTAGAGACTCCTGCTCCCAAATTTACAGTCATAGACTTCTTCATGGCTGTCTCCTTTAT

CCACAGAATGATTCCTTTGCTTCATTGCCCCATCCATCTGATCCTCCTCATCAGTGCAGCAC

AGGGCCCATGAGCAGTA

Vector A (80 Sense) HS3.2

SEQ ID NO: 8

TCCTCTTATTATATTCTTCTTATAGTGATTCTGGATATTAAAGTGGGAATGAGGGGCAGGCC

ACTAACGAAGAAGATGTTTCTCAAAGAAGCCATTCTCCCCACATAGATCATCTCAGCAGGGT

TCAGGAAGATAAAGGAGGATCAAGGTCGAAGGTAGGAACTAAGGAAGAACACTGGGCAAGTG

GATCCAGGTTGTCCAACGCTGAAAGTAGGAATCTAAGCACTAGTCTCTGGATGCTAGGAGGG

CCTCTGCATGGG

Vector A (80 Sense) HS4.1

SEQ ID NO: 9

TATCAGGCTTGGATTCAAAGCTCCTGACTTTCTGTCTAGTGTATGTGCAGTGAGCCCCTTTT

CCTCTAACTGAAAGAAGGAAAAAAAAATGGAACCCAAAATATTCTACATAGTTTCCATGTCA

CAGCCAGGGCTGGGCAGTCTCCTGTTATTTCTTTTAAAATAAATATATCATTTAAATGCATA

AATAAGCAAACCCTGCTCGGGAATGGGAGGGAGAGTCTCTGGAGTCCACCCCTTCTCGGCCC

TGGCTCTGCAGATAGTGCTATCAAAGCCCTGACAGAGCCCTGCCCATTGCTGGGCCTTGGAG

TGAGTCAGCCTAGTAGAGAGGCAGGGCAAGCCATCTCATAGCTGCTGAGTGGGAGAGAGAAA

AGGGCTCATTGTCTATAAACTCAGGTCATGGCTATTCTTATTCTCACACTAAGAAAAAGAAT

GAGATGTC

Vector A (80 Sense) HS5.1

SEQ ID NO: 10

ATCTTGGACCATTAGCTCCACAGGTATCTTCTTCCCTCTAGTGGTCATAACAGCAGCTTCAG

CTACCTCTCTAAAGAGTCCTGCCAGATATAGGTCAGGAAATATAATCCACTAATAAAAAGAG

AAACATTTTGACTGTAGTTGTTTGTTTTTTGTCATTGTGACTATCAATAACATTCTCACTCT

TTCATCAGTAATCACTCAGGTTATTCTGTGACCAACAGACTGTGGGAAAAATCAGAGAAGGA

GGCATCCTCATGCTTACTAGCCTAAACTGAAATTGCTATAGCAGAGTGAACCAGAAGGTTTA

CAGATATTTTCCACAAAGAGTAAAAGGATTGAAGCCTTCTCCAGATCAATGCATAGGAAATA

ATAATGGACCATAAAACCCATATTATGACGAACAACATTAGGATAAGTC

Vector B (90 Sense)

SEQ ID NO: 11

GCGCAACGCAATTAATGTGAGTTAGCTCACTCATTAGGCACCCCAGGCTTTACACTTTATGC

TTCCGGCTCGTATGTTGTGTGGAATTGTGAGCGGATAACAATTTCACACAGGAAACAGCTAT

GACCATGATTACGCCAAGCGCGCAATTAACCCTCACTAAAGGGAACAAAAGCTGGAGCTGCA

AGCTTGGCCATTGCATACGTTGTATCCATATCATAATATGTACATTTATATTGGCTCATGTC

CAACATTACCGCCATGTTGACATTGATTATTGACTAGTTATTAATAGTAATCAATTACGGGG

TCATTAGTTCATAGCCCATATATGGAGTTCCGCGTTACATAACTTACGGTAAATGGCCCGCC

TGGCTGACCGCCCAACGACCCCCGCCCATTGACGTCAATAATGACGTATGTTCCCATAGTAA

CGCCAATAGGGACTTTCCATTGACGTCAATGGGTGGAGTATTTACGGTAAACTGCCCACTTG

GCAGTACATCAAGTGTATCATATGCCAAGTACGCCCCCTATTGACGTCAATGACGGTAAATG

-continued

GCCCGCCTGGCATTATGCCCAGTACATGACCTTATGGGACTTTCCTACTTGGCAGTACATCT

ACGTATTAGTCATCGCTATTACCATGGTGATGCGGTTTTGGCAGTACATCAATGGGCGTGGA

TAGCGGTTTGACTCACGGGGATTTCCAAGTCTCCACCCCATTGACGTCAATGGGAGTTTGTT

TTGGCACCAAAATCAACGGGACTTTCCAAAATGTCGTAACAACTCCGCCCCATTGACGCAAA

TGGGCGGTAGGCGTGTACGGTGGGAGGTCTATATAAGCAGAGCTCGTTTAGTGAACCGGGGT

CTCTCTGGTTAGACCAGATCTGAGCCTGGGAGCTCTCTGGCTAACTAGGGAACCCACTGCTT

AAGCCTCAATAAAGCTTGCCTTGAGTGCTTCAAGTAGTGTGTGCCCGTCTGTTGTGTGACTC

TGGTAACTAGAGATCCCTCAGACCCTTTTAGTCAGTGTGGAAAATCTCTAGCAGTGGCGCCC

GAACAGGGACTTGAAAGCGAAAGGGAAACCAGAGGAGCTCTCTCGACGCAGGACTCGGCTTG

CTGAAGCGCGCACGGCAAGAGGCGAGGGGCGGCGACTGGTGAGTACGCCAAAAATTTTGACT

AGCGGAGGCTAGAAGGAGAGAGATGGGTGCGAGAGCGTCAGTATTAAGCGGGGGAGAATTAG

ATCGCGATGGGAAAAAATTCGGTTAAGGCCAGGGGGAAAGAAAAAATATAAATTAAAACATA

TAGTATGGGCAAGCAGGGAGCTAGAACGATTCGCAGTTAATCCTGGCCTGTTAGAAACATCA

GAAGGCTGTAGACAAATACTGGGACAGCTACAACCATCCCTTCAGACAGGATCAGAAGAACT

TAGATCATTATATAATACAGTAGCAACCCTCTATTGTGTGCATCAAAGGATAGAGATAAAAG

ACACCAAGGAAGCTTTAGACAAGATAGAGGAAGAGCAAAACAAAAGTAAGACCACCGCACAG

CAAGCGGCCGCTGATCTTCAGACCTGGAGGAGGAGATATGAGGGACAATTGGAGAAGTGAAT

TATATAAATATAAAGTAGTAAAAATTGAACCATTAGGAGTAGCACCCACCAAGGCAAAGAGA

AGAGTGGTGCAGAGAGAAAAAAGAGCAGTGGGAATAGGAGCTTTGTTCCTTGGGTTCTTGGG

AGCAGCAGGAAGCACTATGGGCGCAGCGTCAATGACGCTGACGGTACAGGCCAGACAATTAT

TGTCTGGTATAGTGCAGCAGCAGAACAATTTGCTGAGGGCTATTGAGGCGCAACAGCATCTG

TTGCAACTCACAGTCTGGGGCATCAAGCAGCTCCAGGCAAGAATCCTGGCTGTGGAAAGATA

CCTAAAGGATCAACAGCTCCTGGGGATTTGGGGTTGCTCTGGAAAACTCATTTGCACCACTG

CTGTGCCTTGGAATGCTAGTTGGAGTAATAAATCTCTGGAACAGATTTGGAATCACACGACC

TGGATGGAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGGCAAGTT

TGTGGAATTGGTTTAACATAACAAATTGGCTGTGGTATATAAAATTATTCATAATGATAGTA

GGAGGCTTGGTAGGTTTAAGAATAGTTTTTGCTGTACTTTCTATAGTGAATAGAGTTAGGCA

GGGATATTCACCATTATCGTTTCAGACCCACCTCCCAACCCCGAGGGGACCCGACGGGCCCG

AAGGAATAGAAGAAGAAGGTGGAGAGAGAGACAGAGACAGATCCATTCGATTAGTGAACGGA

TCTCGACGGTATCGATCTCGACACAAATGGCAGTATTCATCCACAATTTTAAAAGAAAAGGG

GGGATTGGGGGGTACAGTGCAGGGGAAAGAATAGTAGACATAATAGCAACAGACATACAAAC

TAAAGAATTACAAAAACAAATTACAAAAATTCAAAATTTTCGGGTTTATTACAGGGACAGCA

GAGATCCAGTTTGGGTCGAGGATATCGGATCGGAATTCTCTAGATGATCAGGATCCCTCGAG

CCCTTATCGATCACGAGACTAGCCTCGACTACTAGTGGAGATCCCCCGGGCTGCAGAGCCAG

AAGCACCATAAGGGACATGATAAGGGAGCCAGCAGACCTCTGATCTCTTCCTGAATGCTAAT

CTTAAACATCCTGAGGAAGAATGGACTTCCATTTGGGGTGGGCCTATGATAGGGTAATAAG

ACAGTAGTGAATATCAAGCTACAAAAAGCCCCCTTTCAAATTCTTCTCAGTCCTAACTTTTC

ATACTAAGCCCAGTCCTTCCAAAGCAGACTGTGAAAGAGTGATAGTTCCGGGAGACTAGCAC

TGCAGATTCCGGGTCACTGTGAGTGGGGGAGGCAGGGAAGAAGGGCTCACAGGACAGTCAAA

-continued

```
CCATGCCCCCTGTTTTTCCTTCTTCAAGTAGACCTCTATAAGACAACAGAGACAACTAAGGC
TGAGTGGCCAGGCGAGGAGAAACCATCTCGCCGTAAAACATGGAAGGAACACTTCAGGGGAA
AGGTGGTATCTCTAAGCAAGAGAACTGAGTGGAGTCAAGGCTGAGAGATGCAGGATAAGCAA
ATGGGTAGTGAAAAGACATTCATGAGGACAGCTAAAACAATAAGTAATGTAAAATACAGCAT
AGCAAAACTTTAACCTCCAAATCAAGCCTCTACTTGAATCCTTTTCTGAGGGATGAATAAGG
CATAGGCATCAGGGGCTGTTGCCAATGTGCATTAGCTGTTTGCAGCCTCACCTTCTTTCATG
GAGTTTAAGATATAGTGTATTTTCCCAAGGTTTGAACTAGCTCTTCATTTCTTTATGTTTTA
AATGCACTGACCTCCCACATTCCCTTTTTAGTAAAATATTCAGAAATAATTTAAATACATCA
TTGCAATGAAAATAAATGTTTTTTATTAGGCAGAATCCAGATGCTCAAGGCCCTTCATAATA
TCCCCCAGTTTAGTAGTTGGACTTAGGGAACAAAGGAACCTTTAATAGAAATTGGACAGCAA
GAAAGCGAGCTTAGTGATACTTGTGGGCCAGGGCATTAGCCACACCAGCCACCACTTTCTGA
TAGGCAGCCTGCACTGGTGGGGTGAATTCTTTGCCAAAGTGATGGGCCAGCACACAGACCAG
CACGTTGCCCAGGAGCTGTGGGAGGAAGATAAGAGGTATGAACATGATTAGCAAAAGGGCCT
AGCTTGGACTCAGAATAATCCAGCCTTATCCCAACCATAAAATAAAAGCAGAATGGTAGCTG
GATTGTAGCTGCTATTAGCAATATGAAACCTCTTACATCAGTTACAATTTATATGCAGAAAT
ATTTATATGCAGAAATATTGCTATTGCCTTAACCCAGAAATTATCACTGTTATTCTTTAGAA
TGGTGCAAAGAGGCATGATACATTGTATCATTATTGCCCTGAAAGAAAGAGATTAGGGAAAG
TATTAGAAATAAGATAAACAAAAAAGTATATTAAAAGAAGAAAGCATTTTTTAAAATTACAA
ATGCAAAATTACCCTGATTTGGTCAATATGTGTACCCTGTTACTTCTCCCCTTCCTATGACA
TGAACTTAACCATAGAAAAGAAGGGGAAAGAAAACATCAAGGGTCCCATAGACTCACCCTGA
AGTTCTCAGGATCCACGTGCAGCTTGTCACAGTGCAGCTCACTCAGCTGGGCAAAGGTGCCC
TTGAGGTTGTCCAGGTGAGCCAGGCCATCACTAAAGGCACCGAGCACTTTCTTGCCATGAGC
CTTCACCTTAGGGTTGCCCATAACAGCATCAGGAGTGGACAGATCCCCAAAGGACTCAAAGA
ACCTCTGGGTCCAAGGGTAGACCACCAGCAGCCTAAGGGTGGGAAAATAGACCAATAGGCAG
AGAGAGTCAGTGCCTATCAGAAACCCAAGAGTCTTCTCTGTCTCCACATGCCCAGTTTCTAT
TGGTCTCCTTAAACCTGTCTTGTAACCTTGATACCAACCTGCCCAGGGCCTCACCACCAACG
GCATCCACGTTCACCTTGTCCCACAGGGCAGTAACGGCAGACTTCTCCTCAGGAGTCAGGTG
CACCATGGTGTCTGTTTGAGGTTGCTAGTGAACACAGTTGTGTCAGAAGCAAATGTAAGCAA
TAGATGGCTCTGCCCTGACTTTTATGCCCAGCCCTGGCTCCTGCCCTCCCTGCTCCTGGGAG
TAGATTGGCCAACCCTAGGGTGTGGCTCCACAGGGTGAGGTCTAAGTGATGACAGCCGTACC
TGTCCTTGGCTCTTCTGGCACTGGCTTAGGAGTTGGACTTCAAACCCTCAGCCCTCCCTCTA
AGATATATCTCTTGGCCCCATACCATCAGTACAAATTGCTACTAAAAACATCCTCCTTTGCA
AGTGTATTTACCCGACGCGTCGGCGATAAGCTTGATCCATCGATCAAGCCTCATTCAGACAC
TAGTGTCACCAGTCTCCTCATATACCTATTGTATTTTCTTCTTCTTGCTGGTTTAGTCATGT
TTTCTGGGAGCTTAGGGGCTTATTTTATTTTGTTTTGTTTTCTAATCAACAGAGATGGGCAA
ACCCATTATTTTTTTCTTTAGACTTGGGATGGTGATAGCTGGGCAGCGTCAGAAACTGTGTG
TGGATATAGATAAGAGCTCAGGACTATGCTGAGCTGTGATGAGGGAGGGGCCTAGCTAAAGG
CAGTGAGAGTCAGAATGCTCCTGCTATTGCCTTCTCAGTCCCCACGCTTGGTTTCTACACAA
GTATCTGACACCTATGAAATAATGTTTACTTTAGTGGCATATTGCATTAGGCTACCTGCCTT
GGCACAGTTTTTCTTTACTTTTACCTGACTGATGAAACAATTAATTGCTTACATAAACATGA
GTGCTCTAGTTATAAATTCCAGTGTAAAAAACACCCTGGTTTCGATATTCATCTTTTGAGCC
```

-continued

TTTTATTTTGGTCAGAACAAGTTTTCAAGAGCAAATCTCAGCCTACAAAACAAATGAGTCCA

ATTCTATACATCCTTTTAATTATAGTTGTATATGTGTTTGACTGCTCATTCATTCATTCAAA

ATTGTAAAATTGCTAAGAATACAGCACAAAAACAGAATAGAGGAATAAAGTTCCTGTTTTCA

TGGACTTGATAGTGGAAAGAGCTTGACATTAAATAAGCAAATGAAACATGTTATATACCAAT

GAGATTAGGTGCTATGGAGAAAAAAAAAAAAACTGAAATGAAGGCCAGAGTGTGATTAGGAC

AGGGTGAAAGGGTATCGCTACTTTAAGTAGTATGGCAGGAAAGTCCTCACTATAAAGTGGAT

TTCATGTCAGGAACAGCAAGGATGTTAAACCAAGCATGGGGCCATCAAGCTATATCTGCTAT

TCATGATACGAAAAAATAAAGAGTATTCTAGTTATTTAGCCACATATTTCAAGTAGCTGTCC

AGGGGTGCCTTAAAATGGCAAACAAGGTTTGTTTTCTTTTCCTGTTTTCATGCCTTCCTCTT

CCATATCCTTGTTTCATATTAATACATGTGTATAGATCCTAAAAATCTATACACATGTATTA

ATAAAGCCTGATTCTGCCGCTTCTAGGTATAGAGGCCACCTGCAAGATAAATATTTGATTCA

CAATAACTAATCATTCTATGGCAATTGATAACAACAAATATATATATATATATATATACGTA

TATGTGTATATATATATATATATATTCAGGAAATAATATATTCTAGAATATGTCACATTCTG

TCTCAGGCATCCATTTTCTTTATGATGCCGTTTGAGGTGGAGTTTTAGTCAGGTGGTCAGCT

TCTCCTTTTTTTTGCCATCTGCCCTGTAAGCATCCTGCTGGGGACCCAGATAGGAGTCATCA

CTCTAGGCTGAGAACATCTGGGCACACACCCTAAGCCTCAGCATGACTCATCATGACTCAGC

ATTGCTGTGCTTGAGCCAGAAGGTTTGCTTAGAAGGTTACACAGAACCAGAAGGCGGGGGTG

GGGCACTGACCCCGACAGGGGCCTGGCCAGAACTGCTCATGCTTGGACTATGGGAGGTCACT

AATGGAGACACACACATGGTCTATCTCTCCTGGCTCCTGGGAGTCATGGACTCCACCCAGCA

CCACCAACCTGACCTAACCACCTATCTGAGCCTGCCAGCCTATAACCCATCTGGGCCCTGAT

AGCTGGTGGCCAGCCCTGACCCCACCCCACCCTCCCTGGAACCTCTGATAGACACATCTGGC

ACACCAGCTCGCAAAGTCACCGTGAGGGTCTTGTGTTTGCTGAGTCAAAATTCCTTGAAATC

CAAGTCCTTAGAGACTCCTGCTCCCAAATTTACAGTCATAGACTTCTTCATGGCTGTCTCCT

TTATCCACAGAATGATTCCTTTGCTTCATTGCCCCATCCATCTGATCCTCCTCATCAGTGCA

GCACATAAAGTGGGAATGAGGGGCAGGCCACTAACGAAGAAGATGTTTCTCAAAGAAGCCAT

TCTCCCCACATAGATCATCTCAGCAGGGTTCAGGAAGATAAAGGAGGATCAAGGTCGAAGGT

AGGAACTAAGGAAGAACACTGGGCAAGTGGATCCAGGTTGTCCAACGCTGAAAGTAGGAATC

TAAGCACTAGTCTCTGGATGCTCTGTCTAGTGTATGTGCAGTGAGCCCCTTTTCCTCTAACT

GAAAGAAGGAAAAAAAAATGGAACCCAAAATATTCTACATAGTTTCCATGTCACAGCCAGGG

CTGGGCAGTCTCCTGTTATTTCTTTTAAAATAAATATATCATTTAAATGCATAAATAAGCAA

ACCCTGCTCGGGAATGGGAGGGAGAGTCTCTGGAGTCCACCCCTTCTCGGCCCTGGCTCTGC

AGATAGTGCTATCAAAGCCCTGACAGAGCCCTGCCCATTGCTGGGCCTTGGAGTGAGTCAGC

CTAGTAGAGAGGCAGGGCAAGCCATCTCATAGCTGCTGAGTGGGAGAGAGAAAAGGGCTCAT

TGTCTATAAACTCATAAAAAGAGAAACATTTTGACTGTAGTTGTTTGTTTTTTGTCATTGTG

ACTATCAATAACATTCTCACTCTTTCATCAGTAATCACTCAGGTTATTCTGTGACCAACAGA

CTGTGGGAAAAATCAGAGAAGGAGGCATCCTCATGCTTACTAGCCTAAACTGAAATTGCTAT

AGCAGAGTGAACCAGAAGGTTTACAGATATTTTCCACAAAGAGTAAAAGGATTGAAGCCTTC

TCCAGATCAATGCATAGGCCTACTCGACCACGAGGGAATTCCGATAATCAACCTCTGGATTA

CAAAATTTGTGAAAGATTGACTGGTATTCTTAACTATGTTGCTCCTTTTACGCTATGTGGAT

ACGCTGCTTTAATGCCTTTGTATCATGCTATTGCTTCCCGTATGGCTTTCATTTTCTCCTCC

-continued

TTGTATAAATCCTGGTTGCTGTCTCTTTATGAGGAGTTGTGGCCCGTTGTCAGGCAACGTGG

CGTGGTGTGCACTGTGTTTGCTGACGCAACCCCCACTGGTTGGGGCATTGCCACCACCTGTC

AGCTCCTTTCCGGGACTTTCGCTTTCCCCCTCCCTATTGCCACGGCGGAACTCATCGCCGCC

TGCCTTGCCCGCTGCTGGACAGGGGCTCGGCTGTTGGGCACTGACAATTCCGTGGTGTTGTC

GGGGAAATCATCGTCCTTTCCTTGGCTGCTCGCCTGTGTTGCCACCTGGATTCTGCGCGGGA

CGTCCTTCTGCTACGTCCCTTCGGCCCTCAATCCAGCGGACCTTCCTTCCCGCGGCCTGCTG

CCGGCTCTGCGGCCTCTTCCGCGTCTTCGCCTTCGCCCTCAGACGAGTCGGATCTCCCTTTG

GGCCGCCTCCCCGCATCGATACCGTCGACCTCGAGACCTAGAAAAACATGGCCAATTCGAGC

TCGGTACCTTTAAGACCAATGACTTACAAGGCAGCTGTAGATCTTAGCCACTTTTTAAAAGA

AAAGGGGGGACTGGAAGGGCTAATTCACTCCCAACGAAGACAAGATCCCAGGGATGTACGTC

CCTAACCCGCTAGGGGGCAGCACCCAGGCCTGCACTGCCGCCTGCCGGCAGGGGTCCAGTCC

TGCTTTTTGCTTGTACTGGGTCTCTCTGGTTAGACCAGATCTGAGCCTGGGAGCTCTCTGGC

TAACTAGGGAACCCACTGCTTAAGCCTCAATAAAGCTTGCCTTGAGTGCTTCAAGTAGTGTG

TGCCCGTCTGTTGTGTGACTCTGGTAACTAGAGATCCCTCAGACCCTTTTAGTCAGTGTGGA

AAATCTCTAGCAGTAGTAGTTCATGTCATCTTATTATTCAGTATTTATAACTTGCAAAGAAA

TGAATATCAGAGAGTGAGAGGAACTTGTTTATTGCAGCTTATAATGGTTACAAATAAAGCAA

TAGCATCACAAATTTCACAAATAAAGCATTTTTTTCACTGCATTCTAGTTGTGGTTTGTCCA

AACTCATCAATGTATCTTATCATGTCTGGCTCTAGCTATCCCGCCCCTAACTCCGCCCATCC

CGCCCCTAACTCCGCCCAGTTCCGCCCATTCTCCGCCCCATGGCTGACTAATTTTTTTTATT

TATGCAGAGGCCGAGGCCGCCTCGGCCTCTGAGCTATTCCAGAAGTAGTGAGGAGGCTTTTT

TGGAGGCCTAGGCTTTTGCGTCGAGACGTACCCAATTCGCCCTATAGTGAGTCGTATTACGC

GCGCTCACTGGCCGTCGTTTTACAACGTCGTGACTGGGAAAACCCTGGCGTTACCCAACTTA

ATCGCCTTGCAGCACATCCCCCTTTCGCCAGCTGGCGTAATAGCGAAGAGGCCCGCACCGAT

CGCCCTTCCCAACAGTTGCGCAGCCTGAATGGCGAATGGCGCGACGCGCCCTGTAGCGGCGC

ATTAAGCGCGGCGGGTGTGGTGGTTACGCGCAGCGTGACCGCTACACTTGCCAGCGCCCTAG

CGCCCGCTCCTTTCGCTTTCTTCCCTTCCTTTCTCGCCACGTTCGCCGGCTTTCCCCGTCAA

GCTCTAAATCGGGGGCTCCCTTTAGGGTTCCGATTTAGTGCTTTACGGCACCTCGACCCCAA

AAAACTTGATTAGGGTGATGGTTCACGTAGTGGGCCATCGCCCTGATAGACGGTTTTTCGCC

CTTTGACGTTGGAGTCCACGTTCTTTAATAGTGGACTCTTGTTCCAAACTGGAACAACACTC

AACCCTATCTCGGTCTATTCTTTTGATTTATAAGGGATTTTGCCGATTTCGGCCTATTGGTT

AAAAAATGAGCTGATTTAACAAAAATTTAACGCGAATTTTAACAAAATATTAACGTTTACAA

TTTCCCAGGTGGCACTTTTCGGGGAAATGTGCGCGGAACCCCTATTTGTTTATTTTTCTAAA

TACATTCAAATATGTATCCGCTCATGAGACAATAACCCTGATAAATGCTTCAATAATATTGA

AAAAGGAAGAGTATGAGTATTCAACATTTCCGTGTCGCCCTTATTCCCTTTTTTGCGGCATT

TTGCCTTCCTGTTTTTGCTCACCCAGAAACGCTGGTGAAAGTAAAAGATGCTGAAGATCAGT

TGGGTGCACGAGTGGGTTACATCGAACTGGATCTCAACAGCGGTAAGATCCTTGAGAGTTTT

CGCCCCGAAGAACGTTTTCCAATGATGAGCACTTTTAAAGTTCTGCTATGTGGCGCGGTATT

ATCCCGTATTGACGCCGGGCAAGAGCAACTCGGTCGCCGCATACACTATTCTCAGAATGACT

TGGTTGAGTACTCACCAGTCACAGAAAAGCATCTTACGGATGGCATGACAGTAAGAGAATTA

TGCAGTGCTGCCATAACCATGAGTGATAACACTGCGGCCAACTTACTTCTGACAACGATCGG

AGGACCGAAGGAGCTAACCGCTTTTTTGCACAACATGGGGGATCATGTAACTCGCCTTGATC

-continued

GTTGGGAACCGGAGCTGAATGAAGCCATACCAAACGACGAGCGTGACACCACGATGCCTGTA

GCAATGGCAACAACGTTGCGCAAACTATTAACTGGCGAACTACTTACTCTAGCTTCCCGGCA

ACAATTAATAGACTGGATGGAGGCGGATAAAGTTGCAGGACCACTTCTGCGCTCGGCCCTTC

CGGCTGGCTGGTTTATTGCTGATAAATCTGGAGCCGGTGAGCGTGGGTCTCGCGGTATCATT

GCAGCACTGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGATTAAGCATT

GGTAACTGTCAGACCAAGTTTACTCATATATACTTTAGATTGATTTAAAACTTCATTTTTAA

TTTAAAAGGATCTAGGTGAAGATCCTTTTTGATAATCTCATGACCAAAATCCCTTAACGTGA

GTTTTCGTTCCACTGAGCGTCAGACCCCGTAGAAAAGATCAAAGGATCTTCTTGAGATCCTT

TTTTTCTGCGCGTAATCTGCTGCTTGCAAACAAAAAAACCACCGCTACCAGCGGTGGTTTGT

TTGCCGGATCAAGAGCTACCAACTCTTTTTCCGAAGGTAACTGGCTTCAGCAGAGCGCAGAT

ACCAAATACTGTCCTTCTAGTGTAGCCGTAGTTAGGCCACCACTTCAAGAACTCTGTAGCAC

CGCCTACATACCTCGCTCTGCTAATCCTGTTACCAGTGGCTGCTGCCAGTGGCGATAAGTCG

TGTCTTACCGGGTTGGACTCAAGACGATAGTTACCGGATAAGGCGCAGCGGTCGGGCTGAAC

GGGGGGTTCGTGCACACAGCCCAGCTTGGAGCGAACGACCTACACCGAACTGAGATACCTAC

AGCGTGAGCTATGAGAAAGCGCCACGCTTCCCGAAGGGAGAAAGGCGGACAGGTATCCGGTA

AGCGGCAGGGTCGGAACAGGAGAGCGCACGAGGGAGCTTCCAGGGGGAAACGCCTGGTATCT

TTATAGTCCTGTCGGGTTTCGCCACCTCTGACTTGAGCGTCGATTTTTGTGATGCTCGTCAG

GGGGGCGGAGCCTATGGAAAAACGCCAGCAACGCGGCCATTTTTACGGTTCCTGGCCTTTTG

CTGGCCTTTTGCTCACATGTTCTTTCCTGCGTTATCCCCTGATTCTGTGGATAACCGTATTA

CCGCCTTTGAGTGAGCTGATACCGCTCGCCGCAGCCGAACGACCGAGCGCAGCGAGTCAGTG

AGCGAGGAAGCGGAAGAGCGCCCAATACGCAAACCGCCTCTCCCCGCGCGTTGGCCGATTCA

TTAATGCAGCTGGCACGACAGGTTTCCCGACTGGAAAGCGGGCAGTGA

Vector B (90 Sense) HS1.1

SEQ ID NO: 12

CAAGCCTCATTCAGACACTAGTGTCACCAGTCTCCTCATATACCTATTGTATTTTCTTCTTC

TTGCTGGTTTAGTCATGTTTTCTGGGAGCTTAGGGGCTTATTTTATTTTGTTTTGTTTTCTA

ATCAACAGAGATGGGCAAACCCATTATTTTTTTCTTTAGACTTGGGATGGTGATAGCTGGGC

AGCGTCAGAAACTGTGTGTGGATATAGATAAGAGCTCAGGACTATGCTGAGCTGTGATGAGG

GAGGGGCCTAGCTAAAGGCAGTGAGAGTCAGAATGCTCCTGCTATTGCCTTCTCAGTCCCCA

CGCTTGGTTTCTACACAAGTA

Vector B (90 Sense) HS1.2

SEQ ID NO: 13

TCTGACACCTATGAAATAATGTTTACTTTAGTGGCATATTGCATTAGGCTACCTGCCTTGGC

ACAGTTTTTCTTTACTTTTACCTGACTGATGAAACAATTAATTGCTTACATAAACATGAGTG

CTCTAGTTATAAATTCCAGTGTAAAAAACACCCTGGTTTCGATATTCATCTTTTGAGCCTTT

TATTTTGGTCAGAACAAGTTTTCAAGAGCAAATCTCAGCCTACAAAACAAATGAGTCCAATT

CTA

Vector B (90 Sense) HS1.3

SEQ ID NO: 14

TACATCCTTTTAATTATAGTTGTATATGTGTTTGACTGCTCATTCATTCATTCAAAATTGTA

AAATTGCTAAGAATACAGCACAAAAACAGAATAGAGGAATAAAGTTCCTGTTTTCATGGACT

TGATAGTGGAAAGAGCTTGACATTAAATAAGCAAATGAAACATGTTATATACCAATGAGATT

-continued

AGGTGCTATGGAGAAAAAAAAAAAAAACTGAAATGAAGGCCAGAGTGTGATTAGGACAGGGTG

AAAGGGTATCGCTACTTTAAGTAGTATGGCAGGAAAGTCCTCACTATAAAGT

Vector B (90 Sense) HS1.4

SEQ ID NO: 15

GGATTTCATGTCAGGAACAGCAAGGATGTTAAACCAAGCATGGGGCCATCAAGCTATATCTG

CTATTCATGATACGAAAAAATAAAGAGTATTCTAGTTATTTAGCCACATATTTCAAG

Vector B (90 Sense) HS2.1

SEQ ID NO: 16

TAGCTGTCCAGGGGTGCCTTAAAATGGCAAACAAGGTTTGTTTTCTTTTCCTGTTTTCATGC

CTTCCTCTTCCATATCCTTGTTTCATATTAATACATGTGTATAGATCCTAAAAATCTATACA

CATGTATTAATAAAGCCTGATTCTGCCGCTTCTAGGTATAGAGGCCACCTGCAAGATAAATA

TTTGATTCACAATAACTAATCATTCTATGGCAATTGATAACAACAAATATATATATATATAT

ATATACGTATATGTGTATATATATATATATATATTCAGGAAATAATATATTCTAGAATATGT

CACATTCTGTCTCAGGCATCCATTTTCTTTATGATGCCGTTTGAGGTGGAGTTTTAGTCAGG

TGGTCAGCTTCTCCTTTTTTTTGCCATCTGCCCTGTAAGCATCCTGCTGGGGACCCAGATAG

GAGTCATCACTCTAGGCTGAGAACATCTGGGCACACACCCTAAGCCTCAGCATGACTCATCA

TGACTCAGCATTGCTGTGCTTGAGCCAGAAGGTTTGCTTAGAAGGTTACACAGAACCAGAAG

GCGGGGGTGGGGCACTGACCCCGACAGGGGCCTGGCCAGAACTGCTCATGCTTGGACTATGG

GAGGTCACTAATGGAGACACACA

Vector B (90 Sense) HS3.1

SEQ ID NO: 17

CATGGTCTATCTCTCCTGGCTCCTGGGAGTCATGGACTCCACCCAGCACCACCAACCTGACC

TAACCACCTATCTGAGCCTGCCAGCCTATAACCCATCTGGGCCCTGATAGCTGGTGGCCAGC

CCTGACCCCACCCCACCCTCCCTGGAACCTCTGATAGACACATCTGGCACACCAGCTCGCAA

AGTCACCGTGAGGGTCTTGTGTTTGCTGAGTCAAAATTCCTTGAAATCCAAGTCCTTAGAGA

CTCCTGCTCCCAAATTTACAGTCATAGACTTCTTCATGGCTGTCTCCTTTATCCACAGAATG

ATTCCTTTGCTTCATTGCCCCATCCATCTGATCCTCCTCATCAGTGCAGCACA

Vector B (90 Sense) HS3.2

SEQ ID NO: 18

TAAAGTGGGAATGAGGGGCAGGCCACTAACGAAGAAGATGTTTCTCAAAGAAGCCATTCTCC

CCACATAGATCATCTCAGCAGGGTTCAGGAAGATAAAGGAGGATCAAGGTCGAAGGTAGGAA

CTAAGGAAGAACACTGGGCAAGTGGATCCAGGTTGTCCAACGCTGAAAGTAGGAATCTAAGC

ACTAGTCTCTGGATGCT

Vector B (90 Sense) HS4.1

SEQ ID NO: 19

CTGTCTAGTGTATGTGCAGTGAGCCCCTTTTCCTCTAACTGAAAGAAGGAAAAAAAAATGGA

ACCCAAAATATTCTACATAGTTTCCATGTCACAGCCAGGGCTGGGCAGTCTCCTGTTATTTC

TTTTAAAATAAATATATCATTTAAATGCATAAATAAGCAAACCCTGCTCGGGAATGGGAGGG

AGAGTCTCTGGAGTCCACCCCTTCTCGGCCCTGGCTCTGCAGATAGTGCTATCAAAGCCCTG

ACAGAGCCCTGCCCATTGCTGGGCCTTGGAGTGAGTCAGCCTAGTAGAGAGGCAGGGCAAGC

CATCTCATAGCTGCTGAGTGGGAGAGAGAAAAGGGCTCATTGTCTATAAACTC

Vector B (90 Sense) HS5.1

SEQ ID NO: 20

ATAAAAAGAGAAACATTTTGACTGTAGTTGTTTGTTTTTTGTCATTGTGACTATCAATAACA

TTCTCACTCTTTCATCAGTAATCACTCAGGTTATTCTGTGACCAACAGACTGTGGGAAAAAT

CAGAGAAGGAGGCATCCTCATGCTTACTAGCCTAAACTGAAATTGCTATAGCAGAGTGAACC

AGAAGGTTTACAGATATTTTCCACAAAGAGTAAAAGGATTGAAGCCTTCTCCAGATCAATGC

ATA

Vector C (95 Sense)

SEQ ID NO: 21

GCGCAACGCAATTAATGTGAGTTAGCTCACTCATTAGGCACCCCAGGCTTTACACTTTATGC

TTCCGGCTCGTATGTTGTGTGGAATTGTGAGCGGATAACAATTTCACACAGGAAACAGCTAT

GACCATGATTACGCCAAGCGCGCAATTAACCCTCACTAAAGGGAACAAAAGCTGGAGCTGCA

AGCTTGGCCATTGCATACGTTGTATCCATATCATAATATGTACATTTATATTGGCTCATGTC

CAACATTACCGCCATGTTGACATTGATTATTGACTAGTTATTAATAGTAATCAATTACGGGG

TCATTAGTTCATAGCCCATATATGGAGTTCCGCGTTACATAACTTACGGTAAATGGCCCGCC

TGGCTGACCGCCCAACGACCCCCGCCCATTGACGTCAATAATGACGTATGTTCCCATAGTAA

CGCCAATAGGGACTTTCCATTGACGTCAATGGGTGGAGTATTTACGGTAAACTGCCCACTTG

GCAGTACATCAAGTGTATCATATGCCAAGTACGCCCCCTATTGACGTCAATGACGGTAAATG

GCCCGCCTGGCATTATGCCCAGTACATGACCTTATGGGACTTTCCTACTTGGCAGTACATCT

ACGTATTAGTCATCGCTATTACCATGGTGATGCGGTTTTGGCAGTACATCAATGGGCGTGGA

TAGCGGTTTGACTCACGGGGATTTCCAAGTCTCCACCCCATTGACGTCAATGGGAGTTTGTT

TTGGCACCAAAATCAACGGGACTTTCCAAAATGTCGTAACAACTCCGCCCCATTGACGCAAA

TGGGCGGTAGGCGTGTACGGTGGGAGGTCTATATAAGCAGAGCTCGTTTAGTGAACCGGGGT

CTCTCTGGTTAGACCAGATCTGAGCCTGGGAGCTCTCTGGCTAACTAGGGAACCCACTGCTT

AAGCCTCAATAAAGCTTGCCTTGAGTGCTTCAAGTAGTGTGTGCCCGTCTGTTGTGTGACTC

TGGTAACTAGAGATCCCTCAGACCCTTTTAGTCAGTGTGGAAAATCTCTAGCAGTGGCGCCC

GAACAGGGACTTGAAAGCGAAAGGGAAACCAGAGGAGCTCTCTCGACGCAGGACTCGGCTTG

CTGAAGCGCGCACGGCAAGAGGCGAGGGGCGGCGACTGGTGAGTACGCCAAAAATTTTGACT

AGCGGAGGCTAGAAGGAGAGAGATGGGTGCGAGAGCGTCAGTATTAAGCGGGGGAGAATTAG

ATCGCGATGGGAAAAAATTCGGTTAAGGCCAGGGGGAAAGAAAAAATATAAATTAAAACATA

TAGTATGGGCAAGCAGGGAGCTAGAACGATTCGCAGTTAATCCTGGCCTGTTAGAAACATCA

GAAGGCTGTAGACAAATACTGGGACAGCTACAACCATCCCTTCAGACAGGATCAGAAGAACT

TAGATCATTATATAATACAGTAGCAACCCTCTATTGTGTGCATCAAAGGATAGAGATAAAAG

ACACCAAGGAAGCTTTAGACAAGATAGAGGAAGAGCAAAACAAAAGTAAGACCACCGCACAG

CAAGCGGCCGCTGATCTTCAGACCTGGAGGAGGAGATATGAGGGACAATTGGAGAAGTGAAT

TATATAAATATAAAGTAGTAAAAATTGAACCATTAGGAGTAGCACCCACCAAGGCAAAGAGA

AGAGTGGTGCAGAGAGAAAAAAGAGCAGTGGGAATAGGAGCTTTGTTCCTTGGGTTCTTGGG

AGCAGCAGGAAGCACTATGGGCGCAGCGTCAATGACGCTGACGGTACAGGCCAGACAATTAT

TGTCTGGTATAGTGCAGCAGCAGAACAATTTGCTGAGGGCTATTGAGGCGCAACAGCATCTG

TTGCAACTCACAGTCTGGGGCATCAAGCAGCTCCAGGCAAGAATCCTGGCTGTGGAAAGATA

CCTAAAGGATCAACAGCTCCTGGGGATTTGGGGTTGCTCTGGAAAACTCATTTGCACCACTG

CTGTGCCTTGGAATGCTAGTTGGAGTAATAAATCTCTGGAACAGATTTGGAATCACACGACC

TGGATGGAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGGCAAGTT

TGTGGAATTGGTTTAACATAACAAATTGGCTGTGGTATATAAAATTATTCATAATGATAGTA

-continued

GGAGGCTTGGTAGGTTTAAGAATAGTTTTTGCTGTACTTTCTATAGTGAATAGAGTTAGGCA

GGGATATTCACCATTATCGTTTCAGACCCACCTCCCAACCCCGAGGGGACCCGACGGGCCCG

AAGGAATAGAAGAAGAAGGTGGAGAGAGAGACAGAGACAGATCCATTCGATTAGTGAACGGA

TCTCGACGGTATCGATCTCGACACAAATGGCAGTATTCATCCACAATTTTAAAAGAAAAGGG

GGGATTGGGGGGTACAGTGCAGGGGAAAGAATAGTAGACATAATAGCAACAGACATACAAAC

TAAAGAATTACAAAAACAAATTACAAAAATTCAAAATTTTCGGGTTTATTACAGGGACAGCA

GAGATCCAGTTTGGGTCGAGGATATCGGATCGGAATTCTCTAGATGATCAGGATCCCTCGAG

CCCTTATCGATCACGAGACTAGCCTCGACTACTAGTGGAGATCCCCCGGGCTGCAGAGCCAG

AAGCACCATAAGGGACATGATAAGGGAGCCAGCAGACCTCTGATCTCTTCCTGAATGCTAAT

CTTAAACATCCTGAGGAAGAATGGGACTTCCATTTGGGGTGGGCCTATGATAGGGTAATAAG

ACAGTAGTGAATATCAAGCTACAAAAAGCCCCCTTTCAAATTCTTCTCAGTCCTAACTTTTC

ATACTAAGCCCAGTCCTTCCAAAGCAGACTGTGAAAGAGTGATAGTTCCGGGAGACTAGCAC

TGCAGATTCCGGGTCACTGTGAGTGGGGGAGGCAGGGAAGAAGGGCTCACAGGACAGTCAAA

CCATGCCCCCTGTTTTTCCTTCTTCAAGTAGACCTCTATAAGACAACAGAGACAACTAAGGC

TGAGTGGCCAGGCGAGGAGAAACCATCTCGCCGTAAAACATGGAAGGAACACTTCAGGGGAA

AGGTGGTATCTCTAAGCAAGAGAACTGAGTGGAGTCAAGGCTGAGAGATGCAGGATAAGCAA

ATGGGTAGTGAAAAGACATTCATGAGGACAGCTAAAACAATAAGTAATGTAAAATACAGCAT

AGCAAAACTTTAACCTCCAAATCAAGCCTCTACTTGAATCCTTTTCTGAGGGATGAATAAGG

CATAGGCATCAGGGGCTGTTGCCAATGTGCATTAGCTGTTTGCAGCCTCACCTTCTTTCATG

GAGTTTAAGATATAGTGTATTTTCCCAAGGTTTGAACTAGCTCTTCATTTCTTTATGTTTTA

AATGCACTGACCTCCCACATTCCCTTTTTAGTAAAATATTCAGAAATAATTTAAATACATCA

TTGCAATGAAAATAAATGTTTTTTATTAGGCAGAATCCAGATGCTCAAGGCCCTTCATAATA

TCCCCCAGTTTAGTAGTTGGACTTAGGGAACAAAGGAACCTTTAATAGAAATTGGACAGCAA

GAAAGCGAGCTTAGTGATACTTGTGGGCCAGGGCATTAGCCACACCAGCCACCACTTTCTGA

TAGGCAGCCTGCACTGGTGGGGTGAATTCTTTGCCAAAGTGATGGGCCAGCACACAGACCAG

CACGTTGCCCAGGAGCTGTGGGAGGAAGATAAGAGGTATGAACATGATTAGCAAAAGGGCCT

AGCTTGGACTCAGAATAATCCAGCCTTATCCCAACCATAAAATAAAAGCAGAATGGTAGCTG

GATTGTAGCTGCTATTAGCAATATGAAACCTCTTACATCAGTTACAATTTATATGCAGAAAT

ATTTATATGCAGAAATATTGCTATTGCCTTAACCCAGAAATTATCACTGTTATTCTTTAGAA

TGGTGCAAAGAGGCATGATACATTGTATCATTATTGCCCTGAAAGAAAGAGATTAGGGAAAG

TATTAGAAATAAGATAAACAAAAAAGTATATTAAAAGAAGAAAGCATTTTTTAAAATTACAA

ATGCAAAATTACCCTGATTTGGTCAATATGTGTACCCTGTTACTTCTCCCCTTCCTATGACA

TGAACTTAACCATAGAAAAGAAGGGGAAAGAAAACATCAAGGGTCCCATAGACTCACCCTGA

AGTTCTCAGGATCCACGTGCAGCTTGTCACAGTGCAGCTCACTCAGCTGGGCAAAGGTGCCC

TTGAGGTTGTCCAGGTGAGCCAGGCCATCACTAAAGGCACCGAGCACTTTCTTGCCATGAGC

CTTCACCTTAGGGTTGCCCATAACAGCATCAGGAGTGGACAGATCCCCAAAGGACTCAAAGA

ACCTCTGGGTCCAAGGGTAGACCACCAGCAGCCTAAGGGTGGGAAAATAGACCAATAGGCAG

AGAGAGTCAGTGCCTATCAGAAACCCAAGAGTCTTCTCTGTCTCCACATGCCCAGTTTCTAT

TGGTCTCCTTAAACCTGTCTTGTAACCTTGATACCAACCTGCCCAGGGCCTCACCACCAACG

GCATCCACGTTCACCTTGTCCCACAGGGCAGTAACGGCAGACTTCTCCTCAGGAGTCAGGTG

CACCATGGTGTCTGTTTGAGGTTGCTAGTGAACACAGTTGTGTCAGAAGCAAATGTAAGCAA

-continued

TAGATGGCTCTGCCCTGACTTTTATGCCCAGCCCTGGCTCCTGCCCTCCCTGCTCCTGGGAG

TAGATTGGCCAACCCTAGGGTGTGGCTCCACAGGGTGAGGTCTAAGTGATGACAGCCGTACC

TGTCCTTGGCTCTTCTGGCACTGGCTTAGGAGTTGGACTTCAAACCCTCAGCCCTCCCTCTA

AGATATATCTCTTGGCCCCATACCATCAGTACAAATTGCTACTAAAAACATCCTCCTTTGCA

AGTGTATTTACCCGACGCGTCGGCGATAAGCTTGATCCATCGATGTATTTTCTTCTTCTTGC

TGGTTTAGTCATGTTTTCTGGGAGCTTAGGGGCTTATTTTATTTTGTTTTGTTTTCTAATCA

ACAGAGATGGGCAAACCCATTATTTTTTTCTTTAGACTTGGGATGGTGATAGCTGGGCAGCG

TCAGAAACTGTGTGTGGATATAGATAAGAGCTCAGGACTATGCTGAGCTGTGATGAGGGAGG

GGCCTAGCTAAAGGCAGTGAGAGTCAGAATGCTCCTGCTATTGCCTTCTCAGTCCCCACGCT

TGGTTTCTACACACTACCTGCCTTGGCACAGTTTTTCTTTACTTTTACCTGACTGATGAAAC

AATTAATTGCTTACATAAACATGAGTGCTCTAGTTATAAATTCCAGTGTAAAAAACACCCTG

GTTTCGATATTCATCTTTTGAGCCTTTTATTTTGGTCAGATATTAATAAAGCCTGATTCTGC

CGCTTCTAGGTATAGAGGCCACCTGCAAGATAAATATTTGATTCACAATAACTAATCATTCT

ATGGCAATTGATAACAACAAATATATATATATATATATATATACGTTGTCACATTCTGTCTC

AGGCATCCATTTTCTTTATGATGCCGTTTGAGGTGGAGTTTTAGTCAGGTGGTCAGCTTCTC

CTTTTTTTTGCCATCTGCCCTGTAAGCATCCTGCTGGGGACCCAGATAGGAGTCATCACTCT

AGGCTGAGAACATCTGGGCACACACCCTAAGCCTCAGCATGACTCATCATGACTCAGCATTG

CTGTGCTTGAGCCAGAAGGTTTGCTTAGAAGGTTACACAGAACCAGAAGGCGGGGGTGGGGC

ACTGACCCCGACAGGGGCCTGGCCAGAACTGCTCATGCTTGGACTATGGGAGAGCCTGCCAG

CCTATAACCCATCTGGGCCCTGATAGCTGGTGGCCAGCCCTGACCCCACCCCACCCTCCCTG

GAACCTCTGATAGACACATCTGGCACACCAGCTCGCAAAGTCACCGTGAGGGTCTTGTGTTT

GCTGAGTCAAAATTCCTTGAAATCCAAGTCCTTAGAGACTCCTGCTCCCAAATTTACAGTCA

TAGACTTCTTCTTCTCCCCACATAGATCATCTCAGCAGGGTTCAGGAAGATAAAGGAGGATC

AAGGTCGAAGGTAGGAACTAAGGAAGAACACTGGGCAAGTGGATCCAGGTTGTCCAACGCTG

AAAGTAGGAATCTAAGCAAAAAAATGGAACCCAAAATATTCTACATAGTTTCCATGTCACAG

CCAGGGCTGGGCAGTCTCCTGTTATTTCTTTTAAAATAAATATATCATTTAAATGCATAAAT

AAGCAAACCCTGCTCGGGAATGGGAGGGAGAGTCTCTGGAGTCCACCCCTTCTCGGCCCTGG

CTCTGCAGATAGTGCTATCAAAGCCCTGACAGAGCCCTGCCCATTGCTGGGCCTTGGAGTGA

GTCAGCCTAGTAGAGAGGCAGGGCAAGCCATCTCATAGCTGCTGAGTGGGAGAGAGAAAAGG

GCTCATTTAGTTGTTTGTTTTTTGTCATTGTGACTATCAATAACATTCTCACTCTTTCATCA

GTAATCACTCAGGTTATTCTGTGACCAACAGACTGTGGGAAAAATCAGAGAAGGAGGCATCC

TCATGCTTACTAGCCTAAACTGAAATTGCTATAGCAGAGTGAACCAGAAGGTTTACAGATAT

TTTCGGCCTACTCGACCACGAGGGAATTCCGATAATCAACCTCTGGATTACAAAATTTGTGA

AAGATTGACTGGTATTCTTAACTATGTTGCTCCTTTTACGCTATGTGGATACGCTGCTTTAA

TGCCTTTGTATCATGCTATTGCTTCCCGTATGGCTTTCATTTTCTCCTCCTTGTATAAATCC

TGGTTGCTGTCTCTTTATGAGGAGTTGTGGCCCGTTGTCAGGCAACGTGGCGTGGTGTGCAC

TGTGTTTGCTGACGCAACCCCCACTGGTTGGGGCATTGCCACCACCTGTCAGCTCCTTTCCG

GGACTTTCGCTTTCCCCCTCCCTATTGCCACGGCGGAACTCATCGCCGCCTGCCTTGCCCGC

TGCTGGACAGGGGCTCGGCTGTTGGGCACTGACAATTCCGTGGTGTTGTCGGGGAAATCATC

GTCCTTTCCTTGGCTGCTCGCCTGTGTTGCCACCTGGATTCTGCGCGGGACGTCCTTCTGCT

-continued

ACGTCCCTTCGGCCCTCAATCCAGGGACCTTCCTTCCCGCGGCCTGCTGCCGGCTCTGCGGC

CTCTTCCGCGTCTTCGCCTTCGCCCTCAGACGAGTCGGATCTCCCTTTGGGCCGCCTCCCCG

CATCGATACCGTCGACCTCGAGACCTAGAAAAACATGGCCAATTCGAGCTCGGTACCTTTAA

GACCAATGACTTACAAGGCAGCTGTAGATCTTAGCCACTTTTTAAAAGAAAAGGGGGGACTG

GAAGGGCTAATTCACTCCCAACGAAGACAAGATCCCAGGGATGTACGTCCCTAACCCGCTAG

GGGGCAGCACCCAGGCCTGCACTGCCGCCTGCCGGCAGGGGTCCAGTCCTGCTTTTTGCTTG

TACTGGGTCTCTCTGGTTAGACCAGATCTGAGCCTGGGAGCTCTCTGGCTAACTAGGGAACC

CACTGCTTAAGCCTCAATAAAGCTTGCCTTGAGTGCTTCAAGTAGTGTGTGCCCGTCTGTTG

TGTGACTCTGGTAACTAGAGATCCCTCAGACCCTTTTAGTCAGTGTGGAAAATCTCTAGCAG

TAGTAGTTCATGTCATCTTATTATTCAGTATTTATAACTTGCAAAGAAATGAATATCAGAGA

GTGAGAGGAACTTGTTTATTGCAGCTTATAATGGTTACAAATAAAGCAATAGCATCACAAAT

TTCACAAATAAAGCATTTTTTTCACTGCATTCTAGTTGTGGTTTGTCCAAACTCATCAATGT

ATCTTATCATGTCTGGCTCTAGCTATCCCGCCCCTAACTCCGCCCATCCCGCCCCTAACTCC

GCCCAGTTCCGCCCATTCTCCGCCCCATGGCTGACTAATTTTTTTTATTTATGCAGAGGCCG

AGGCCGCCTCGGCCTCTGAGCTATTCCAGAAGTAGTGAGGAGGCTTTTTTGGAGGCCTAGGC

TTTTGCGTCGAGACGTACCCAATTCGCCCTATAGTGAGTCGTATTACGCGCGCTCACTGGCC

GTCGTTTTACAACGTCGTGACTGGGAAAACCCTGGCGTTACCCAACTTAATCGCCTTGCAGC

ACATCCCCCTTTCGCCAGCTGGCGTAATAGCGAAGAGGCCCGCACCGATCGCCCTTCCCAAC

AGTTGCGCAGCCTGAATGGCGAATGGCGCGACGCGCCCTGTAGCGGCGCATTAAGCGCGGCG

GGTGTGGTGGTTACGCGCAGCGTGACCGCTACACTTGCCAGCGCCCTAGCGCCCGCTCCTTT

CGCTTTCTTCCCTTCCTTTCTCGCCACGTTCGCCGGCTTTCCCCGTCAAGCTCTAAATCGGG

GGCTCCCTTTAGGGTTCCGATTTAGTGCTTTACGGCACCTCGACCCCAAAAAACTTGATTAG

GGTGATGGTTCACGTAGTGGGCCATCGCCCTGATAGACGGTTTTTCGCCCTTTGACGTTGGA

GTCCACGTTCTTTAATAGTGGACTCTTGTTCCAAACTGGAACAACACTCAACCCTATCTCGG

TCTATTCTTTTGATTTATAAGGGATTTTGCCGATTTCGGCCTATTGGTTAAAAAATGAGCTG

ATTTAACAAAAATTTAACGCGAATTTTAACAAAATATTAACGTTTACAATTTCCCAGGTGGC

ACTTTTCGGGGAAATGTGCGCGGAACCCCTATTTGTTTATTTTTCTAAATACATTCAAATAT

GTATCCGCTCATGAGACAATAACCCTGATAAATGCTTCAATAATATTGAAAAAGGAAGAGTA

TGAGTATTCAACATTTCCGTGTCGCCCTTATTCCCTTTTTTGCGGCATTTTGCCTTCCTGTT

TTTGCTCACCCAGAAACGCTGGTGAAAGTAAAAGATGCTGAAGATCAGTTGGGTGCACGAGT

GGGTTACATCGAACTGGATCTCAACAGCGGTAAGATCCTTGAGAGTTTTCGCCCCGAAGAAC

GTTTTCCAATGATGAGCACTTTTAAAGTTCTGCTATGTGGCGCGGTATTATCCCGTATTGAC

GCCGGGCAAGAGCAACTCGGTCGCCGCATACACTATTCTCAGAATGACTTGGTTGAGTACTC

ACCAGTCACAGAAAAGCATCTTACGGATGGCATGACAGTAAGAGAATTATGCAGTGCTGCCA

TAACCATGAGTGATAACACTGCGGCCAACTTACTTCTGACAACGATCGGAGGACCGAAGGAG

CTAACCGCTTTTTTGCACAACATGGGGGATCATGTAACTCGCCTTGATCGTTGGGAACCGGA

GCTGAATGAAGCCATACCAAACGACGAGCGTGACACCACGATGCCTGTAGCAATGGCAACAA

CGTTGCGCAAACTATTAACTGGCGAACTACTTACTCTAGCTTCCCGGCAACAATTAATAGAC

TGGATGGAGGCGGATAAAGTTGCAGGACCACTTCTGCGCTCGGCCCTTCCGGCTGGCTGGTT

TATTGCTGATAAATCTGGAGCCGGTGAGCGTGGGTCTCGCGGTATCATTGCAGCACTGGGGC

CAGATGGTAAGCCCTCCCGTATCGTAGTTATCTACACGACGGGGAGTCAGGCAACTATGGAT

-continued

GAACGAAATAGACAGATCGCTGAGATAGGTGCCTCACTGATTAAGCATTGGTAACTGTCAGA

CCAAGTTTACTCATATATACTTTAGATTGATTTAAAACTTCATTTTTAATTTAAAAGGATCT

AGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGT

AATCTGCTGCTTGCAAACAAAAAAACCACCGCTACCAGCGGTGGTTTGTTTGCCGGATCAAG

AGCTACCAACTCTTTTTCCGAAGGTAACTGGCTTCAGCAGAGCGCAGATACCAAATACTGTC

CTTCTAGTGTAGCCGTAGTTAGGCCACCACTTCAAGAACTCTGTAGCACCGCCTACATACCT

CGCTCTGCTAATCCTGTTACCAGTGGCTGCTGCCAGTGGCGATAAGTCGTGTCTTACCGGGT

TGGACTCAAGACGATAGTTACCGGATAAGGCGCAGCGGTCGGGCTGAACGGGGGGTTCGTGC

ACACAGCCCAGCTTGGAGCGAACGACCTACACCGAACTGAGATACCTACAGCGTGAGCTATG

AGAAAGCGCCACGCTTCCCGAAGGGAGAAAGGCGGACAGGTATCCGGTAAGCGGCAGGGTCG

GAACAGGAGAGCGCACGAGGGAGCTTCCAGGGGGAAACGCCTGGTATCTTTATAGTCCTGTC

GGGTTTCGCCACCTCTGACTTGAGCGTCGATTTTTGTGATGCTCGTCAGGGGGGCGGAGCCT

ATGGAAAAACGCCAGCAACGCGGCCATTTTTACGGTTCCTGGCCTTTTGCTGGCCTTTTGCT

CACATGTTCTTTCCTGCGTTATCCCCTGATTCTGTGGATAACCGTATTACCGCCTTTGAGTG

AGCTGATACCGCTCGCCGCAGCCGAACGACCGAGCGCAGCGAGTCAGTGAGCGAGGAAGCGG

AAGAGCGCCCAATACGCAAACCGCCTCTCCCCGCGCGTTGGCCGATTCATTAATGCAGCTGG

CACGACAGGTTTCCCGACTGGAAAGCGGGCAGTGA

Vector C (95 Sense) HS1.1

SEQ ID NO: 22

GTATTTTCTTCTTCTTGCTGGTTTAGTCATGTTTTCTGGGAGCTTAGGGGCTTATTTTATTT

TGTTTTGTTTTCTAATCAACAGAGATGGGCAAACCCATTATTTTTTTCTTTAGACTTGGGAT

GGTGATAGCTGGGCAGCGTCAGAAACTGTGTGTGGATATAGATAAGAGCTCAGGACTATGCT

GAGCTGTGATGAGGGAGGGGCCTAGCTAAAGGCAGTGAGAGTCAGAATGCTCCTGCTATTGC

CTTCTCAGTCCCCACGCTTGGTTTCTACACA

Vector C (95 Sense) HS1.2

SEQ ID NO: 23

CTACCTGCCTTGGCACAGTTTTTCTTTACTTTTACCTGACTGATGAAACAATTAATTGCTTA

CATAAACATGAGTGCTCTAGTTATAAATTCCAGTGTAAAAAACACCCTGGTTTCGATATTCA

TCTTTTGAGCCTTTTATTTTGGTCAGA

Vector C (95 Sense) HS2.1

SEQ ID NO: 24

TATTAATAAAGCCTGATTCTGCCGCTTCTAGGTATAGAGGCCACCTGCAAGATAAATATTTG

ATTCACAATAACTAATCATTCTATGGCAATTGATAACAACAAATATATATATATATATATAT

ATACGTT

Vector C (95 Sense) HS2.2

SEQ ID NO: 25

GTCACATTCTGTCTCAGGCATCCATTTTCTTTATGATGCCGTTTGAGGTGGAGTTTTAGTCA

GGTGGTCAGCTTCTCCTTTTTTTTGCCATCTGCCCTGTAAGCATCCTGCTGGGGACCCAGAT

AGGAGTCATCACTCTAGGCTGAGAACATCTGGGCACACACCCTAAGCCTCAGCATGACTCAT

CATGACTCAGCATTGCTGTGCTTGAGCCAGAAGGTTTGCTTAGAAGGTTACACAGAACCAGA

AGGCGGGGGTGGGGCACTGACCCCGACAGGGGCCTGGCCAGAACTGCTCATGCTTGGACTAT

GGGAG

-continued

Vector C (95 Sense) HS3.1

SEQ ID NO: 26

AGCCTGCCAGCCTATAACCCATCTGGGCCCTGATAGCTGGTGGCCAGCCCTGACCCCACCCC

ACCCTCCCTGGAACCTCTGATAGACACATCTGGCACACCAGCTCGCAAAGTCACCGTGAGGG

TCTTGTGTTTGCTGAGTCAAAATTCCTTGAAATCCAAGTCCTTAGAGACTCCTGCTCCCAAA

TTTACAGTCATAGACTTCTTC

Vector C (95 Sense) HS3.2

SEQ ID NO: 27

TTCTCCCCACATAGATCATCTCAGCAGGGTTCAGGAAGATAAAGGAGGATCAAGGTCGAAGG

TAGGAACTAAGGAAGAACACTGGGCAAGTGGATCCAGGTTGTCCAACGCTGAAAGTAGGAAT

CTAAGCA

Vector C (95 Sense) HS4.1

SEQ ID NO: 28

AAAAAATGGAACCCAAAATATTCTACATAGTTTCCATGTCACAGCCAGGGCTGGGCAGTCTC

CTGTTATTTCTTTTAAAATAAATATATCATTTAAATGCATAAATAAGCAAACCCTGCTCGGG

AATGGGAGGGAGAGTCTCTGGAGTCCACCCCTTCTCGGCCCTGGCTCTGCAGATAGTGCTAT

CAAAGCCCTGACAGAGCCCTGCCCATTGCTGGGCCTTGGAGTGAGTCAGCCTAGTAGAGAGG

CAGGGCAAGCCATCTCATAGCTGCTGAGTGGGAGAGAGAAAAGGGCTCATT

Vector C (95 Sense) HS5.1

SEQ ID NO: 29

TAGTTGTTTGTTTTTTGTCATTGTGACTATCAATAACATTCTCACTCTTTCATCAGTAATCA

CTCAGGTTATTCTGTGACCAACAGACTGTGGGAAAAATCAGAGAAGGAGGCATCCTCATGCT

TACTAGCCTAAACTGAAATTGCTATAGCAGAGTGAACCAGAAGGTTTACAGATATTTTC

Vector D (97.5 Sense)

SEQ ID NO: 30

GCGCAACGCAATTAATGTGAGTTAGCTCACTCATTAGGCACCCCAGGCTTTACACTTTATGC

TTCCGGCTCGTATGTTGTGTGGAATTGTGAGCGGATAACAATTTCACACAGGAAACAGCTAT

GACCATGATTACGCCAAGCGCGCAATTAACCCTCACTAAAGGGAACAAAAGCTGGAGCTGCA

AGCTTGGCCATTGCATACGTTGTATCCATATCATAATATGTACATTTATATTGGCTCATGTC

CAACATTACCGCCATGTTGACATTGATTATTGACTAGTTATTAATAGTAATCAATTACGGGG

TCATTAGTTCATAGCCCATATATGGAGTTCCGCGTTACATAACTTACGGTAAATGGCCCGCC

TGGCTGACCGCCCAACGACCCCCGCCCATTGACGTCAATAATGACGTATGTTCCCATAGTAA

CGCCAATAGGGACTTTCCATTGACGTCAATGGGTGGAGTATTTACGGTAAACTGCCCACTTG

GCAGTACATCAAGTGTATCATATGCCAAGTACGCCCCCTATTGACGTCAATGACGGTAAATG

GCCCGCCTGGCATTATGCCCAGTACATGACCTTATGGGACTTTCCTACTTGGCAGTACATCT

ACGTATTAGTCATCGCTATTACCATGGTGATGCGGTTTTGGCAGTACATCAATGGGCGTGGA

TAGCGGTTTGACTCACGGGGATTTCCAAGTCTCCACCCCATTGACGTCAATGGGAGTTTGTT

TTGGCACCAAAATCAACGGGACTTTCCAAAATGTCGTAACAACTCCGCCCCATTGACGCAAA

TGGGCGGTAGGCGTGTACGGTGGGAGGTCTATATAAGCAGAGCTCGTTTAGTGAACCGGGGT

CTCTCTGGTTAGACCAGATCTGAGCCTGGGAGCTCTCTGGCTAACTAGGGAACCCACTGCTT

AAGCCTCAATAAAGCTTGCCTTGAGTGCTTCAAGTAGTGTGTGCCCGTCTGTTGTGTGACTC

TGGTAACTAGAGATCCCTCAGACCCTTTTAGTCAGTGTGGAAAATCTCTAGCAGTGGCGCCC

GAACAGGGACTTGAAAGCGAAAGGGAAACCAGAGGAGCTCTCTCGACGCAGGACTCGGCTTG

CTGAAGCGCGCACGGCAAGAGGCGAGGGGCGGCGACTGGTGAGTACGCCAAAAATTTTGACT

AGCGGAGGCTAGAAGGAGAGAGATGGGTGCGAGAGCGTCAGTATTAAGCGGGGGAGAATTAG

-continued

ATCGCGATGGGAAAAAATTCGGTTAAGGCCAGGGGGAAAGAAAAAATATAAATTAAAACATA

TAGTATGGGCAAGCAGGGAGCTAGAACGATTCGCAGTTAATCCTGGCCTGTTAGAAACATCA

GAAGGCTGTAGACAAATACTGGGACAGCTACAACCATCCCTTCAGACAGGATCAGAAGAACT

TAGATCATTATATAATACAGTAGCAACCCTCTATTGTGTGCATCAAAGGATAGAGATAAAAG

ACACCAAGGAAGCTTTAGACAAGATAGAGGAAGAGCAAAACAAAAGTAAGACCACCGCACAG

CAAGCGGCCGCTGATCTTCAGACCTGGAGGAGGAGATATGAGGGACAATTGGAGAAGTGAAT

TATATAAATATAAAGTAGTAAAAATTGAACCATTAGGAGTAGCACCCACCAAGGCAAAGAGA

AGAGTGGTGCAGAGAGAAAAAAGAGCAGTGGGAATAGGAGCTTTGTTCCTTGGGTTCTTGGG

AGCAGCAGGAAGCACTATGGGCGCAGCGTCAATGACGCTGACGGTACAGGCCAGACAATTAT

TGTCTGGTATAGTGCAGCAGCAGAACAATTTGCTGAGGGCTATTGAGGCGCAACAGCATCTG

TTGCAACTCACAGTCTGGGGCATCAAGCAGCTCCAGGCAAGAATCCTGGCTGTGGAAAGATA

CCTAAAGGATCAACAGCTCCTGGGGATTTGGGGTTGCTCTGGAAAACTCATTTGCACCACTG

CTGTGCCTTGGAATGCTAGTTGGAGTAATAAATCTCTGGAACAGATTTGGAATCACACGACC

TGGATGGAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGGCAAGTT

TGTGGAATTGGTTTAACATAACAAATTGGCTGTGGTATATAAAATTATTCATAATGATAGTA

GGAGGCTTGGTAGGTTTAAGAATAGTTTTTGCTGTACTTTCTATAGTGAATAGAGTTAGGCA

GGGATATTCACCATTATCGTTTCAGACCCACCTCCCAACCCCGAGGGGACCCGACGGGCCCG

AAGGAATAGAAGAAGAAGGTGGAGAGAGAGACAGAGACAGATCCATTCGATTAGTGAACGGA

TCTCGACGGTATCGATCTCGACACAAATGGCAGTATTCATCCACAATTTTAAAAGAAAAGGG

GGGATTGGGGGGTACAGTGCAGGGGAAAGAATAGTAGACATAATAGCAACAGACATACAAAC

TAAAGAATTACAAAAACAAATTACAAAAATTCAAAATTTTCGGGTTTATTACAGGGACAGCA

GAGATCCAGTTTGGGTCGAGGATATCGGATCGGAATTCTCTAGATGATCAGGATCCCTCGAG

CCCTTATCGATCACGAGACTAGCCTCGACTACTAGTGGAGATCCCCCGGGCTGCAGAGCCAG

AAGCACCATAAGGGACATGATAAGGGAGCCAGCAGACCTCTGATCTCTTCCTGAATGCTAAT

CTTAAACATCCTGAGGAAGAATGGGACTTCCATTTGGGGTGGGCCTATGATAGGGTAATAAG

ACAGTAGTGAATATCAAGCTACAAAAAGCCCCCTTTCAAATTCTTCTCAGTCCTAACTTTTC

ATACTAAGCCCAGTCCTTCCAAAGCAGACTGTGAAAGAGTGATAGTTCCGGGAGACTAGCAC

TGCAGATTCCGGGTCACTGTGAGTGGGGGAGGCAGGGAAGAAGGGCTCACAGGACAGTCAAA

CCATGCCCCCTGTTTTTCCTTCTTCAAGTAGACCTCTATAAGACAACAGAGACAACTAAGGC

TGAGTGGCCAGGCGAGGAGAAACCATCTCGCCGTAAAACATGGAAGGAACACTTCAGGGGAA

AGGTGGTATCTCTAAGCAAGAGAACTGAGTGGAGTCAAGGCTGAGAGATGCAGGATAAGCAA

ATGGGTAGTGAAAAGACATTCATGAGGACAGCTAAAACAATAAGTAATGTAAAATACAGCAT

AGCAAAACTTTAACCTCCAAATCAAGCCTCTACTTGAATCCTTTTCTGAGGGATGAATAAGG

CATAGGCATCAGGGGCTGTTGCCAATGTGCATTAGCTGTTTGCAGCCTCACCTTCTTTCATG

GAGTTTAAGATATAGTGTATTTTCCCAAGGTTTGAACTAGCTCTTCATTTCTTTATGTTTTA

AATGCACTGACCTCCCACATTCCCTTTTTAGTAAAATATTCAGAAATAATTTAAATACATCA

TTGCAATGAAAATAAATGTTTTTTATTAGGCAGAATCCAGATGCTCAAGGCCCTTCATAATA

TCCCCCAGTTTAGTAGTTGGACTTAGGGAACAAAGGAACCTTTAATAGAAATTGGACAGCAA

GAAAGCGAGCTTAGTGATACTTGTGGGCCAGGGCATTAGCCACACCAGCCACCACTTTCTGA

TAGGCAGCCTGCACTGGTGGGGTGAATTCTTTGCCAAAGTGATGGGCCAGCACACAGACCAG

-continued

CACGTTGCCCAGGAGCTGTGGGAGGAAGATAAGAGGTATGAACATGATTAGCAAAAGGGCCT

AGCTTGGACTCAGAATAATCCAGCCTTATCCCAACCATAAAATAAAAGCAGAATGGTAGCTG

GATTGTAGCTGCTATTAGCAATATGAAACCTCTTACATCAGTTACAATTTATATGCAGAAAT

ATTTATATGCAGAAATATTGCTATTGCCTTAACCCAGAAATTATCACTGTTATTCTTTAGAA

TGGTGCAAAGAGGCATGATACATTGTATCATTATTGCCCTGAAAGAAAGAGATTAGGGAAAG

TATTAGAAATAAGATAAACAAAAAAGTATATTAAAAGAAGAAAGCATTTTTTAAAATTACAA

ATGCAAAATTACCCTGATTTGGTCAATATGTGTACCCTGTTACTTCTCCCCTTCCTATGACA

TGAACTTAACCATAGAAAAGAAGGGGAAAGAAAACATCAAGGGTCCCATAGACTCACCCTGA

AGTTCTCAGGATCCACGTGCAGCTTGTCACAGTGCAGCTCACTCAGCTGGGCAAAGGTGCCC

TTGAGGTTGTCCAGGTGAGCCAGGCCATCACTAAAGGCACCGAGCACTTTCTTGCCATGAGC

CTTCACCTTAGGGTTGCCCATAACAGCATCAGGAGTGGACAGATCCCCAAAGGACTCAAAGA

ACCTCTGGGTCCAAGGGTAGACCACCAGCAGCCTAAGGGTGGGAAAATAGACCAATAGGCAG

AGAGAGTCAGTGCCTATCAGAAACCCAAGAGTCTTCTCTGTCTCCACATGCCCAGTTTCTAT

TGGTCTCCTTAAACCTGTCTTGTAACCTTGATACCAACCTGCCCAGGGCCTCACCACCAACG

GCATCCACGTTCACCTTGTCCCACAGGGCAGTAACGGCAGACTTCTCCTCAGGAGTCAGGTG

CACCATGGTGTCTGTTTGAGGTTGCTAGTGAACACAGTTGTGTCAGAAGCAAATGTAAGCAA

TAGATGGCTCTGCCCTGACTTTTATGCCCAGCCCTGGCTCCTGCCCTCCCTGCTCCTGGGAG

TAGATTGGCCAACCCTAGGGTGTGGCTCCACAGGGTGAGGTCTAAGTGATGACAGCCGTACC

TGTCCTTGGCTCTTCTGGCACTGGCTTAGGAGTTGGACTTCAAACCCTCAGCCCTCCCTCTA

AGATATATCTCTTGGCCCCATACCATCAGTACAAATTGCTACTAAAAACATCCTCCTTTGCA

AGTGTATTTACCCGACGCGTCGGCGATAAGCTTGATCCATCGATGTTTAGTCATGTTTTCTG

GGAGCTTAGGGGCTTATTTTATTTTGTTTTGTTTTCTAATCAACAGAGATGGGCAAACCCAT

TATTTTTTTCTTTAGACTTGGGATGGTGATAGCTGGGCAGCGTCAGAAACTGTGTGTGGATA

TAGATAAGAGCTCAGGACTATGCTGAGCTGTGATGAGGGAGGGGCCTAGCTAAAGGCAGTGA

GAGTCAGAATGCTCCTGCTATTGCCTTCTACCTGCCTTGGCACAGTTTTTCTTTACTTTTAC

CTGACTGATGAAACAATTAATTGCTTACATAAACATGAGTGCTCTAGTTATAAATTCCAGTG

TAAAAAACACCCTGGTTTCGATATTCGTTTTAGTCAGGTGGTCAGCTTCTCCTTTTTTTTGC

CATCTGCCCTGTAAGCATCCTGCTGGGGACCCAGATAGGAGTCATCACTCTAGGCTGAGAAC

ATCTGGGCACACACCCTAAGCCTCAGCATGACTCATCATGACTCAGCATTGCTGTGCTTGAG

CCAGAAGGTTTGCTTAGAAGGTTACACAGAACCAGAAGGCGGGGGTGGGGCACTGACCCCGA

CAGGGGCCTGGCCAGAACTGCTCATGCTTGGACTATGAGCCTATAACCCATCTGGGCCCTGA

TAGCTGGTGGCCAGCCCTGACCCCACCCCACCCTCCCTGGAACCTCTGATAGACACATCTGG

CACACCAGCTCGCAAAGTCACCGTGAGGGTCTTGTGTTTGCTGAGTCAAAATTCCTTGAAAT

CCAAGTCCTTTTTTAAAATAAATATATCATTTAAATGCATAAATAAGCAAACCCTGCTCGGG

AATGGGAGGGAGAGTCTCTGGAGTCCACCCCTTCTCGGCCCTGGCTCTGCAGATAGTGCTAT

CAAAGCCCTGACAGAGCCCTGCCCATTGCTGGGCCTTGGAGTGAGTCAGCCTAGTAGAGAGG

CAGGGCAAGCCATCTCATAGCTGCTGAGTGGGAGAGACTATCAATAACATTCTCACTCTTTC

ATCAGTAATCACTCAGGTTATTCTGTGACCAACAGACTGTGGGAAAAATCAGAGAAGGAGGC

ATCCTCATGCTTACTAGCCTAAGGCCTACTCGACCACGAGGGAATTCCGATAATCAACCTCT

GGATTACAAAATTTGTGAAAGATTGACTGGTATTCTTAACTATGTTGCTCCTTTTACGCTAT

-continued

GTGGATACGCTGCTTTAATGCCTTTGTATCATGCTATTGCTTCCCGTATGGCTTTCATTTTC

TCCTCCTTGTATAAATCCTGGTTGCTGTCTCTTTATGAGGAGTTGTGGCCCGTTGTCAGGCA

ACGTGGCGTGGTGTGCACTGTGTTTGCTGACGCAACCCCCACTGGTTGGGGCATTGCCACCA

CCTGTCAGCTCCTTTCCGGGACTTTCGCTTTCCCCCTCCCTATTGCCACGGCGGAACTCATC

GCCGCCTGCCTTGCCCGCTGCTGGACAGGGGCTCGGCTGTTGGGCACTGACAATTCCGTGGT

GTTGTCGGGGAAATCATCGTCCTTTCCTTGGCTGCTCGCCTGTGTTGCCACCTGGATTCTGC

GCGGGACGTCCTTCTGCTACGTCCCTTCGGCCCTCAATCCAGCGGACCTTCCTTCCCGCGGC

CTGCTGCCGGCTCTGCGGCCTCTTCCGCGTCTTCGCCTTCGCCCTCAGACGAGTCGGATCTC

CCTTTGGGCCGCCTCCCCGCATCGATACCGTCGACCTCGAGACCTAGAAAAACATGGCCAAT

TCGAGCTCGGTACCTTTAAGACCAATGACTTACAAGGCAGCTGTAGATCTTAGCCACTTTTT

AAAAGAAAAGGGGGGACTGGAAGGGCTAATTCACTCCCAACGAAGACAAGATCCCAGGGATG

TACGTCCCTAACCCGCTAGGGGGCAGCACCCAGGCCTGCACTGCCGCCTGCCGGCAGGGGTC

CAGTCCTGCTTTTTGCTTGTACTGGGTCTCTCTGGTTAGACCAGATCTGAGCCTGGGAGCTC

TCTGGCTAACTAGGGAACCCACTGCTTAAGCCTCAATAAAGCTTGCCTTGAGTGCTTCAAGT

AGTGTGTGCCCGTCTGTTGTGTGACTCTGGTAACTAGAGATCCCTCAGACCCTTTTAGTCAG

TGTGGAAAATCTCTAGCAGTAGTAGTTCATGTCATCTTATTATTCAGTATTTATAACTTGCA

AAGAAATGAATATCAGAGAGTGAGAGGAACTTGTTTATTGCAGCTTATAATGGTTACAAATA

AAGCAATAGCATCACAAATTTCACAAATAAAGCATTTTTTTCACTGCATTCTAGTTGTGGTT

TGTCCAAACTCATCAATGTATCTTATCATGTCTGGCTCTAGCTATCCCGCCCCTAACTCCGC

CCATCCCGCCCCTAACTCCGCCCAGTTCCGCCCATTCTCCGCCCCATGGCTGACTAATTTTT

TTTATTTATGCAGAGGCCGAGGCCGCCTCGGCCTCTGAGCTATTCCAGAAGTAGTGAGGAGG

CTTTTTTGGAGGCCTAGGCTTTTGCGTCGAGACGTACCCAATTCGCCCTATAGTGAGTCGTA

TTACGCGCGCTCACTGGCCGTCGTTTTACAACGTCGTGACTGGGAAAACCCTGGCGTTACCC

AACTTAATCGCCTTGCAGCACATCCCCCTTTCGCCAGCTGGCGTAATAGCGAAGAGGCCCGC

ACCGATCGCCCTTCCCAACAGTTGCGCAGCCTGAATGGCGAATGGCGCGACGCGCCCTGTAG

CGGCGCATTAAGCGCGGCGGGTGTGGTGGTTACGCGCAGCGTGACCGCTACACTTGCCAGCG

CCCTAGCGCCCGCTCCTTTCGCTTTCTTCCCTTCCTTTCTCGCCACGTTCGCCGGCTTTCCC

CGTCAAGCTCTAAATCGGGGGCTCCCTTTAGGGTTCCGATTTAGTGCTTTACGGCACCTCGA

CCCCAAAAAACTTGATTAGGGTGATGGTTCACGTAGTGGGCCATCGCCCTGATAGACGGTTT

TTCGCCCTTTGACGTTGGAGTCCACGTTCTTTAATAGTGGACTCTTGTTCCAAACTGGAACA

ACACTCAACCCTATCTCGGTCTATTCTTTTGATTTATAAGGGATTTTGCCGATTTCGGCCTA

TTGGTTAAAAAATGAGCTGATTTAACAAAAATTTAACGCGAATTTTAACAAAATATTAACGT

TTACAATTTCCCAGGTGGCACTTTTCGGGGAAATGTGCGCGGAACCCCTATTTGTTTATTTT

TCTAAATACATTCAAATATGTATCCGCTCATGAGACAATAACCCTGATAAATGCTTCAATAA

TATTGAAAAAGGAAGAGTATGAGTATTCAACATTTCCGTGTCGCCCTTATTCCCTTTTTTGC

GGCATTTTGCCTTCCTGTTTTTGCTCACCCAGAAACGCTGGTGAAAGTAAAAGATGCTGAAG

ATCAGTTGGGTGCACGAGTGGGTTACATCGAACTGGATCTCAACAGCGGTAAGATCCTTGAG

AGTTTTCGCCCCGAAGAACGTTTTCCAATGATGAGCACTTTTAAAGTTCTGCTATGTGGCGC

GGTATTATCCCGTATTGACGCCGGGCAAGAGCAACTCGGTCGCCGCATACACTATTCTCAGA

ATGACTTGGTTGAGTACTCACCAGTCACAGAAAAGCATCTTACGGATGGCATGACAGTAAGA

GAATTATGCAGTGCTGCCATAACCATGAGTGATAACACTGCGGCCAACTTACTTCTGACAAC

GATCGGAGGACCGAAGGAGCTAACCGCTTTTTTGCACAACATGGGGGATCATGTAACTCGCC

TTGATCGTTGGGAACCGGAGCTGAATGAAGCCATACCAAACGACGAGCGTGACACCACGATG

CCTGTAGCAATGGCAACAACGTTGCGCAAACTATTAACTGGCGAACTACTTACTCTAGCTTC

CCGGCAACAATTAATAGACTGGATGGAGGCGGATAAAGTTGCAGGACCACTTCTGCGCTCGG

CCCTTCCGGCTGGCTGGTTTATTGCTGATAAATCTGGAGCCGGTGAGCGTGGGTCTCGCGGT

ATCATTGCAGCACTGGGGCCAGATGGTAAGCCCTCCCGTATCGTAGTTATCTACACGACGGG

GAGTCAGGCAACTATGGATGAACGAAATAGACAGATCGCTGAGATAGGTGCCTCACTGATTA

AGCATTGGTAACTGTCAGACCAAGTTTACTCATATATACTTTAGATTGATTTAAAACTTCAT

TTTTAATTTAAAAGGATCTAGGTGAAGATCCTTTTTGATAATCTCATGACCAAAATCCCTTA

ACGTGAGTTTTCGTTCCACTGAGCGTCAGACCCCGTAGAAAAGATCAAAGGATCTTCTTGAG

ATCCTTTTTTTCTGCGCGTAATCTGCTGCTTGCAAACAAAAAAACCACCGCTACCAGCGGTG

GTTTGTTTGCCGGATCAAGAGCTACCAACTCTTTTTCCGAAGGTAACTGGCTTCAGCAGAGC

GCAGATACCAAATACTGTCCTTCTAGTGTAGCCGTAGTTAGGCCACCACTTCAAGAACTCTG

TAGCACCGCCTACATACCTCGCTCTGCTAATCCTGTTACCAGTGGCTGCTGCCAGTGGCGAT

AAGTCGTGTCTTACCGGGTTGGACTCAAGACGATAGTTACCGGATAAGGCGCAGCGGTCGGG

CTGAACGGGGGGTTCGTGCACACAGCCCAGCTTGGAGCGAACGACCTACACCGAACTGAGAT

ACCTACAGCGTGAGCTATGAGAAAGCGCCACGCTTCCCGAAGGGAGAAAGGCGGACAGGTAT

CCGGTAAGCGGCAGGGTCGGAACAGGAGAGCGCACGAGGGAGCTTCCAGGGGGAAACGCCTG

GTATCTTTATAGTCCTGTCGGGTTTCGCCACCTCTGACTTGAGCGTCGATTTTTGTGATGCT

CGTCAGGGGGGCGGAGCCTATGGAAAAACGCCAGCAACGCGGCCATTTTTACGGTTCCTGGC

CTTTTGCTGGCCTTTTGCTCACATGTTCTTTCCTGCGTTATCCCCTGATTCTGTGGATAACC

GTATTACCGCCTTTGAGTGAGCTGATACCGCTCGCCGCAGCCGAACGACCGAGCGCAGCGAG

TCAGTGAGCGAGGAAGCGGAAGAGCGCCCAATACGCAAACCGCCTCTCCCCGCGCGTTGGCC

GATTCATTAATGCAGCTGGCACGACAGGTTTCCCGACTGGAAAGCGGGCAGTGA

Vector D (97.5 Sense) HS1.1

SEQ ID NO: 31

GTTTAGTCATGTTTTCTGGGAGCTTAGGGGCTTATTTTATTTTGTTTTGTTTTCTAATCAAC

AGAGATGGGCAAACCCATTATTTTTTTCTTTAGACTTGGGATGGTGATAGCTGGGCAGCGTC

AGAAACTGTGTGTGGATATAGATAAGAGCTCAGGACTATGCTGAGCTGTGATGAGGGAGGGG

CCTAGCTAAAGGCAGTGAGAGTCAGAATGCTCCTGCTATTGCCT

Vector D (97.5 Sense) HS1.2

SEQ ID NO: 32

TCTACCTGCCTTGGCACAGTTTTTCTTTACTTTTACCTGACTGATGAAACAATTAATTGCTT

ACATAAACATGAGTGCTCTAGTTATAAATTCCAGTGTAAAAAACACCCTGGTTTCGATATTC

Vector D (97.5 Sense) HS2.1

SEQ ID NO: 33

GTTTTAGTCAGGTGGTCAGCTTCTCCTTTTTTTTGCCATCTGCCCTGTAAGCATCCTGCTGG

GGACCCAGATAGGAGTCATCACTCTAGGCTGAGAACATCTGGGCACACACCCTAAGCCTCAG

CATGACTCATCATGACTCAGCATTGCTGTGCTTGAGCCAGAAGGTTTGCTTAGAAGGTTACA

CAGAACCAGAAGGCGGGGGTGGGGCACTGACCCCGACAGGGGCCTGGCCAGAACTGCTCATG

CTTGGACTATG

-continued

Vector D (97.5 Sense) HS3.1

SEQ ID NO: 34

AGCCTATAACCCATCTGGGCCCTGATAGCTGGTGGCCAGCCCTGACCCCACCCCACCCTCCC

TGGAACCTCTGATAGACACATCTGGCACACCAGCTCGCAAAGTCACCGTGAGGGTCTTGTGT

TTGCTGAGTCAAAATTCCTTGAAATCCAAGTCCTT

Vector D (97.5 Sense) HS4.1

SEQ ID NO: 35

TTTTAAAATAAATATATCATTTAAATGCATAAATAAGCAAACCCTGCTCGGGAATGGGAGGG

AGAGTCTCTGGAGTCCACCCCTTCTCGGCCCTGGCTCTGCAGATAGTGCTATCAAAGCCCTG

ACAGAGCCCTGCCCATTGCTGGGCCTTGGAGTGAGTCAGCCTAGTAGAGAGGCAGGGCAAGC

CATCTCATAGCTGCTGAGTGGGAGA

Vector D (97.5 Sense) HS5.1

SEQ ID NO: 36

GACTATCAATAACATTCTCACTCTTTCATCAGTAATCACTCAGGTTATTCTGTGACCAACAG

ACTGTGGGAAAAATCAGAGAAGGAGGCATCCTCATGCTTACTAGCCTAA

Vector E (98.5 Sense)

SEQ ID NO: 37

GCGCAACGCAATTAATGTGAGTTAGCTCACTCATTAGGCACCCCAGGCTTTACACTTTATGC

TTCCGGCTCGTATGTTGTGTGGAATTGTGAGCGGATAACAATTTCACACAGGAAACAGCTAT

GACCATGATTACGCCAAGCGCGCAATTAACCCTCACTAAAGGGAACAAAAGCTGGAGCTGCA

AGCTTGGCCATTGCATACGTTGTATCCATATCATAATATGTACATTTATATTGGCTCATGTC

CAACATTACCGCCATGTTGACATTGATTATTGACTAGTTATTAATAGTAATCAATTACGGGG

TCATTAGTTCATAGCCCATATATGGAGTTCCGCGTTACATAACTTACGGTAAATGGCCCGCC

TGGCTGACCGCCCAACGACCCCCGCCCATTGACGTCAATAATGACGTATGTTCCCATAGTAA

CGCCAATAGGGACTTTCCATTGACGTCAATGGGTGGAGTATTTACGGTAAACTGCCCACTTG

GCAGTACATCAAGTGTATCATATGCCAAGTACGCCCCCTATTGACGTCAATGACGGTAAATG

GCCCGCCTGGCATTATGCCCAGTACATGACCTTATGGGACTTTCCTACTTGGCAGTACATCT

ACGTATTAGTCATCGCTATTACCATGGTGATGCGGTTTTGGCAGTACATCAATGGGCGTGGA

TAGCGGTTTGACTCACGGGGATTTCCAAGTCTCCACCCCATTGACGTCAATGGGAGTTTGTT

TTGGCACCAAAATCAACGGGACTTTCCAAAATGTCGTAACAACTCCGCCCCATTGACGCAAA

TGGGCGGTAGGCGTGTACGGTGGGAGGTCTATATAAGCAGAGCTCGTTTAGTGAACCGGGGT

CTCTCTGGTTAGACCAGATCTGAGCCTGGGAGCTCTCTGGCTAACTAGGGAACCCACTGCTT

AAGCCTCAATAAAGCTTGCCTTGAGTGCTTCAAGTAGTGTGTGCCCGTCTGTTGTGTGACTC

TGGTAACTAGAGATCCCTCAGACCCTTTTAGTCAGTGTGGAAAATCTCTAGCAGTGGCGCCC

GAACAGGGACTTGAAAGCGAAAGGGAAACCAGAGGAGCTCTCTCGACGCAGGACTCGGCTTG

CTGAAGCGCGCACGGCAAGAGGCGAGGGGCGGCGACTGGTGAGTACGCCAAAAATTTTGACT

AGCGGAGGCTAGAAGGAGAGAGATGGGTGCGAGAGCGTCAGTATTAAGCGGGGGAGAATTAG

ATCGCGATGGGAAAAAATTCGGTTAAGGCCAGGGGGAAAGAAAAAATATAAATTAAAACATA

TAGTATGGGCAAGCAGGGAGCTAGAACGATTCGCAGTTAATCCTGGCCTGTTAGAAACATCA

GAAGGCTGTAGACAAATACTGGGACAGCTACAACCATCCCTTCAGACAGGATCAGAAGAACT

TAGATCATTATATAATACAGTAGCAACCCTCTATTGTGTGCATCAAAGGATAGAGATAAAAG

ACACCAAGGAAGCTTTAGACAAGATAGAGGAAGAGCAAAACAAAAGTAAGACCACCGCACAG

CAAGCGGCCGCTGATCTTCAGACCTGGAGGAGGAGATATGAGGGACAATTGGAGAAGTGAAT

TATATAAATATAAAGTAGTAAAAATTGAACCATTAGGAGTAGCACCCACCAAGGCAAAGAGA

-continued

AGAGTGGTGCAGAGAGAAAAAAGAGCAGTGGGAATAGGAGCTTTGTTCCTTGGGTTCTTGGG

AGCAGCAGGAAGCACTATGGGCGCAGCGTCAATGACGCTGACGGTACAGGCCAGACAATTAT

TGTCTGGTATAGTGCAGCAGCAGAACAATTTGCTGAGGGCTATTGAGGCGCAACAGCATCTG

TTGCAACTCACAGTCTGGGGCATCAAGCAGCTCCAGGCAAGAATCCTGGCTGTGGAAAGATA

CCTAAAGGATCAACAGCTCCTGGGGATTTGGGGTTGCTCTGGAAAACTCATTTGCACCACTG

CTGTGCCTTGGAATGCTAGTTGGAGTAATAAATCTCTGGAACAGATTTGGAATCACACGACC

TGGATGGAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGGCAAGTT

TGTGGAATTGGTTTAACATAACAAATTGGCTGTGGTATATAAAATTATTCATAATGATAGTA

GGAGGCTTGGTAGGTTTAAGAATAGTTTTTGCTGTACTTTCTATAGTGAATAGAGTTAGGCA

GGGATATTCACCATTATCGTTTCAGACCCACCTCCCAACCCCGAGGGGACCCGACGGCCCG

AAGGAATAGAAGAAGAAGGTGGAGAGAGAGACAGAGACAGATCCATTCGATTAGTGAACGGA

TCTCGACGGTATCGATCTCGACACAAATGGCAGTATTCATCCACAATTTTAAAAGAAAAGGG

GGGATTGGGGGGTACAGTGCAGGGGAAAGAATAGTAGACATAATAGCAACAGACATACAAAC

TAAAGAATTACAAAAACAAATTACAAAAATTCAAAATTTTCGGGTTTATTACAGGGACAGCA

GAGATCCAGTTTGGGTCGAGGATATCGGATCGGAATTCTCTAGATGATCAGGATCCCTCGAG

CCCTTATCGATCACGAGACTAGCCTCGACTACTAGTGGAGATCCCCCGGGCTGCAGAGCCAG

AAGCACCATAAGGGACATGATAAGGGAGCCAGCAGACCTCTGATCTCTTCCTGAATGCTAAT

CTTAAACATCCTGAGGAAGAATGGGACTTCCATTTGGGGTGGGCCTATGATAGGGTAATAAG

ACAGTAGTGAATATCAAGCTACAAAAAGCCCCCTTTCAAATTCTTCTCAGTCCTAACTTTTC

ATACTAAGCCCAGTCCTTCCAAAGCAGACTGTGAAAGAGTGATAGTTCCGGGAGACTAGCAC

TGCAGATTCCGGGTCACTGTGAGTGGGGGAGGCAGGGAAGAAGGGCTCACAGGACAGTCAAA

CCATGCCCCCTGTTTTTCCTTCTTCAAGTAGACCTCTATAAGACAACAGAGACAACTAAGGC

TGAGTGGCCAGGCGAGGAGAAACCATCTCGCCGTAAAACATGGAAGGAACACTTCAGGGGAA

AGGTGGTATCTCTAAGCAAGAGAACTGAGTGGAGTCAAGGCTGAGAGATGCAGGATAAGCAA

ATGGGTAGTGAAAAGACATTCATGAGGACAGCTAAAACAATAAGTAATGTAAAATACAGCAT

AGCAAAACTTTAACCTCCAAATCAAGCCTCTACTTGAATCCTTTTCTGAGGGATGAATAAGG

CATAGGCATCAGGGGCTGTTGCCAATGTGCATTAGCTGTTTGCAGCCTCACCTTCTTTCATG

GAGTTTAAGATATAGTGTATTTTCCCAAGGTTTGAACTAGCTCTTCATTTCTTTATGTTTTA

AATGCACTGACCTCCCACATTCCCTTTTTAGTAAAATATTCAGAAATAATTTAAATACATCA

TTGCAATGAAAATAAATGTTTTTTATTAGGCAGAATCCAGATGCTCAAGGCCCTTCATAATA

TCCCCCAGTTTAGTAGTTGGACTTAGGGAACAAAGGAACCTTTAATAGAAATTGGACAGCAA

GAAAGCGAGCTTAGTGATACTTGTGGGCCAGGGCATTAGCCACACCAGCCACCACTTTCTGA

TAGGCAGCCTGCACTGGTGGGGTGAATTCTTTGCCAAAGTGATGGGCCAGCACACAGACCAG

CACGTTGCCCAGGAGCTGTGGGAGGAAGATAAGAGGTATGAACATGATTAGCAAAAGGGCCT

AGCTTGGACTCAGAATAATCCAGCCTTATCCCAACCATAAAATAAAAGCAGAATGGTAGCTG

GATTGTAGCTGCTATTAGCAATATGAAACCTCTTACATCAGTTACAATTTATATGCAGAAAT

ATTTATATGCAGAAATATTGCTATTGCCTTAACCCAGAAATTATCACTGTTATTCTTTAGAA

TGGTGCAAAGAGGCATGATACATTGTATCATTATTGCCCTGAAAGAAAGAGATTAGGGAAAG

TATTAGAAATAAGATAAACAAAAAAGTATATTAAAAGAAGAAAGCATTTTTTAAAATTACAA

ATGCAAAATTACCCTGATTTGGTCAATATGTGTACCCTGTTACTTCTCCCCTTCCTATGACA

-continued

TGAACTTAACCATAGAAAAGAAGGGGAAAGAAAACATCAAGGGTCCCATAGACTCACCCTGA

AGTTCTCAGGATCCACGTGCAGCTTGTCACAGTGCAGCTCACTCAGCTGGGCAAAGGTGCCC

TTGAGGTTGTCCAGGTGAGCCAGGCCATCACTAAAGGCACCGAGCACTTTCTTGCCATGAGC

CTTCACCTTAGGGTTGCCCATAACAGCATCAGGAGTGGACAGATCCCCAAAGGACTCAAAGA

ACCTCTGGGTCCAAGGGTAGACCACCAGCAGCCTAAGGGTGGGAAAATAGACCAATAGGCAG

AGAGAGTCAGTGCCTATCAGAAACCCAAGAGTCTTCTCTGTCTCCACATGCCCAGTTTCTAT

TGGTCTCCTTAAACCTGTCTTGTAACCTTGATACCAACCTGCCCAGGGCCTCACCACCAACG

GCATCCACGTTCACCTTGTCCCACAGGGCAGTAACGGCAGACTTCTCCTCAGGAGTCAGGTG

CACCATGGTGTCTGTTTGAGGTTGCTAGTGAACACAGTTGTGTCAGAAGCAAATGTAAGCAA

TAGATGGCTCTGCCCTGACTTTTATGCCCAGCCCTGGCTCCTGCCCTCCCTGCTCCTGGGAG

TAGATTGGCCAACCCTAGGGTGTGGCTCCACAGGGTGAGGTCTAAGTGATGACAGCCGTACC

TGTCCTTGGCTCTTCTGGCACTGGCTTAGGAGTTGGACTTCAAACCCTCAGCCCTCCCTCTA

AGATATATCTCTTGGCCCCATACCATCAGTACAAATTGCTACTAAAAACATCCTCCTTTGCA

AGTGTATTTACCCGACGCGTCGGCGATAAGCTTGATCCATCGATATGTTTTCTGGGAGCTTA

GGGGCTTATTTTATTTTGTTTTGTTTTCTAATCAACAGAGATGGGCAAACCCATTATTTTTT

TCTTTAGACTTGGGATGGTGATAGCTGGGCAGCGTCAGAAACTGTGTGTGGATATAGATAAG

AGCTCAGGACTATGCTGAGCTGTGATGAGGGAGGGGCCTAGCTAAAGGCAGTGAGAGTCAGA

ATGCTCCTGCTATTGCCTTTTTTTTGCCATCTGCCCTGTAAGCATCCTGCTGGGGACCCAGA

TAGGAGTCATCACTCTAGGCTGAGAACATCTGGGCACACACCCTAAGCCTCAGCATGACTCA

TCATGACTCAGCATTGCTGTGCTTGAGCCAGAAGGTTTGCTTAGAAGGTTACACAGAACCAG

AAGGCGGGGGTGGGGCACTGACCCCGACAGGGGCCTGGCCAGAACTGCTCATGCTTGGACTA

TGCCACCCTCCCTGGAACCTCTGATAGACACATCTGGCACACCAGCTCGCAAAGTCACCGTG

AGGGTCTTGTGTTTGCTGAGTCAAAATTCCTTGAAATCCAAGTTAAATATATCATTTAAATG

CATAAATAAGCAAACCCTGCTCGGGAATGGGAGGGAGAGTCTCTGGAGTCCACCCCTTCTCG

GCCCTGGCTCTGCAGATAGTGCTATCAAAGCCCTGACAGAGCCCTGCCCATTGCTGGGCCTT

GGAGTGAGTCAGCCTAGTAGAGAGGCAGGGCAAGCCATCTCATAGCTGGACTATCAATAACA

TTCTCACTCTTTCATCAGTAATCACTCAGGTTATTCTGTGACCAACAGACTGTGGGAAAAAT

CAGAGAAGGAGGCATCCTCATGCTTACGGCCTACTCGACCACGAGGGAATTCCGATAATCAA

CCTCTGGATTACAAAATTTGTGAAAGATTGACTGGTATTCTTAACTATGTTGCTCCTTTTAC

GCTATGTGGATACGCTGCTTTAATGCCTTTGTATCATGCTATTGCTTCCCGTATGGCTTTCA

TTTTCTCCTCCTTGTATAAATCCTGGTTGCTGTCTCTTTATGAGGAGTTGTGGCCCGTTGTC

AGGCAACGTGGCGTGGTGTGCACTGTGTTTGCTGACGCAACCCCCACTGGTTGGGGCATTGC

CACCACCTGTCAGCTCCTTTCCGGGACTTTCGCTTTCCCCCTCCCTATTGCCACGGCGGAAC

TCATCGCCGCCTGCCTTGCCCGCTGCTGGACAGGGGCTCGGCTGTTGGGCACTGACAATTCC

GTGGTGTTGTCGGGGAAATCATCGTCCTTTCCTTGGCTGCTCGCCTGTGTTGCCACCTGGAT

TCTGCGCGGGACGTCCTTCTGCTACGTCCCTTCGGCCCTCAATCCAGCGGACCTTCCTTCCC

GCGGCCTGCTGCCGGCTCTGCGGCCTCTTCCGCGTCTTCGCCTTCGCCCTCAGACGAGTCGG

ATCTCCCTTTGGGCCGCCTCCCCGCATCGATACCGTCGACCTCGAGACCTAGAAAAACATGG

CCAATTCGAGCTCGGTACCTTTAAGACCAATGACTTACAAGGCAGCTGTAGATCTTAGCCAC

TTTTTAAAAGAAAAGGGGGGACTGGAAGGGCTAATTCACTCCCAACGAAGACAAGATCCCAG

-continued

GGATGTACGTCCCTAACCCGCTAGGGGGCAGCACCCAGGCCTGCACTGCCGCCTGCCGGCAG

GGGTCCAGTCCTGCTTTTTGCTTGTACTGGGTCTCTCTGGTTAGACCAGATCTGAGCCTGGG

AGCTCTCTGGCTAACTAGGGAACCCACTGCTTAAGCCTCAATAAAGCTTGCCTTGAGTGCTT

CAAGTAGTGTGTGCCCGTCTGTTGTGTGACTCTGGTAACTAGAGATCCCTCAGACCCTTTTA

GTCAGTGTGGAAAATCTCTAGCAGTAGTAGTTCATGTCATCTTATTATTCAGTATTTATAAC

TTGCAAAGAAATGAATATCAGAGAGTGAGAGGAACTTGTTTATTGCAGCTTATAATGGTTAC

AAATAAAGCAATAGCATCACAAATTTCACAAATAAAGCATTTTTTTCACTGCATTCTAGTTG

TGGTTTGTCCAAACTCATCAATGTATCTTATCATGTCTGGCTCTAGCTATCCCGCCCCTAAC

TCCGCCCATCCCGCCCCTAACTCCGCCCAGTTCCGCCCATTCTCCGCCCCATGGCTGACTAA

TTTTTTTTATTTATGCAGAGGCCGAGGCCGCCTCGGCCTCTGAGCTATTCCAGAAGTAGTGA

GGAGGCTTTTTTGGAGGCCTAGGCTTTTGCGTCGAGACGTACCCAATTCGCCCTATAGTGAG

TCGTATTACGCGCGCTCACTGGCCGTCGTTTTACAACGTCGTGACTGGGAAAACCCTGGCGT

TACCCAACTTAATCGCCTTGCAGCACATCCCCCTTTCGCCAGCTGGCGTAATAGCGAAGAGG

CCCGCACCGATCGCCCTTCCCAACAGTTGCGCAGCCTGAATGGCGAATGGCGCGACGCGCCC

TGTAGCGGCGCATTAAGCGCGGCGGGTGTGGTGGTTACGCGCAGCGTGACCGCTACACTTGC

CAGCGCCCTAGCGCCCGCTCCTTTCGCTTTCTTCCCTTCCTTTCTCGCCACGTTCGCCGGCT

TTCCCCGTCAAGCTCTAAATCGGGGGCTCCCTTTAGGGTTCCGATTTAGTGCTTTACGGCAC

CTCGACCCCAAAAAACTTGATTAGGGTGATGGTTCACGTAGTGGGCCATCGCCCTGATAGAC

GGTTTTTCGCCCTTTGACGTTGGAGTCCACGTTCTTTAATAGTGGACTCTTGTTCCAAACTG

GAACAACACTCAACCCTATCTCGGTCTATTCTTTTGATTTATAAGGGATTTTGCCGATTTCG

GCCTATTGGTTAAAAAATGAGCTGATTTAACAAAAATTTAACGCGAATTTTAACAAAATATT

AACGTTTACAATTTCCCAGGTGGCACTTTTCGGGGAAATGTGCGCGGAACCCCTATTTGTTT

ATTTTTCTAAATACATTCAAATATGTATCCGCTCATGAGACAATAACCCTGATAAATGCTTC

AATAATATTGAAAAAGGAAGAGTATGAGTATTCAACATTTCCGTGTCGCCCTTATTCCCTTT

TTTGCGGCATTTTGCCTTCCTGTTTTTGCTCACCCAGAAACGCTGGTGAAAGTAAAAGATGC

TGAAGATCAGTTGGGTGCACGAGTGGGTTACATCGAACTGGATCTCAACAGCGGTAAGATCC

TTGAGAGTTTTCGCCCCGAAGAACGTTTTCCAATGATGAGCACTTTTAAAGTTCTGCTATGT

GGCGCGGTATTATCCCGTATTGACGCCGGGCAAGAGCAACTCGGTCGCCGCATACACTATTC

TCAGAATGACTTGGTTGAGTACTCACCAGTCACAGAAAAGCATCTTACGGATGGCATGACAG

TAAGAGAATTATGCAGTGCTGCCATAACCATGAGTGATAACACTGCGGCCAACTTACTTCTG

ACAACGATCGGAGGACCGAAGGAGCTAACCGCTTTTTTGCACAACATGGGGGATCATGTAAC

TCGCCTTGATCGTTGGGAACCGGAGCTGAATGAAGCCATACCAAACGACGAGCGTGACACCA

CGATGCCTGTAGCAATGGCAACAACGTTGCGCAAACTATTAACTGGCGAACTACTTACTCTA

GCTTCCCGGCAACAATTAATAGACTGGATGGAGGCGGATAAAGTTGCAGGACCACTTCTGCG

CTCGGCCCTTCCGGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTAGTTATCTACACG

ACGGGGAGTCAGGCAACTATGGATGAACGAAATAGACAGATCGCTGAGATAGGTGCCTCACT

GATTAAGCATTGGTAACTGTCAGACCAAGTTTACTCATATATACTTTAGATTGATTTAAAAC

TTCATTTTTAATTTAAAAGGATCTAGGTGAAGATCCTTTTTGATAATCTCATGACCAAAATC

CCTTAACGTGAGTTTTCGTTCCACTGAGCGTCAGACCCCGTAGAAAAGATCAAAGGATCTTC

TTGAGATCCTTTTTTTCTGCGCGTAATCTGCTGCTTGCAAACAAAAAAACCACCGCTACCAG

-continued

CGGTGGTTTGTTTGCCGGATCAAGAGCTACCAACTCTTTTTCCGAAGGTAACTGGCTTCAGC

AGAGCGCAGATACCAAATACTGTCCTTCTAGTGTAGCCGTAGTTAGGCCACCACTTCAAGAA

CTCTGTAGCACCGCCTACATACCTCGCTCTGCTAATCCTGTTACCAGTGGCTGCTGCCAGTG

GCGATAAGTCGTGTCTTACCGGGTTGGACTCAAGACGATAGTTACCGGATAAGGCGCAGCGG

TCGGGCTGAACGGGGGGTTCGTGCACACAGCCCAGCTTGGAGCGAACGACCTACACCGAACT

GAGATACCTACAGCGTGAGCTATGAGAAAGCGCCACGCTTCCCGAAGGGAGAAAGGCGGACA

GGTATCCGGTAAGCGGCAGGGTCGGAACAGGAGAGCGCACGAGGGAGCTTCCAGGGGGAAAC

GCCTGGTATCTTTATAGTCCTGTCGGGTTTCGCCACCTCTGACTTGAGCGTCGATTTTTGTG

ATGCTCGTCAGGGGGGCGGAGCCTATGGAAAAACGCCAGCAACGCGGCCATTTTTACGGTTC

CTGGCCTTTTGCTGGCCTTTTGCTCACATGTTCTTTCCTGCGTTATCCCCTGATTCTGTGGA

TAACCGTATTACCGCCTTTGAGTGAGCTGATACCGCTCGCCGCAGCCGAACGACCGAGCGCA

GCGAGTCAGTGAGCGAGGAAGCGGAAGAGCGCCCAATACGCAAACCGCCTCTCCCCGCGCGT

TGGCCGATTCATTAATGCAGCTGGCACGACAGGTTTCCCGACTGGAAAGCGGGCAGTGA

Vector E (98.5 Sense) HS1.1

SEQ ID NO: 38

ATGTTTTCTGGGAGCTTAGGGGCTTATTTTATTTTGTTTTGTTTTCTAATCAACAGAGATGG

GCAAACCCATTATTTTTTTCTTTAGACTTGGGATGGTGATAGCTGGGCAGCGTCAGAAACTG

TGTGTGGATATAGATAAGAGCTCAGGACTATGCTGAGCTGTGATGAGGGAGGGGCCTAGCTA

AAGGCAGTGAGAGTCAGAATGCTCCTGCTATTG

Vector E (98.5 Sense) HS2.1

SEQ ID NO: 39

CCTTTTTTTTGCCATCTGCCCTGTAAGCATCCTGCTGGGGACCCAGATAGGAGTCATCACTC

TAGGCTGAGAACATCTGGGCACACACCCTAAGCCTCAGCATGACTCATCATGACTCAGCATT

GCTGTGCTTGAGCCAGAAGGTTTGCTTAGAAGGTTACACAGAACCAGAAGGCGGGGGTGGGG

CACTGACCCCGACAGGGGCCTGGCCAGAACTGCTCATGCTTGGACTATG

Vector E (98.5 Sense) HS3.1

SEQ ID NO: 40

CCACCCTCCCTGGAACCTCTGATAGACACATCTGGCACACCAGCTCGCAAAGTCACCGTGAG

GGTCTTGTGTTTGCTGAGTCAAAATTCCTTGAAATCCAAG

Vector E (98.5 Sense) HS4.1

SEQ ID NO: 41

TTAAATATATCATTTAAATGCATAAATAAGCAAACCCTGCTCGGGAATGGGAGGGAGAGTCT

CTGGAGTCCACCCCTTCTCGGCCCTGGCTCTGCAGATAGTGCTATCAAAGCCCTGACAGAGC

CCTGCCCATTGCTGGGCCTTGGAGTGAGTCAGCCTAGTAGAGAGGCAGGGCAAGCCATCTCA

TAGCTG

Vector E (98.5 Sense) HS5.1

SEQ ID NO: 42

GACTATCAATAACATTCTCACTCTTTCATCAGTAATCACTCAGGTTATTCTGTGACCAACAG

ACTGTGGGAAAAATCAGAGAAGGAGGCATCCTCATGCTTAC

What is claimed is:

1. A recombinant lentiviral vector (LV) comprising: an expression cassette comprising a nucleic acid construct comprising:

(a) a human β-globin locus control region (LCR) sequence selected from the group consisting of:

(i) a sequence consisting of reduced length HS sequences set forth in SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10;

(ii) a sequence consisting of reduced length HS sequences set forth in SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20;

(iii) a sequence consisting of reduced length HS sequences set forth in SEQ ID NO: 22, SEQ ID NO: 23, SEQ ID NO: 24, SEQ ID NO: 25, SEQ ID NO: 26, SEQ ID NO: 27, SEQ ID NO: 28, and SEQ ID NO: 29;

(iv) a sequence consisting of reduced length HS sequences set forth in SEQ ID NO: 31, SEQ ID NO: 32, SEQ ID NO: 33, SEQ ID NO: 34, SEQ ID NO: 35, and SEQ ID NO: 36; or (v) a sequence consisting of reduced length HS sequences set forth in SEQ ID NO: 38, SEQ ID NO: 39, SEQ ID NO: 40, SEQ ID NO: 41, and SEQ ID NO: 42; and (b) a heterologous gene to be expressed by said construct operably linked to said human β-globin LCR sequence; and wherein said LV is a TAT-independent and self-inactivating (SIN) lentiviral vector.

2. The vector of claim 1, wherein said human β-globin locus control region (LCR consists of the reduced length HS sequences consisting of the sequences set forth in SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

3. The vector of claim 1, wherein said human β-globin locus control region (LCR consists of the reduced length HS sequences consisting of the sequences set forth in SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

4. The vector of claim 1, wherein said human β-globin locus control region (LCR consists of the reduced length HS sequences consisting of the sequences set forth in SEQ ID NO: 22, SEQ ID NO: 23, SEQ ID NO: 24, SEQ ID NO: 25, SEQ ID NO: 26, SEQ ID NO: 27, SEQ ID NO: 28, and SEQ ID NO: 29.

5. The vector of claim 1, wherein said human β-globin locus control region (LCR consists of the reduced length HS sequences consisting of the sequences set forth in SEQ ID NO: 31, SEQ ID NO: 32, SEQ ID NO: 33, SEQ ID NO: 34, SEQ ID NO: 35, and SEQ ID NO: 36.

6. The vector of claim 1, wherein said human β-globin locus control region (LCR consists of the reduced length HS sequences consisting of the sequences set forth in SEQ ID NO: 38, SEQ ID NO: 39, SEQ ID NO: 40, SEQ ID NO: 41, and SEQ ID NO: 42.

7. The vector of claim 1, wherein:

said heterologous gene comprises a recombinant human β-globin gene encoding a β-globin polypeptide; or said heterologous gene comprises a wild-type β-globin gene; or said heterologous gene comprises a recombinant human β-globin gene that comprises an anti-sickling human β-globin gene encoding an anti-sickling β-globin polypeptide.

8. The vector of claim 7, wherein said anti-sickling human β-globin gene encoding an anti-sickling β-globin polypeptide comprises one or more mutations selected from the group consisting of Gly16Asp, Glu22Ala, and Thr87Gln.

9. The vector of claim 1, wherein said vector comprises a human Ankyrin insulator element; and/or said vector comprises a ψ region vector genome packaging signal; and/or said vector comprises a 5' LTR that comprises a CMV enhancer/promoter; and/or said vector comprises a Rev Responsive Element (RRE); and/or said vector comprises a central polypurine tract; and/or said vector comprises a post-translational regulatory element.

10. The vector of claim 1, wherein: said vector comprises the nucleic acid sequence set forth in SEQ ID NO: 1; or said vector comprises the nucleic acid sequence set forth in SEQ ID NO: 11; or said vector comprises the nucleic acid sequence set forth in SEQ ID NO: 21; or said vector comprises the nucleic acid sequence set forth in SEQ ID NO: 30; or said vector comprises the nucleic acid sequence set forth in SEQ ID NO: 37.

11. A host cell transduced with a vector of claim 1.

12. The host cell of claim 11, wherein the cell is a stem cell.

13. The host cell of claim 12, wherein said cell is a stem cell derived from bone marrow, or from umbilical cord blood, or from peripheral blood.

14. The host cell of claim 11, wherein the cell is a human hematopoietic progenitor cell.

15. A method of treating a hemoglobinopathy in a subject, said method comprising:

transducing a stem cell and/or progenitor cell from said subject with a vector of claim 1, wherein said heterologous gene comprises an anti-sickling human β-globin gene encoding an anti-sickling β-globin polypeptide; and transplanting said transduced cell or cells derived therefrom into said subject, wherein said cells or derivatives therefrom express said anti-sickling human β-globin polypeptide.

16. The method of claim 15, wherein said hemoglobinopathy is sickle cell disease or β-thalassemia.

* * * * *

SEQUENCE LISTING

<160> NUMBER OF SEQ ID NOS: 42

<210> SEQ ID NO 1
<211> LENGTH: 12739
<212> TYPE: DNA
<213> ORGANISM: Artificial
<220> FEATURE:
<223> OTHER INFORMATION: Lentiviral vector

<400> SEQUENCE: 1

```
gcgcaacgca attaatgtga gttagctcac tcattaggca ccccaggctt tacactttat     60

gcttccggct cgtatgttgt gtggaattgt gagcggataa caatttcaca caggaaacag    120

ctatgaccat gattacgcca agcgcgcaat taaccctcac taaagggaac aaaagctgga    180

gctgcaagct tggccattgc atacgttgta tccatatcat aatatgtaca tttatattgg    240

ctcatgtcca acattaccgc catgttgaca ttgattattg actagttatt aatagtaatc    300

aattacgggg tcattagttc atagcccata tatggagttc cgcgttacat aacttacggt    360

aaatggcccg cctggctgac cgcccaacga cccccgccca ttgacgtcaa taatgacgta    420

tgttcccata gtaacgccaa tagggacttt ccattgacgt caatgggtgg agtatttacg    480

gtaaactgcc cacttggcag tacatcaagt gtatcatatg ccaagtacgc cccctattga    540

cgtcaatgac ggtaaatggc ccgcctggca ttatgcccag tacatgacct tatgggactt    600

tcctacttgg cagtacatct acgtattagt catcgctatt accatggtga tgcggttttg    660

gcagtacatc aatgggcgtg gatagcggtt tgactcacgg ggatttccaa gtctccaccc    720

cattgacgtc aatgggagtt tgttttggca ccaaaatcaa cgggactttc caaaatgtcg    780

taacaactcc gccccattga cgcaaatggg cggtaggcgt gtacggtggg aggtctatat    840

aagcagagct cgtttagtga accggggtct ctctggttag accagatctg agcctgggag    900

ctctctggct aactagggaa cccactgctt aagcctcaat aaagcttgcc ttgagtgctt    960

caagtagtgt gtgcccgtct gttgtgtgac tctggtaact agagatccct cagacccttt   1020

tagtcagtgt ggaaaatctc tagcagtggc gcccgaacag ggacttgaaa gcgaaaggga   1080

aaccagagga gctctctcga cgcaggactc ggcttgctga agcgcgcacg gcaagaggcg   1140

aggggcggcg actggtgagt acgccaaaaa ttttgactag cggaggctag aaggagagag   1200

atgggtgcga gagcgtcagt attaagcggg ggagaattag atcgcgatgg gaaaaaattc   1260

ggttaaggcc agggggaaag aaaaaatata aattaaaaca tatagtatgg gcaagcaggg   1320

agctagaacg attcgcagtt aatcctggcc tgttagaaac atcagaaggc tgtagacaaa   1380

tactgggaca gctacaacca tcccttcaga caggatcaga agaacttaga tcattatata   1440

atacagtagc aaccctctat tgtgtgcatc aaaggataga gataaaagac accaaggaag   1500

ctttagacaa gatagaggaa gagcaaaaca aaagtaagac caccgcacag caagcggccg   1560

ctgatcttca gacctggagg aggagatatg agggacaatt ggagaagtga attatataaa   1620

tataaagtag taaaaattga accattagga gtagcaccca ccaaggcaaa gagaagagtg   1680

gtgcagagag aaaaaagagc agtgggaata ggagctttgt tccttgggtt cttgggagca   1740

gcaggaagca ctatgggcgc agcgtcaatg acgctgacgg tacaggccag acaattattg   1800

tctggtatag tgcagcagca gaacaatttg ctgagggcta ttgaggcgca acagcatctg   1860

ttgcaactca cagtctgggg catcaagcag ctccaggcaa gaatcctggc tgtggaaaga   1920

tacctaaagg atcaacagct cctggggatt tggggttgct ctggaaaact catttgcacc   1980

actgctgtgc cttggaatgc tagttggagt aataaatctc tggaacagat ttggaatcac   2040

acgacctgga tggagtggga cagagaaatt aacaattaca caagcttaat acactcctta   2100

attgaagaat cgcaaaacca gcaagaaaag aatgaacaag aattattgga attagataaa   2160

tgggcaagtt tgtggaattg gtttaacata acaaattggc tgtggtatat aaaattattc   2220
```

```
ataatgatag taggaggctt ggtaggttta agaatagttt ttgctgtact ttctatagtg   2280
aatagagtta ggcagggata ttcaccatta tcgtttcaga cccacctccc aaccccgagg   2340
ggacccgacg ggcccgaagg aatagaagaa gaaggtggag agagagacag agacagatcc   2400
attcgattag tgaacggatc tcgacggtat cgatctcgac acaaatggca gtattcatcc   2460
acaattttaa aagaaaaggg gggattgggg ggtacagtgc aggggaaaga atagtagaca   2520
taatagcaac agacatacaa actaaagaat tacaaaaaca aattacaaaa attcaaaatt   2580
ttcgggttta ttacagggac agcagagatc cagtttgggt cgaggatatc ggatcggaat   2640
tctctagatg atcaggatcc ctcgagccct tatcgatcac gagactagcc tcgactacta   2700
gtggagatcc cccgggctgc agagccagaa gcaccataag ggacatgata agggagccag   2760
cagacctctg atctcttcct gaatgctaat cttaaacatc ctgaggaaga atgggacttc   2820
catttggggt gggcctatga tagggtaata agacagtagt gaatatcaag ctacaaaaag   2880
ccccctttca aattcttctc agtcctaact tttcatacta agcccagtcc ttccaaagca   2940
gactgtgaaa gagtgatagt tccgggagac tagcactgca gattccgggt cactgtgagt   3000
gggggaggca gggaagaagg gctcacagga cagtcaaacc atgccccctg tttttccttc   3060
ttcaagtaga cctctataag acaacagaga caactaaggc tgagtggcca ggcgaggaga   3120
aaccatctcg ccgtaaaaca tggaaggaac acttcagggg aaaggtggta tctctaagca   3180
agagaactga gtggagtcaa ggctgagaga tgcaggataa gcaaatgggt agtgaaaaga   3240
cattcatgag gacagctaaa acaataagta atgtaaaata cagcatagca aaactttaac   3300
ctccaaatca agcctctact tgaatccttt tctgagggat gaataaggca taggcatcag   3360
gggctgttgc caatgtgcat tagctgtttg cagcctcacc ttctttcatg gagtttaaga   3420
tatagtgtat tttcccaagg tttgaactag ctcttcattt ctttatgttt taaatgcact   3480
gacctcccac attccctttt tagtaaaata ttcagaaata atttaaatac atcattgcaa   3540
tgaaaataaa tgtttttttat taggcagaat ccagatgctc aaggcccttc ataatatccc   3600
ccagtttagt agttggactt agggaacaaa ggaaccttta atagaaattg gacagcaaga   3660
aagcgagctt agtgatactt gtgggccagg gcattagcca caccagccac cactttctga   3720
taggcagcct gcactggtgg ggtgaattct ttgccaaagt gatgggccag cacacagacc   3780
agcacgttgc ccaggagctg tgggaggaag ataagaggta tgaacatgat tagcaaaagg   3840
gcctagcttg gactcagaat aatccagcct tatcccaacc ataaaataaa agcagaatgg   3900
tagctggatt gtagctgcta ttagcaatat gaaacctctt acatcagtta caatttatat   3960
gcagaaatat ttatatgcag aaatattgct attgccttaa cccagaaatt atcactgtta   4020
ttctttagaa tggtgcaaag aggcatgata cattgtatca ttattgccct gaaagaaaga   4080
gattagggaa agtattagaa ataagataaa caaaaaagta tattaaaaga agaaagcatt   4140
ttttaaaatt acaaatgcaa aattaccctg atttggtcaa tatgtgtacc ctgttacttc   4200
tccccttcct atgacatgaa cttaaccata gaaaagaagg ggaaagaaaa catcaagggt   4260
cccatagact caccctgaag ttctcaggat ccacgtgcag cttgtcacag tgcagctcac   4320
tcagctgggc aaaggtgccc ttgaggttgt ccaggtgagc caggccatca ctaaaggcac   4380
cgagcacttt cttgccatga gccttcacct tagggttgcc cataacagca tcaggagtgg   4440
acagatcccc aaaggactca aagaacctct gggtccaagg gtagaccacc agcagcctaa   4500
gggtgggaaa atagaccaat aggcagagag agtcagtgcc tatcagaaac ccaagagtct   4560
tctctgtctc cacatgccca gtttctattg gtctccttaa acctgtcttg taaccttgat   4620
```

```
accaacctgc ccagggcctc accaccaacg gcatccacgt tcaccttgtc ccacagggca   4680
gtaacggcag acttctcctc aggagtcagg tgcaccatgg tgtctgtttg aggttgctag   4740
tgaacacagt tgtgtcagaa gcaaatgtaa gcaatagatg gctctgccct gacttttatg   4800
cccagccctg gctcctgccc tccctgctcc tgggagtaga ttggccaacc ctagggtgtg   4860
gctccacagg gtgaggtcta agtgatgaca gccgtacctg tccttggctc ttctggcact   4920
ggcttaggag ttggacttca aaccctcagc cctccctcta agatatatct cttggcccca   4980
taccatcagt acaaattgct actaaaaaca tcctcctttg caagtgtatt tacccgacgc   5040
gtcggcgata agcttgatcc atcgattatt gaggctaagg catctgtgaa ggaaagaaac   5100
atctcctcta aaccactatg ctgctagagc ctcttttctg tactcaagcc tcattcagac   5160
actagtgtca ccagtctcct catataccta ttgtattttc ttcttcttgc tggtttagtc   5220
atgttttctg ggagcttagg ggcttatttt attttgtttt gttttctaat caacagagat   5280
gggcaaaccc attatttttt tctttagact tgggatggtg atagctgggc agcgtcagaa   5340
actgtgtgtg gatatagata agagctcagg actatgctga gctgtgatga gggaggggcc   5400
tagctaaagg cagtgagagt cagaatgctc ctgctattgc cttctcagtc cccacgcttg   5460
gtttctacac aagtagatac atagaaaagg ctataggttc atccttccca tgaagatgga   5520
tgaataagcc atatctgaca cctatgaaat aatgtttact ttagtggcat attgcattag   5580
gctacctgcc ttggcacagt ttttctttac ttttacctga ctgatgaaac aattaattgc   5640
ttacataaac atgagtgctc tagttataaa ttccagtgta aaaaacaccc tggtttcgat   5700
attcatcttt tgagcctttt attttggtca gaacaagttt tcaagagcaa atctcagcct   5760
acaaaacaaa tgagtccaat tctagaactc tttgtgtgtg catagcagtg gatgtgtcag   5820
catacatcct tttaattata gttgtatatg tgtttgactg ctcattcatt cattcaaaat   5880
tgtaaaattg ctaagaatac agcacaaaaa cagaatagag gaataaagtt cctgttttca   5940
tggacttgat agtggaaaga gcttgacatt aaataagcaa atgaaacatg ttatatacca   6000
atgagattag gtgctatgga gaaaaaaaaa aaactgaaat gaaggccaga gtgtgattag   6060
gacagggtga aagggtatcg ctactttaag tagtatggca ggaaagtcct cactataaag   6120
ttaacacctg agagagtacc catagatgat gaggaaccca tttatatgaa actatgatta   6180
attcctcagg accatctaca taatttctag gcccaatata aaatgaaaat gaatagcccc   6240
tttgtcaaaa attaaggatt tcatgtcagg aacagcaagg atgttaaacc aagcatgggg   6300
ccatcaagct atatctgcta ttcatgatac gaaaaaataa agagtattct agttatttag   6360
ccacatattt caagtttagt ctgatatcac cctttaaaca ctgccactca acctaaaaca   6420
atgctagtct ggccttttgc cacctagctg tccaggggtg ccttaaaatg gcaaacaagg   6480
tttgttttct tttcctgttt tcatgccttc ctcttccata tccttgtttc atattaatac   6540
atgtgtatag atcctaaaaa tctatacaca tgtattaata aagcctgatt ctgccgcttc   6600
taggtataga ggccacctgc aagataaata tttgattcac aataactaat cattctatgg   6660
caattgataa caacaaatat atatatatat atatatatac gtgtatgtgt atatatatat   6720
atatatatat tcaggaaata atatattcta gaatatgtca cattctgtct caggcatcca   6780
ttttctttat gatgccgttt gaggtggagt tttagtcagg tggtcagctt ctcctttttt   6840
ttgccatctg ccctgtaagc atcctgctgg ggacccagat aggagtcatc actctaggct   6900
gagaacatct gggcacacac cctaagcctc agcatgactc atcatgactc agcattgctg   6960
```

```
tgcttgagcc agaaggtttg cttagaaggt tacacagaac cagaaggcgg gggtggggca   7020
ctgaccccga caggggcctg gccagaactg ctcatgcttg gactatggga ggtcactaat   7080
ggagacacac agaaatgtaa caggccctct actcatggtc tatctctcct ggctcctggg   7140
agtcatggac tccacccagc accaccaacc tgacctaacc acctatctga gcctgccagc   7200
ctataaccca tctgggccct gatagctggt ggccagccct gaccccaccc caccctccct   7260
ggaacctctg atagacacat ctggcacacc agctcgcaaa gtcaccgtga gggtcttgtg   7320
tttgctgagt caaaattcct tgaaatccaa gtccttagag actcctgctc ccaaatttac   7380
agtcatagac ttcttcatgg ctgtctcctt tatccacaga atgattcctt tgcttcattg   7440
ccccatccat ctgatcctcc tcatcagtgc agcacagggc ccatgagcag tatcctctta   7500
ttatattctt cttatagtga ttctggatat taaagtggga atgaggggca ggccactaac   7560
gaagaagatg tttctcaaag aagccattct ccccacatag atcatctcag cagggttcag   7620
gaagataaag gaggatcaag gtcgaaggta ggaactaagg aagaacactg ggcaagtgga   7680
tccaggttgt ccaacgctga aagtaggaat ctaagcacta gtctctggat gctaggaggg   7740
cctctgcatg ggtatcaggc ttggattcaa agctcctgac tttctgtcta gtgtatgtgc   7800
agtgagcccc ttttcctcta actgaaagaa ggaaaaaaaa atggaaccca aaatattcta   7860
catagtttcc atgtcacagc cagggctggg cagtctcctg ttatttcttt taaaataaat   7920
atatcattta aatgcataaa taagcaaacc ctgctcggga atgggaggga gagtctctgg   7980
agtccacccc ttctcggccc tggctctgca gatagtgcta tcaaagccct gacagagccc   8040
tgcccattgc tgggccttgg agtgagtcag cctagtagag aggcagggca agccatctca   8100
tagctgctga gtgggagaga gaaaagggct cattgtctat aaactcaggt catggctatt   8160
cttattctca cactaagaaa aagaatgaga tgtcatcttg gaccattagc tccacaggta   8220
tcttcttccc tctagtggtc ataacagcag cttcagctac ctctctaaag agtcctgcca   8280
gatataggtc aggaaatata atccactaat aaaaagagaa acattttgac tgtagttgtt   8340
tgttttttgt cattgtgact atcaataaca ttctcactct ttcatcagta atcactcagg   8400
ttattctgtg accaacagac tgtgggaaaa atcagagaag gaggcatcct catgcttact   8460
agcctaaact gaaattgcta tagcagagtg aaccagaagg tttacagata ttttccacaa   8520
agagtaaaag gattgaagcc ttctccagat caatgcatag gaaataataa tggaccataa   8580
aacccatatt atgacgaaca acattaggat aagtcggcct actcgaccac gagggaattc   8640
cgataatcaa cctctggatt acaaaatttg tgaaagattg actggtattc ttaactatgt   8700
tgctcctttt acgctatgtg gatacgctgc tttaatgcct ttgtatcatg ctattgcttc   8760
ccgtatggct ttcattttct cctccttgta taaatcctgg ttgctgtctc tttatgagga   8820
gttgtggccc gttgtcaggc aacgtggcgt ggtgtgcact gtgtttgctg acgcaacccc   8880
cactggttgg ggcattgcca ccacctgtca gctcctttcc gggactttcg ctttccccct   8940
ccctattgcc acggcggaac tcatcgccgc ctgccttgcc cgctgctgga caggggctcg   9000
gctgttgggc actgacaatt ccgtggtgtt gtcggggaaa tcatcgtcct ttccttggct   9060
gctcgcctgt gttgccacct ggattctgcg cgggacgtcc ttctgctacg tcccttcggc   9120
cctcaatcca gcggaccttc cttcccgcgg cctgctgccg gctctgcggc ctcttccgcg   9180
tcttcgcctt cgccctcaga cgagtcggat ctccctttgg gccgcctccc cgcatcgata   9240
ccgtcgacct cgagacctag aaaaacatgg ccaattcgag ctcggtacct ttaagaccaa   9300
tgacttacaa ggcagctgta gatcttagcc actttttaaa agaaaagggg ggactggaag   9360
```

```
ggctaattca ctcccaacga agacaagatc ccagggatgt acgtccctaa cccgctaggg   9420
ggcagcaccc aggcctgcac tgccgcctgc cggcaggggt ccagtcctgc tttttgcttg   9480
tactgggtct ctctggttag accagatctg agcctgggag ctctctggct aactagggaa   9540
cccactgctt aagcctcaat aaagcttgcc ttgagtgctt caagtagtgt gtgcccgtct   9600
gttgtgtgac tctggtaact agagatccct cagacccttt tagtcagtgt ggaaaatctc   9660
tagcagtagt agttcatgtc atcttattat tcagtattta taacttgcaa agaaatgaat   9720
atcagagagt gagaggaact tgtttattgc agcttataat ggttacaaat aaagcaatag   9780
catcacaaat ttcacaaata aagcattttt ttcactgcat tctagttgtg gtttgtccaa   9840
actcatcaat gtatcttatc atgtctggct ctagctatcc cgcccctaac tccgcccatc   9900
ccgcccctaa ctccgcccag ttccgcccat tctccgcccc atggctgact aatttttttt   9960
atttatgcag aggccgaggc cgcctcggcc tctgagctat tccagaagta gtgaggaggc  10020
ttttttggag gcctaggctt ttgcgtcgag acgtacccaa ttcgccctat agtgagtcgt  10080
attacgcgcg ctcactggcc gtcgttttac aacgtcgtga ctgggaaaac cctggcgtta  10140
cccaacttaa tcgccttgca gcacatcccc ctttcgccag ctggcgtaat agcgaagagg  10200
cccgcaccga tcgcccttcc caacagttgc gcagcctgaa tggcgaatgg cgcgacgcgc  10260
cctgtagcgg cgcattaagc gcggcgggtg tggtggttac gcgcagcgtg accgctacac  10320
ttgccagcgc cctagcgccc gctcctttcg ctttcttccc ttcctttctc gccacgttcg  10380
ccggctttcc ccgtcaagct ctaaatcggg ggctcccttt agggttccga tttagtgctt  10440
tacggcacct cgaccccaaa aaacttgatt agggtgatgg ttcacgtagt gggccatcgc  10500
cctgatagac ggtttttcgc cctttgacgt tggagtccac gttctttaat agtggactct  10560
tgttccaaac tggaacaaca ctcaacccta tctcggtcta ttcttttgat ttataaggga  10620
ttttgccgat ttcggcctat tggttaaaaa atgagctgat ttaacaaaaa tttaacgcga  10680
attttaacaa aatattaacg tttacaattt cccaggtggc acttttcggg gaaatgtgcg  10740
cggaacccct atttgtttat ttttctaaat acattcaaat atgtatccgc tcatgagaca  10800
ataaccctga taaatgcttc aataatattg aaaaaggaag agtatgagta ttcaacattt  10860
ccgtgtcgcc cttattccct tttttgcggc attttgcctt cctgtttttg ctcacccaga  10920
aacgctggtg aaagtaaaag atgctgaaga tcagttgggt gcacgagtgg gttacatcga  10980
actggatctc aacagcggta agatccttga gagttttcgc cccgaagaac gttttccaat  11040
gatgagcact tttaaagttc tgctatgtgg cgcggtatta tcccgtattg acgccgggca  11100
agagcaactc ggtcgccgca tacactattc tcagaatgac ttggttgagt actcaccagt  11160
cacagaaaag catcttacgg atggcatgac agtaagagaa ttatgcagtg ctgccataac  11220
catgagtgat aacactgcgg ccaacttact tctgacaacg atcggaggac cgaaggagct  11280
aaccgctttt ttgcacaaca tgggggatca tgtaactcgc cttgatcgtt gggaaccgga  11340
gctgaatgaa gccataccaa acgacgagcg tgacaccacg atgcctgtag caatggcaac  11400
aacgttgcgc aaactattaa ctggcgaact acttactcta gcttcccggc aacaattaat  11460
agactggatg gaggcggata aagttgcagg accacttctg cgctcggccc ttccggctgg  11520
ctggtttatt gctgataaat ctggagccgg tgagcgtggg tctcgcggta tcattgcagc  11580
actggggcca gatggtaagc cctcccgtat cgtagttatc tacacgacgg ggagtcaggc  11640
aactatggat gaacgaaata gacagatcgc tgagataggt gcctcactga ttaagcattg  11700
```

```
gtaactgtca gaccaagttt actcatatat actttagatt gatttaaaac ttcattttta  11760

atttaaaagg atctaggtga agatcctttt tgataatctc atgaccaaaa tcccttaacg  11820

tgagttttcg ttccactgag cgtcagaccc cgtagaaaag atcaaaggat cttcttgaga  11880

tccttttttt ctgcgcgtaa tctgctgctt gcaaacaaaa aaaccaccgc taccagcggt  11940

ggtttgtttg ccggatcaag agctaccaac tctttttccg aaggtaactg gcttcagcag  12000

agcgcagata ccaaatactg tccttctagt gtagccgtag ttaggccacc acttcaagaa  12060

ctctgtagca ccgcctacat acctcgctct gctaatcctg ttaccagtgg ctgctgccag  12120

tggcgataag tcgtgtctta ccgggttgga ctcaagacga tagttaccgg ataaggcgca  12180

gcggtcgggc tgaacggggg gttcgtgcac acagcccagc ttggagcgaa cgacctacac  12240

cgaactgaga tacctacagc gtgagctatg agaaagcgcc acgcttcccg aagggagaaa  12300

ggcggacagg tatccggtaa gcggcagggt cggaacagga gagcgcacga gggagcttcc  12360

agggggaaac gcctggtatc tttatagtcc tgtcgggttt cgccacctct gacttgagcg  12420

tcgatttttg tgatgctcgt caggggggcg gagcctatgg aaaaacgcca gcaacgcggc  12480

cattttacg gttcctggcc ttttgctggc cttttgctca catgttcttt cctgcgttat  12540

cccctgattc tgtggataac cgtattaccg cctttgagtg agctgatacc gctcgccgca  12600

gccgaacgac cgagcgcagc gagtcagtga gcgaggaagc ggaagagcgc ccaatacgca  12660

aaccgcctct ccccgcgcgt tggccgattc attaatgcag ctggcacgac aggtttcccg  12720

actggaaagc gggcagtga                                               12739
```

```
<210> SEQ ID NO 2
<211> LENGTH: 433
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 2

tattgaggct aaggcatctg tgaaggaaag aaacatctcc tctaaaccac tatgctgcta     60

gagcctcttt tctgtactca agcctcattc agacactagt gtcaccagtc tcctcatata    120

cctattgtat tttcttcttc ttgctggttt agtcatgttt tctgggagct taggggctta    180

ttttattttg ttttgttttc taatcaacag agatgggcaa acccattatt tttttcttta    240

gacttgggat ggtgatagct gggcagcgtc agaaactgtg tgtggatata gataagagct    300

caggactatg ctgagctgtg atgagggagg ggcctagcta aaggcagtga gagtcagaat    360

gctcctgcta ttgccttctc agtccccacg cttggtttct acacaagtag atacatagaa    420

aaggctatag gtt                                                       433
```

```
<210> SEQ ID NO 3
<211> LENGTH: 289
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 3

catccttccc atgaagatgg atgaataagc catatctgac acctatgaaa taatgtttac     60

tttagtggca tattgcatta ggctacctgc cttggcacag tttttcttta cttttacctg    120

actgatgaaa caattaattg cttacataaa catgagtgct ctagttataa attccagtgt    180
```

aaaaaacacc ctggtttcga tattcatctt ttgagccttt tattttggtc agaacaagtt 240
ttcaagagca aatctcagcc tacaaaacaa atgagtccaa ttctagaac 289

<210> SEQ ID NO 4
<211> LENGTH: 392
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 4
tctttgtgtg tgcatagcag tggatgtgtc agcatacatc cttttaatta tagttgtata 60
tgtgtttgac tgctcattca ttcattcaaa attgtaaaat tgctaagaat acagcacaaa 120
aacagaatag aggaataaag ttcctgtttt catggacttg atagtggaaa gagcttgaca 180
ttaaataagc aaatgaaaca tgttatatac caatgagatt aggtgctatg gagaaaaaaa 240
aaaaactgaa atgaaggcca gagtgtgatt aggacagggt gaaagggtat cgctacttta 300
agtagtatgg caggaaagtc ctcactataa agttaacacc tgagagagta cccatagatg 360
atgaggaacc catttatatg aaactatgat ta 392

<210> SEQ ID NO 5
<211> LENGTH: 250
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 5
attcctcagg accatctaca taatttctag gcccaatata aaatgaaaat gaatagcccc 60
tttgtcaaaa attaaggatt tcatgtcagg aacagcaagg atgttaaacc aagcatgggg 120
ccatcaagct atatctgcta ttcatgatac gaaaaaataa agagtattct agttatttag 180
ccacatattt caagtttagt ctgatatcac cctttaaaca ctgccactca acctaaaaca 240
atgctagtct 250

<210> SEQ ID NO 6
<211> LENGTH: 673
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 6
ggccttttgc cacctagctg tccaggggtg ccttaaaatg gcaaacaagg tttgttttct 60
tttcctgttt tcatgccttc ctcttccata tccttgtttc atattaatac atgtgtatag 120
atcctaaaaa tctatacaca tgtattaata aagcctgatt ctgccgcttc taggtataga 180
ggccacctgc aagataaata tttgattcac aataactaat cattctatgg caattgataa 240
caacaaatat atatatatat atatatatac gtgtatgtgt atatatatat atatatatat 300
tcaggaaata atatattcta gaatatgtca cattctgtct caggcatcca ttttctttat 360
gatgccgttt gaggtggagt tttagtcagg tggtcagctt ctcctttttt ttgccatctg 420
ccctgtaagc atcctgctgg ggacccagat aggagtcatc actctaggct gagaacatct 480
gggcacacac cctaagcctc agcatgactc atcatgactc agcattgctg tgcttgagcc 540
agaaggtttg cttagaaggt tacacagaac cagaaggcgg gggtggggca ctgaccccga 600
caggggcctg gccagaactg ctcatgcttg gactatggga ggtcactaat ggagacacac 660
agaaatgtaa cag 673

<210> SEQ ID NO 7
<211> LENGTH: 389
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 7
gccctctact catggtctat ctctcctggc tcctgggagt catggactcc acccagcacc 60
accaacctga cctaaccacc tatctgagcc tgccagccta taacccatct gggccctgat 120
agctggtggc cagccctgac cccaccccac cctccctgga acctctgata gacacatctg 180
gcacaccagc tcgcaaagtc accgtgaggg tcttgtgttt gctgagtcaa aattccttga 240
aatccaagtc cttagagact cctgctccca aatttacagt catagacttc ttcatggctg 300
tctcctttat ccacagaatg attcctttgc ttcattgccc catccatctg atcctcctca 360
tcagtgcagc acagggccca tgagcagta 389

<210> SEQ ID NO 8
<211> LENGTH: 260
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 8
tcctcttatt atattcttct tatagtgatt ctggatatta aagtgggaat gaggggcagg 60
ccactaacga agaagatgtt tctcaaagaa gccattctcc ccacatagat catctcagca 120
gggttcagga agataaagga ggatcaaggt cgaaggtagg aactaaggaa gaacactggg 180
caagtggatc caggttgtcc aacgctgaaa gtaggaatct aagcactagt ctctggatgc 240
taggagggcc tctgcatggg 260

<210> SEQ ID NO 9
<211> LENGTH: 442
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 9
tatcaggctt ggattcaaag ctcctgactt tctgtctagt gtatgtgcag tgagcccctt 60
ttcctctaac tgaaagaagg aaaaaaaaat ggaacccaaa atattctaca tagtttccat 120
gtcacagcca gggctgggca gtctcctgtt atttctttta aaataaatat atcatttaaa 180
tgcataaata agcaaaccct gctcgggaat gggagggaga gtctctggag tccacccctt 240
ctcggccctg gctctgcaga tagtgctatc aaagccctga cagagccctg cccattgctg 300
ggccttggag tgagtcagcc tagtagagag gcagggcaag ccatctcata gctgctgagt 360
gggagagaga aaagggctca ttgtctataa actcaggtca tggctattct tattctcaca 420
ctaagaaaaa gaatgagatg tc 442

<210> SEQ ID NO 10
<211> LENGTH: 421
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 10
atcttggacc attagctcca caggtatctt cttccctcta gtggtcataa cagcagcttc 60
agctacctct ctaaagagtc ctgccagata taggtcagga aatataatcc actaataaaa 120
agagaaacat tttgactgta gttgtttgtt ttttgtcatt gtgactatca ataacattct 180
cactctttca tcagtaatca ctcaggttat tctgtgacca acagactgtg ggaaaaatca 240
gagaaggagg catcctcatg cttactagcc taaactgaaa ttgctatagc agagtgaacc 300
agaaggttta cagatatttt ccacaaagag taaaaggatt gaagccttct ccagatcaat 360
gcataggaaa taataatgga ccataaaacc catattatga cgaacaacat taggataagt 420
c 421

<210> SEQ ID NO 11
<211> LENGTH: 12014
<212> TYPE: DNA
<213> ORGANISM: Artificial
<220> FEATURE:
<223> OTHER INFORMATION: Lentiviral vector

<400> SEQUENCE: 11
gcgcaacgca attaatgtga gttagctcac tcattaggca ccccaggctt tacactttat 60
gcttccggct cgtatgttgt gtggaattgt gagcggataa caatttcaca caggaaacag 120
ctatgaccat gattacgcca agcgcgcaat taaccctcac taaagggaac aaaagctgga 180
gctgcaagct tggccattgc atacgttgta tccatatcat aatatgtaca tttatattgg 240
ctcatgtcca acattaccgc catgttgaca ttgattattg actagttatt aatagtaatc 300
aattacgggg tcattagttc atagcccata tatggagttc cgcgttacat aacttacggt 360
aaatggcccg cctggctgac cgcccaacga cccccgccca ttgacgtcaa taatgacgta 420
tgttcccata gtaacgccaa tagggacttt ccattgacgt caatgggtgg agtatttacg 480
gtaaactgcc cacttggcag tacatcaagt gtatcatatg ccaagtacgc cccctattga 540
cgtcaatgac ggtaaatggc ccgcctggca ttatgcccag tacatgacct tatgggactt 600
tcctacttgg cagtacatct acgtattagt catcgctatt accatggtga tgcggttttg 660
gcagtacatc aatgggcgtg gatagcggtt tgactcacgg ggatttccaa gtctccaccc 720
cattgacgtc aatgggagtt tgttttggca ccaaaatcaa cgggactttc caaaatgtcg 780
taacaactcc gccccattga cgcaaatggg cggtaggcgt gtacggtggg aggtctatat 840
aagcagagct cgtttagtga accggggtct ctctggttag accagatctg agcctgggag 900
ctctctggct aactagggaa cccactgctt aagcctcaat aaagcttgcc ttgagtgctt 960
caagtagtgt gtgcccgtct gttgtgtgac tctggtaact agagatccct cagacccttt 1020
tagtcagtgt ggaaaatctc tagcagtggc gcccgaacag ggacttgaaa gcgaaaggga 1080
aaccagagga gctctctcga cgcaggactc ggcttgctga agcgcgcacg gcaagaggcg 1140
aggggcggcg actggtgagt acgccaaaaa ttttgactag cggaggctag aaggagagag 1200
atgggtgcga gagcgtcagt attaagcggg ggagaattag atcgcgatgg gaaaaaattc 1260

```
ggttaaggcc aggggggaaag aaaaaatata aattaaaaca tatagtatgg gcaagcaggg   1320
agctagaacg attcgcagtt aatcctggcc tgttagaaac atcagaaggc tgtagacaaa   1380
tactgggaca gctacaacca tcccttcaga caggatcaga agaacttaga tcattatata   1440
atacagtagc aaccctctat tgtgtgcatc aaaggataga gataaaagac accaaggaag   1500
ctttagacaa gatagaggaa gagcaaaaca aaagtaagac caccgcacag caagcggccg   1560
ctgatcttca gacctggagg aggagatatg agggacaatt ggagaagtga attatataaa   1620
tataaagtag taaaaattga accattagga gtagcaccca ccaaggcaaa gagaagagtg   1680
gtgcagagag aaaaaagagc agtgggaata ggagctttgt tccttgggtt cttgggagca   1740
gcaggaagca ctatgggcgc agcgtcaatg acgctgacgg tacaggccag acaattattg   1800
tctggtatag tgcagcagca gaacaatttg ctgagggcta ttgaggcgca acagcatctg   1860
ttgcaactca cagtctgggg catcaagcag ctccaggcaa gaatcctggc tgtggaaaga   1920
tacctaaagg atcaacagct cctggggatt tggggttgct ctggaaaact catttgcacc   1980
actgctgtgc cttggaatgc tagttggagt aataaatctc tggaacagat ttggaatcac   2040
acgacctgga tggagtggga cagagaaatt aacaattaca caagcttaat acactcctta   2100
attgaagaat cgcaaaacca gcaagaaaag aatgaacaag aattattgga attagataaa   2160
tgggcaagtt tgtggaattg gtttaacata acaaattggc tgtggtatat aaaattattc   2220
ataatgatag taggaggctt ggtaggttta agaatagttt ttgctgtact ttctatagtg   2280
aatagagtta ggcagggata ttcaccatta tcgtttcaga cccacctccc aaccccgagg   2340
ggacccgacg ggcccgaagg aatagaagaa gaaggtggag agagagacag agacagatcc   2400
attcgattag tgaacggatc tcgacggtat cgatctcgac acaaatggca gtattcatcc   2460
acaattttaa aagaaaaggg gggattgggg ggtacagtgc aggggaaaga atagtagaca   2520
taatagcaac agacatacaa actaaagaat tacaaaaaca aattacaaaa attcaaaatt   2580
ttcgggttta ttacagggac agcagagatc cagtttgggt cgaggatatc ggatcggaat   2640
tctctagatg atcaggatcc ctcgagccct tatcgatcac gagactagcc tcgactacta   2700
gtggagatcc cccgggctgc agagccagaa gcaccataag ggacatgata agggagccag   2760
cagacctctg atctcttcct gaatgctaat cttaaacatc ctgaggaaga atgggacttc   2820
catttggggt gggcctatga tagggtaata agacagtagt gaatatcaag ctacaaaaag   2880
ccccctttca aattcttctc agtcctaact tttcatacta agcccagtcc ttccaaagca   2940
gactgtgaaa gagtgatagt tccgggagac tagcactgca gattccgggt cactgtgagt   3000
gggggaggca gggaagaagg gctcacagga cagtcaaacc atgccccctg tttttccttc   3060
ttcaagtaga cctctataag acaacagaga caactaaggc tgagtggcca ggcgaggaga   3120
aaccatctcg ccgtaaaaca tggaaggaac acttcagggg aaaggtggta tctctaagca   3180
agagaactga gtggagtcaa ggctgagaga tgcaggataa gcaaatgggt agtgaaaaga   3240
cattcatgag gacagctaaa acaataagta atgtaaaata cagcatagca aaactttaac   3300
ctccaaatca agcctctact tgaatccttt tctgagggat gaataaggca taggcatcag   3360
gggctgttgc caatgtgcat tagctgtttg cagcctcacc ttctttcatg gagtttaaga   3420
tatagtgtat tttcccaagg tttgaactag ctcttcattt ctttatgttt taaatgcact   3480
gacctcccac attccctttt tagtaaaata ttcagaaata atttaaatac atcattgcaa   3540
tgaaaataaa tgttttttat taggcagaat ccagatgctc aaggcccttc ataatatccc   3600
```

-continued

```
ccagtttagt agttggactt agggaacaaa ggaaccttta atagaaattg gacagcaaga   3660
aagcgagctt agtgatactt gtgggccagg gcattagcca caccagccac cactttctga   3720
taggcagcct gcactggtgg ggtgaattct ttgccaaagt gatgggccag cacacagacc   3780
agcacgttgc ccaggagctg tgggaggaag ataagaggta tgaacatgat tagcaaaagg   3840
gcctagcttg gactcagaat aatccagcct tatcccaacc ataaaataaa agcagaatgg   3900
tagctggatt gtagctgcta ttagcaatat gaaacctctt acatcagtta caatttatat   3960
gcagaaatat ttatatgcag aaatattgct attgccttaa cccagaaatt atcactgtta   4020
ttctttagaa tggtgcaaag aggcatgata cattgtatca ttattgccct gaaagaaaga   4080
gattagggaa agtattagaa ataagataaa caaaaaagta tattaaaaga agaaagcatt   4140
ttttaaaatt acaaatgcaa aattaccctg atttggtcaa tatgtgtacc ctgttacttc   4200
tccccttcct atgacatgaa cttaaccata gaaaagaagg ggaaagaaaa catcaagggt   4260
cccatagact caccctgaag ttctcaggat ccacgtgcag cttgtcacag tgcagctcac   4320
tcagctgggc aaaggtgccc ttgaggttgt ccaggtgagc caggccatca ctaaaggcac   4380
cgagcacttt cttgccatga gccttcacct tagggttgcc cataacagca tcaggagtgg   4440
acagatcccc aaaggactca aagaacctct gggtccaagg gtagaccacc agcagcctaa   4500
gggtgggaaa atagaccaat aggcagagag agtcagtgcc tatcagaaac ccaagagtct   4560
tctctgtctc cacatgccca gtttctattg gtctccttaa acctgtcttg taaccttgat   4620
accaacctgc ccagggcctc accaccaacg gcatccacgt tcaccttgtc ccacagggca   4680
gtaacggcag acttctcctc aggagtcagg tgcaccatgg tgtctgtttg aggttgctag   4740
tgaacacagt tgtgtcagaa gcaaatgtaa gcaatagatg gctctgccct gacttttatg   4800
cccagccctg gctcctgccc tccctgctcc tgggagtaga ttggccaacc ctagggtgtg   4860
gctccacagg gtgaggtcta agtgatgaca gccgtacctg tccttggctc ttctggcact   4920
ggcttaggag ttggacttca aaccctcagc cctccctcta agatatatct cttggcccca   4980
taccatcagt acaaattgct actaaaaaca tcctcctttg caagtgtatt tacccgacgc   5040
gtcggcgata agcttgatcc atcgatcaag cctcattcag acactagtgt caccagtctc   5100
ctcatatacc tattgtattt tcttcttctt gctggtttag tcatgttttc tgggagctta   5160
ggggcttatt ttattttgtt ttgttttcta atcaacagag atgggcaaac ccattatttt   5220
tttctttaga cttgggatgg tgatagctgg gcagcgtcag aaactgtgtg tggatataga   5280
taagagctca ggactatgct gagctgtgat gagggagggg cctagctaaa ggcagtgaga   5340
gtcagaatgc tcctgctatt gccttctcag tccccacgct tggtttctac acaagtatct   5400
gacacctatg aaataatgtt tactttagtg gcatattgca ttaggctacc tgccttggca   5460
cagtttttct ttacttttac ctgactgatg aaacaattaa ttgcttacat aaacatgagt   5520
gctctagtta taaattccag tgtaaaaaac accctggttt cgatattcat cttttgagcc   5580
ttttattttg gtcagaacaa gttttcaaga gcaaatctca gcctacaaaa caaatgagtc   5640
caattctata catcctttta attatagttg tatatgtgtt tgactgctca ttcattcatt   5700
caaaattgta aaattgctaa gaatacagca caaaaacaga atagaggaat aaagttcctg   5760
ttttcatgga cttgatagtg gaaagagctt gacattaaat aagcaaatga aacatgttat   5820
ataccaatga gattaggtgc tatggagaaa aaaaaaaaaa ctgaaatgaa ggccagagtg   5880
tgattaggac agggtgaaag ggtatcgcta ctttaagtag tatggcagga aagtcctcac   5940
tataaagtgg atttcatgtc aggaacagca aggatgttaa accaagcatg ggccatcaa    6000
```

```
gctatatctg ctattcatga tacgaaaaaa taaagagtat tctagttatt tagccacata   6060
tttcaagtag ctgtccaggg gtgccttaaa atggcaaaca aggtttgttt tcttttcctg   6120
ttttcatgcc ttcctcttcc atatccttgt ttcatattaa tacatgtgta tagatcctaa   6180
aaatctatac acatgtatta ataaagcctg attctgccgc ttctaggtat agaggccacc   6240
tgcaagataa atatttgatt cacaataact aatcattcta tggcaattga taacaacaaa   6300
tatatatata tatatatata cgtatatgtg tatatatata tatatatatt caggaaataa   6360
tatattctag aatatgtcac attctgtctc aggcatccat tttctttatg atgccgtttg   6420
aggtggagtt ttagtcaggt ggtcagcttc tcctttttt tgccatctgc cctgtaagca    6480
tcctgctggg gacccagata ggagtcatca ctctaggctg agaacatctg ggcacacacc   6540
ctaagcctca gcatgactca tcatgactca gcattgctgt gcttgagcca gaaggtttgc   6600
ttagaaggtt acacagaacc agaaggcggg ggtggggcac tgaccccgac aggggcctgg   6660
ccagaactgc tcatgcttgg actatgggag gtcactaatg gagacacaca catggtctat   6720
ctctcctggc tcctgggagt catggactcc acccagcacc accaacctga cctaaccacc   6780
tatctgagcc tgccagccta taacccatct gggccctgat agctggtggc cagccctgac   6840
cccaccccac cctccctgga acctctgata gacacatctg gcacaccagc tcgcaaagtc   6900
accgtgaggg tcttgtgttt gctgagtcaa aattccttga aatccaagtc cttagagact   6960
cctgctccca aatttacagt catagacttc ttcatggctg tctcctttat ccacagaatg   7020
attcctttgc ttcattgccc catccatctg atcctcctca tcagtgcagc acataaagtg   7080
ggaatgaggg gcaggccact aacgaagaag atgtttctca aagaagccat tctccccaca   7140
tagatcatct cagcagggtt caggaagata aaggaggatc aaggtcgaag gtaggaacta   7200
aggaagaaca ctgggcaagt ggatccaggt tgtccaacgc tgaaagtagg aatctaagca   7260
ctagtctctg gatgctctgt ctagtgtatg tgcagtgagc cccttttcct ctaactgaaa   7320
gaaggaaaaa aaaatggaac ccaaaatatt ctacatagtt tccatgtcac agccagggct   7380
gggcagtctc ctgttatttc ttttaaaata aatatatcat ttaaatgcat aaataagcaa   7440
accctgctcg ggaatgggag ggagagtctc tggagtccac cccttctcgg ccctggctct   7500
gcagatagtg ctatcaaagc cctgacagag ccctgcccat tgctgggcct tggagtgagt   7560
cagcctagta gagaggcagg gcaagccatc tcatagctgc tgagtgggag agagaaaagg   7620
gctcattgtc tataaactca taaaaagaga aacattttga ctgtagttgt ttgtttttttg  7680
tcattgtgac tatcaataac attctcactc tttcatcagt aatcactcag gttattctgt   7740
gaccaacaga ctgtgggaaa aatcagagaa ggaggcatcc tcatgcttac tagcctaaac   7800
tgaaattgct atagcagagt gaaccagaag gtttacagat attttccaca aagagtaaaa   7860
ggattgaagc cttctccaga tcaatgcata ggcctactcg accacgaggg aattccgata   7920
atcaacctct ggattacaaa atttgtgaaa gattgactgg tattcttaac tatgttgctc   7980
cttttacgct atgtggatac gctgctttaa tgcctttgta tcatgctatt gcttcccgta   8040
tggctttcat tttctcctcc ttgtataaat cctggttgct gtctctttat gaggagttgt   8100
ggcccgttgt caggcaacgt ggcgtggtgt gcactgtgtt tgctgacgca acccccactg   8160
gttggggcat tgccaccacc tgtcagctcc tttccgggac tttcgctttc cccctcccta   8220
ttgccacggc ggaactcatc gccgcctgcc ttgcccgctg ctggacaggg gctcggctgt   8280
tgggcactga caattccgtg gtgttgtcgg ggaaatcatc gtcctttcct tggctgctcg   8340
```

```
cctgtgttgc cacctggatt ctgcgcggga cgtccttctg ctacgtccct tcggccctca   8400
atccagcgga ccttccttcc cgcggcctgc tgccggctct gcggcctctt ccgcgtcttc   8460
gccttcgccc tcagacgagt cggatctccc tttgggccgc ctccccgcat cgataccgtc   8520
gacctcgaga cctagaaaaa catggccaat tcgagctcgg tacctttaag accaatgact   8580
tacaaggcag ctgtagatct tagccacttt ttaaaagaaa aggggggact ggaagggcta   8640
attcactccc aacgaagaca agatcccagg gatgtacgtc cctaacccgc taggggggcag   8700
cacccaggcc tgcactgccg cctgccggca ggggtccagt cctgcttttt gcttgtactg   8760
ggtctctctg gttagaccag atctgagcct gggagctctc tggctaacta gggaacccac   8820
tgcttaagcc tcaataaagc ttgccttgag tgcttcaagt agtgtgtgcc cgtctgttgt   8880
gtgactctgg taactagaga tccctcagac ccttttagtc agtgtggaaa atctctagca   8940
gtagtagttc atgtcatctt attattcagt atttataact tgcaaagaaa tgaatatcag   9000
agagtgagag gaacttgttt attgcagctt ataatggtta caaataaagc aatagcatca   9060
caaatttcac aaataaagca tttttttcac tgcattctag ttgtggtttg tccaaactca   9120
tcaatgtatc ttatcatgtc tggctctagc tatcccgccc ctaactccgc ccatcccgcc   9180
cctaactccg cccagttccg cccattctcc gccccatggc tgactaattt tttttattta   9240
tgcagaggcc gaggccgcct cggcctctga gctattccag aagtagtgag gaggcttttt   9300
tggaggccta ggcttttgcg tcgagacgta cccaattcgc cctatagtga gtcgtattac   9360
gcgcgctcac tggccgtcgt tttacaacgt cgtgactggg aaaaccctgg cgttacccaa   9420
cttaatcgcc ttgcagcaca tccccctttc gccagctggc gtaatagcga agaggcccgc   9480
accgatcgcc cttcccaaca gttgcgcagc ctgaatggcg aatggcgcga cgcgccctgt   9540
agcggcgcat taagcgcggc gggtgtggtg gttacgcgca gcgtgaccgc tacacttgcc   9600
agcgccctag cgcccgctcc tttcgctttc ttcccttcct ttctcgccac gttcgccggc   9660
tttccccgtc aagctctaaa tcgggggctc cctttagggt tccgatttag tgctttacgg   9720
cacctcgacc ccaaaaaact tgattagggt gatggttcac gtagtgggcc atcgccctga   9780
tagacggttt ttcgcccttt gacgttggag tccacgttct ttaatagtgg actcttgttc   9840
caaactggaa caacactcaa ccctatctcg gtctattctt ttgatttata agggattttg   9900
ccgatttcgg cctattggtt aaaaaatgag ctgatttaac aaaaatttaa cgcgaatttt   9960
aacaaaatat taacgtttac aatttcccag gtggcacttt tcggggaaat gtgcgcggaa  10020
cccctatttg tttatttttc taaatacatt caaatatgta tccgctcatg agacaataac  10080
cctgataaat gcttcaataa tattgaaaaa ggaagagtat gagtattcaa catttccgtg  10140
tcgcccttat tccctttttt gcggcatttt gccttcctgt ttttgctcac ccagaaacgc  10200
tggtgaaagt aaaagatgct gaagatcagt tgggtgcacg agtgggttac atcgaactgg  10260
atctcaacag cggtaagatc cttgagagtt ttcgccccga agaacgtttt ccaatgatga  10320
gcacttttaa agttctgcta tgtggcgcgg tattatcccg tattgacgcc gggcaagagc  10380
aactcggtcg ccgcatacac tattctcaga atgacttggt tgagtactca ccagtcacag  10440
aaaagcatct tacggatggc atgacagtaa gagaattatg cagtgctgcc ataaccatga  10500
gtgataacac tgcggccaac ttacttctga caacgatcgg aggaccgaag gagctaaccg  10560
cttttttgca caacatgggg gatcatgtaa ctcgccttga tcgttgggaa ccggagctga  10620
atgaagccat accaaacgac gagcgtgaca ccacgatgcc tgtagcaatg gcaacaacgt  10680
tgcgcaaact attaactggc gaactactta ctctagcttc ccggcaacaa ttaatagact  10740
```

```
ggatggaggc ggataaagtt gcaggaccac ttctgcgctc ggcccttccg gctggctggt  10800

ttattgctga taaatctgga gccggtgagc gtgggtctcg cggtatcatt gcagcactgg  10860

ggccagatgg taagccctcc cgtatcgtag ttatctacac gacggggagt caggcaacta  10920

tggatgaacg aaatagacag atcgctgaga taggtgcctc actgattaag cattggtaac  10980

tgtcagacca agtttactca tatatacttt agattgattt aaaacttcat ttttaattta  11040

aaaggatcta ggtgaagatc ctttttgata atctcatgac caaaatccct taacgtgagt  11100

tttcgttcca ctgagcgtca gaccccgtag aaaagatcaa aggatcttct tgagatcctt  11160

tttttctgcg cgtaatctgc tgcttgcaaa caaaaaaacc accgctacca gcggtggttt  11220

gtttgccgga tcaagagcta ccaactcttt ttccgaaggt aactggcttc agcagagcgc  11280

agataccaaa tactgtcctt ctagtgtagc cgtagttagg ccaccacttc aagaactctg  11340

tagcaccgcc tacatacctc gctctgctaa tcctgttacc agtggctgct gccagtggcg  11400

ataagtcgtg tcttaccggg ttggactcaa gacgatagtt accggataag gcgcagcggt  11460

cgggctgaac ggggggttcg tgcacacagc ccagcttgga gcgaacgacc tacaccgaac  11520

tgagatacct acagcgtgag ctatgagaaa gcgccacgct tcccgaaggg agaaaggcgg  11580

acaggtatcc ggtaagcggc agggtcggaa caggagagcg cacgagggag cttccagggg  11640

gaaacgcctg gtatctttat agtcctgtcg ggtttcgcca cctctgactt gagcgtcgat  11700

ttttgtgatg ctcgtcaggg gggcggagcc tatggaaaaa cgccagcaac gcggccattt  11760

ttacggttcc tggccttttg ctggcctttt gctcacatgt tctttcctgc gttatcccct  11820

gattctgtgg ataaccgtat taccgccttt gagtgagctg ataccgctcg ccgcagccga  11880

acgaccgagc gcagcgagtc agtgagcgag gaagcggaag agcgcccaat acgcaaaccg  11940

cctctccccg cgcgttggcc gattcattaa tgcagctggc acgacaggtt tcccgactgg  12000

aaagcgggca gtga                                                   12014
```

<210> SEQ ID NO 12
<211> LENGTH: 331
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 12

```
caagcctcat tcagacacta gtgtcaccag tctcctcata tacctattgt attttcttct     60

tcttgctggt ttagtcatgt tttctgggag cttaggggct tattttattt tgttttgttt    120

tctaatcaac agagatgggc aaacccatta tttttttctt tagacttggg atggtgatag    180

ctgggcagcg tcagaaactg tgtgtggata tagataagag ctcaggacta tgctgagctg    240

tgatgaggga ggggcctagc taaaggcagt gagagtcaga atgctcctgc tattgccttc    300

tcagtcccca cgcttggttt ctacacaagt a                                   331
```

<210> SEQ ID NO 13
<211> LENGTH: 251
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 13

```
tctgacacct atgaaataat gtttacttta gtggcatatt gcattaggct acctgccttg     60

gcacagtttt tctttacttt tacctgactg atgaaacaat taattgctta cataaacatg    120

agtgctctag ttataaattc cagtgtaaaa aacaccctgg tttcgatatt catcttttga    180

gccttttatt ttggtcagaa caagttttca agagcaaatc tcagcctaca aaacaaatga    240

gtccaattct a                                                         251


<210> SEQ ID NO 14
<211> LENGTH: 300
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 14

tacatccttt taattatagt tgtatatgtg tttgactgct cattcattca ttcaaaattg     60

taaaattgct aagaatacag cacaaaaaca gaatagagga ataaagttcc tgttttcatg    120

gacttgatag tggaaagagc ttgacattaa ataagcaaat gaaacatgtt atataccaat    180

gagattaggt gctatggaga aaaaaaaaaa aactgaaatg aaggccagag tgtgattagg    240

acagggtgaa agggtatcgc tactttaagt agtatggcag gaaagtcctc actataaagt    300


<210> SEQ ID NO 15
<211> LENGTH: 119
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 15

ggatttcatg tcaggaacag caaggatgtt aaaccaagca tggggccatc aagctatatc     60

tgctattcat gatacgaaaa aataaagagt attctagtta tttagccaca tatttcaag     119


<210> SEQ ID NO 16
<211> LENGTH: 643
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 16

tagctgtcca ggggtgcctt aaaatggcaa acaaggtttg ttttcttttc ctgttttcat     60

gccttcctct tccatatcct tgtttcatat taatacatgt gtatagatcc taaaaatcta    120

tacacatgta ttaataaagc ctgattctgc cgcttctagg tatagaggcc acctgcaaga    180

taaatatttg attcacaata actaatcatt ctatggcaat tgataacaac aaatatatat    240

atatatatat atacgtatat gtgtatatat atatatatat attcaggaaa taatatattc    300

tagaatatgt cacattctgt ctcaggcatc cattttcttt atgatgccgt ttgaggtgga    360

gttttagtca ggtggtcagc ttctcctttt ttttgccatc tgccctgtaa gcatcctgct    420

ggggacccag ataggagtca tcactctagg ctgagaacat ctgggcacac accctaagcc    480

tcagcatgac tcatcatgac tcagcattgc tgtgcttgag ccagaaggtt tgcttagaag    540

gttacacaga accagaaggc gggggtgggg cactgacccc gacaggggcc tggccagaac    600

tgctcatgct tggactatgg gaggtcacta atggagacac aca                      643
```

<210> SEQ ID NO 17
<211> LENGTH: 363
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 17

```
catggtctat ctctcctggc tcctgggagt catggactcc acccagcacc accaacctga     60

cctaaccacc tatctgagcc tgccagccta taacccatct gggccctgat agctggtggc    120

cagccctgac ccccaccccac cctccctgga acctctgata gacacatctg gcacaccagc    180

tcgcaaagtc accgtgaggg tcttgtgttt gctgagtcaa aattccttga aatccaagtc    240

cttagagact cctgctccca aatttacagt catagacttc ttcatggctg tctcctttat    300

ccacagaatg attcctttgc ttcattgccc catccatctg atcctcctca tcagtgcagc    360

aca                                                                  363
```

<210> SEQ ID NO 18
<211> LENGTH: 203
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 18

```
taaagtggga atgaggggca ggccactaac gaagaagatg tttctcaaag aagccattct     60

ccccacatag atcatctcag cagggttcag gaagataaag gaggatcaag gtcgaaggta    120

ggaactaagg aagaacactg ggcaagtgga tccaggttgt ccaacgctga aagtaggaat    180

ctaagcacta gtctctggat gct                                            203
```

<210> SEQ ID NO 19
<211> LENGTH: 363
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 19

```
ctgtctagtg tatgtgcagt gagcccccttt tcctctaact gaaagaagga aaaaaaaatg     60

gaacccaaaa tattctacat agtttccatg tcacagccag ggctgggcag tctcctgtta    120

tttcttttaa aataaatata tcatttaaat gcataaataa gcaaaccctg ctcgggaatg    180

ggagggagag tctctggagt ccacccccttc tcggccctgg ctctgcagat agtgctatca    240

aagccctgac agagccctgc ccattgctgg gccttggagt gagtcagcct agtagagagg    300

cagggcaagc catctcatag ctgctgagtg ggagagagaa aagggctcat tgtctataaa    360

ctc                                                                  363
```

<210> SEQ ID NO 20
<211> LENGTH: 251
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 20

```
ataaaaagag aaacattttg actgtagttg tttgtttttt gtcattgtga ctatcaataa      60
cattctcact ctttcatcag taatcactca ggttattctg tgaccaacag actgtgggaa     120
aaatcagaga aggaggcatc ctcatgctta ctagcctaaa ctgaaattgc tatagcagag     180
tgaaccagaa ggtttacaga tattttccac aaagagtaaa aggattgaag ccttctccag     240
atcaatgcat a                                                           251
```

<210> SEQ ID NO 21
<211> LENGTH: 10885
<212> TYPE: DNA
<213> ORGANISM: Artificial
<220> FEATURE:
<223> OTHER INFORMATION: Lentiviral vector

<400> SEQUENCE: 21

```
gcgcaacgca attaatgtga gttagctcac tcattaggca ccccaggctt tacactttat      60
gcttccggct cgtatgttgt gtggaattgt gagcggataa caatttcaca caggaaacag     120
ctatgaccat gattacgcca agcgcgcaat taaccctcac taaagggaac aaaagctgga     180
gctgcaagct tggccattgc atacgttgta tccatatcat aatatgtaca tttatattgg     240
ctcatgtcca acattaccgc catgttgaca ttgattattg actagttatt aatagtaatc     300
aattacgggg tcattagttc atagcccata tatggagttc cgcgttacat aacttacggt     360
aaatggcccg cctggctgac cgcccaacga cccccgccca ttgacgtcaa taatgacgta     420
tgttcccata gtaacgccaa tagggacttt ccattgacgt caatgggtgg agtatttacg     480
gtaaactgcc cacttggcag tacatcaagt gtatcatatg ccaagtacgc cccctattga     540
cgtcaatgac ggtaaatggc ccgcctggca ttatgcccag tacatgacct tatgggactt     600
tcctacttgg cagtacatct acgtattagt catcgctatt accatggtga tgcggttttg     660
gcagtacatc aatgggcgtg gatagcggtt tgactcacgg ggatttccaa gtctccaccc     720
cattgacgtc aatgggagtt tgttttggca ccaaaatcaa cgggactttc caaaatgtcg     780
taacaactcc gccccattga cgcaaatggg cggtaggcgt gtacggtggg aggtctatat     840
aagcagagct cgtttagtga accggggtct ctctggttag accagatctg agcctgggag     900
ctctctggct aactagggaa cccactgctt aagcctcaat aaagcttgcc ttgagtgctt     960
caagtagtgt gtgcccgtct gttgtgtgac tctggtaact agagatccct cagacccttt    1020
tagtcagtgt ggaaaatctc tagcagtggc gcccgaacag ggacttgaaa gcgaaaggga    1080
aaccagagga gctctctcga cgcaggactc ggcttgctga agcgcgcacg gcaagaggcg    1140
aggggcggcg actggtgagt acgccaaaaa ttttgactag cggaggctag aaggagagag    1200
atgggtgcga gagcgtcagt attaagcggg ggagaattag atcgcgatgg gaaaaaattc    1260
ggttaaggcc agggggaaag aaaaaatata aattaaaaca tatagtatgg gcaagcaggg    1320
agctagaacg attcgcagtt aatcctggcc tgttagaaac atcagaaggc tgtagacaaa    1380
tactgggaca gctacaacca tcccttcaga caggatcaga agaacttaga tcattatata    1440
atacagtagc aaccctctat tgtgtgcatc aaaggataga gataaaagac accaaggaag    1500
ctttagacaa gatagaggaa gagcaaaaca aaagtaagac caccgcacag caagcggccg    1560
ctgatcttca gacctggagg aggagatatg agggacaatt ggagaagtga attatataaa    1620
tataaagtag taaaaattga accattagga gtagcaccca ccaaggcaaa gagaagagtg    1680
gtgcagagag aaaaaagagc agtgggaata ggagctttgt tccttgggtt cttgggagca    1740
```

-continued

```
gcaggaagca ctatgggcgc agcgtcaatg acgctgacgg tacaggccag acaattattg   1800
tctggtatag tgcagcagca gaacaatttg ctgagggcta ttgaggcgca acagcatctg   1860
ttgcaactca cagtctgggg catcaagcag ctccaggcaa gaatcctggc tgtggaaaga   1920
tacctaaagg atcaacagct cctggggatt tggggttgct ctggaaaact catttgcacc   1980
actgctgtgc cttggaatgc tagttggagt aataaatctc tggaacagat ttggaatcac   2040
acgacctgga tggagtggga cagagaaatt aacaattaca caagcttaat acactcctta   2100
attgaagaat cgcaaaacca gcaagaaaag aatgaacaag aattattgga attagataaa   2160
tgggcaagtt tgtggaattg gtttaacata acaaattggc tgtggtatat aaaattattc   2220
ataatgatag taggaggctt ggtaggttta agaatagttt ttgctgtact ttctatagtg   2280
aatagagtta ggcagggata ttcaccatta tcgtttcaga cccacctccc aaccccgagg   2340
ggacccgacg ggcccgaagg aatagaagaa gaaggtggag agagagacag agacagatcc   2400
attcgattag tgaacggatc tcgacggtat cgatctcgac acaaatggca gtattcatcc   2460
acaattttaa aagaaaaggg gggattgggg ggtacagtgc aggggaaaga atagtagaca   2520
taatagcaac agacatacaa actaaagaat tacaaaaaca aattacaaaa attcaaaatt   2580
ttcgggttta ttacagggac agcagagatc cagtttgggt cgaggatatc ggatcggaat   2640
tctctagatg atcaggatcc ctcgagccct tatcgatcac gagactagcc tcgactacta   2700
gtggagatcc cccgggctgc agagccagaa gcaccataag ggacatgata agggagccag   2760
cagacctctg atctcttcct gaatgctaat cttaaacatc ctgaggaaga atgggacttc   2820
catttggggt gggcctatga tagggtaata agacagtagt gaatatcaag ctacaaaaag   2880
ccccctttca aattcttctc agtcctaact tttcatacta agcccagtcc ttccaaagca   2940
gactgtgaaa gagtgatagt tccgggagac tagcactgca gattccgggt cactgtgagt   3000
gggggaggca gggaagaagg gctcacagga cagtcaaacc atgccccctg tttttccttc   3060
ttcaagtaga cctctataag acaacagaga caactaaggc tgagtggcca ggcgaggaga   3120
aaccatctcg ccgtaaaaca tggaaggaac acttcagggg aaaggtggta tctctaagca   3180
agagaactga gtggagtcaa ggctgagaga tgcaggataa gcaaatgggt agtgaaaaga   3240
cattcatgag gacagctaaa acaataagta atgtaaaata cagcatagca aaactttaac   3300
ctccaaatca agcctctact tgaatccttt tctgagggat gaataaggca taggcatcag   3360
gggctgttgc caatgtgcat tagctgtttg cagcctcacc ttctttcatg gagtttaaga   3420
tatagtgtat tttcccaagg tttgaactag ctcttcattt ctttatgttt taaatgcact   3480
gacctcccac attccctttt tagtaaaata ttcagaaata atttaaatac atcattgcaa   3540
tgaaaataaa tgttttttat taggcagaat ccagatgctc aaggcccttc ataatatccc   3600
ccagtttagt agttggactt agggaacaaa ggaaccttta atagaaattg gacagcaaga   3660
aagcgagctt agtgatactt gtgggccagg gcattagcca caccagccac cactttctga   3720
taggcagcct gcactggtgg ggtgaattct ttgccaaagt gatgggccag cacacagacc   3780
agcacgttgc ccaggagctg tgggaggaag ataagaggta tgaacatgat tagcaaaagg   3840
gcctagcttg gactcagaat aatccagcct tatcccaacc ataaaataaa agcagaatgg   3900
tagctggatt gtagctgcta ttagcaatat gaaacctctt acatcagtta caatttatat   3960
gcagaaatat ttatatgcag aaatattgct attgccttaa cccagaaatt atcactgtta   4020
ttctttagaa tggtgcaaag aggcatgata cattgtatca ttattgccct gaaagaaaga   4080
gattagggaa agtattagaa ataagataaa caaaaaagta tattaaaaga agaaagcatt   4140
```

```
ttttaaaatt acaaatgcaa aattaccctg atttggtcaa tatgtgtacc ctgttacttc   4200
tccccttcct atgacatgaa cttaaccata gaaaagaagg ggaaagaaaa catcaagggt   4260
cccatagact caccctgaag ttctcaggat ccacgtgcag cttgtcacag tgcagctcac   4320
tcagctgggc aaaggtgccc ttgaggttgt ccaggtgagc caggccatca ctaaaggcac   4380
cgagcacttt cttgccatga gccttcacct tagggttgcc cataacagca tcaggagtgg   4440
acagatcccc aaaggactca aagaacctct gggtccaagg gtagaccacc agcagcctaa   4500
gggtgggaaa atagaccaat aggcagagag agtcagtgcc tatcagaaac ccaagagtct   4560
tctctgtctc cacatgccca gtttctattg gtctccttaa acctgtcttg taaccttgat   4620
accaacctgc ccagggcctc accaccaacg gcatccacgt tcaccttgtc ccacagggca   4680
gtaacggcag acttctcctc aggagtcagg tgcaccatgg tgtctgtttg aggttgctag   4740
tgaacacagt tgtgtcagaa gcaaatgtaa gcaatagatg gctctgccct gacttttatg   4800
cccagccctg gctcctgccc tccctgctcc tgggagtaga ttggccaacc ctagggtgtg   4860
gctccacagg gtgaggtcta agtgatgaca gccgtacctg tccttggctc ttctggcact   4920
ggcttaggag ttggacttca aaccctcagc cctccctcta agatatatct cttggcccca   4980
taccatcagt acaaattgct actaaaaaca tcctcctttg caagtgtatt tacccgacgc   5040
gtcggcgata agcttgatcc atcgatgtat tttcttcttc ttgctggttt agtcatgttt   5100
tctgggagct taggggctta ttttattttg ttttgttttc taatcaacag agatgggcaa   5160
acccattatt tttttcttta gacttgggat ggtgatagct gggcagcgtc agaaactgtg   5220
tgtggatata gataagagct caggactatg ctgagctgtg atgagggagg ggcctagcta   5280
aaggcagtga gagtcagaat gctcctgcta ttgccttctc agtccccacg cttggtttct   5340
acacactacc tgccttggca cagtttttct ttacttttac ctgactgatg aaacaattaa   5400
ttgcttacat aaacatgagt gctctagtta taaattccag tgtaaaaaac accctggttt   5460
cgatattcat cttttgagcc ttttattttg gtcagatatt aataaagcct gattctgccg   5520
cttctaggta tagaggccac ctgcaagata aatatttgat tcacaataac taatcattct   5580
atggcaattg ataacaacaa atatatatat atatatatat atacgttgtc acattctgtc   5640
tcaggcatcc attttcttta tgatgccgtt tgaggtggag ttttagtcag gtggtcagct   5700
tctccttttt tttgccatct gccctgtaag catcctgctg gggacccaga taggagtcat   5760
cactctaggc tgagaacatc tggcacacaa ccctaagcct cagcatgact catcatgact   5820
cagcattgct gtgcttgagc cagaaggttt gcttagaagg ttacacagaa ccagaaggcg   5880
ggggtggggc actgaccccg acaggggcct ggccagaact gctcatgctt ggactatggg   5940
agagcctgcc agcctataac ccatctgggc cctgatagct ggtggccagc cctgacccca   6000
ccccaccctc cctggaacct ctgatagaca catctggcac accagctcgc aaagtcaccg   6060
tgagggtctt gtgtttgctg agtcaaaatt ccttgaaatc caagtcctta gagactcctg   6120
ctcccaaatt tacagtcata gacttcttct tctccccaca tagatcatct cagcagggtt   6180
caggaagata aaggaggatc aaggtcgaag gtaggaacta aggaagaaca ctgggcaagt   6240
ggatccaggt tgtccaacgc tgaaagtagg aatctaagca aaaaaatgga acccaaaata   6300
ttctacatag tttccatgtc acagccaggg ctgggcagtc tcctgttatt tcttttaaaa   6360
taaatatatc atttaaatgc ataaataagc aaaccctgct cgggaatggg agggagagtc   6420
tctggagtcc accccttctc ggccctggct ctgcagatag tgctatcaaa gccctgacag   6480
```

```
agccctgccc attgctgggc cttggagtga gtcagcctag tagagaggca gggcaagcca   6540
tctcatagct gctgagtggg agagagaaaa gggctcattt agttgtttgt tttttgtcat   6600
tgtgactatc aataacattc tcactctttc atcagtaatc actcaggtta ttctgtgacc   6660
aacagactgt gggaaaaatc agagaaggag gcatcctcat gcttactagc ctaaactgaa   6720
attgctatag cagagtgaac cagaaggttt acagatattt tcggcctact cgaccacgag   6780
ggaattccga taatcaacct ctggattaca aaatttgtga aagattgact ggtattctta   6840
actatgttgc tccttttacg ctatgtggat acgctgcttt aatgcctttg tatcatgcta   6900
ttgcttcccg tatggctttc attttctcct ccttgtataa atcctggttg ctgtctcttt   6960
atgaggagtt gtggcccgtt gtcaggcaac gtggcgtggt gtgcactgtg tttgctgacg   7020
caacccccac tggttggggc attgccacca cctgtcagct cctttccggg actttcgctt   7080
tccccctccc tattgccacg gcggaactca tcgccgcctg ccttgcccgc tgctggacag   7140
gggctcggct gttgggcact gacaattccg tggtgttgtc ggggaaatca tcgtcctttc   7200
cttggctgct cgcctgtgtt gccacctgga ttctgcgcgg gacgtccttc tgctacgtcc   7260
cttcggccct caatccaggg accttccttc ccgcggcctg ctgccggctc tgcggcctct   7320
tccgcgtctt cgccttcgcc ctcagacgag tcggatctcc ctttgggccg cctccccgca   7380
tcgataccgt cgacctcgag acctagaaaa acatggccaa ttcgagctcg gtacctttaa   7440
gaccaatgac ttacaaggca gctgtagatc ttagccactt tttaaaagaa aaggggggac   7500
tggaagggct aattcactcc caacgaagac aagatcccag ggatgtacgt ccctaacccg   7560
ctagggggca gcacccaggc ctgcactgcc gcctgccggc aggggtccag tcctgctttt   7620
tgcttgtact gggtctctct ggttagacca gatctgagcc tgggagctct ctggctaact   7680
agggaaccca ctgcttaagc ctcaataaag cttgccttga gtgcttcaag tagtgtgtgc   7740
ccgtctgttg tgtgactctg gtaactagag atccctcaga cccttttagt cagtgtggaa   7800
aatctctagc agtagtagtt catgtcatct tattattcag tatttataac ttgcaaagaa   7860
atgaatatca gagagtgaga ggaacttgtt tattgcagct tataatggtt acaaataaag   7920
caatagcatc acaaatttca caaataaagc atttttttca ctgcattcta gttgtggttt   7980
gtccaaactc atcaatgtat cttatcatgt ctggctctag ctatcccgcc cctaactccg   8040
cccatcccgc ccctaactcc gcccagttcc gcccattctc cgccccatgg ctgactaatt   8100
ttttttattt atgcagaggc cgaggccgcc tcggcctctg agctattcca gaagtagtga   8160
ggaggctttt ttggaggcct aggcttttgc gtcgagacgt acccaattcg ccctatagtg   8220
agtcgtatta cgcgcgctca ctggccgtcg ttttacaacg tcgtgactgg gaaaaccctg   8280
gcgttaccca acttaatcgc cttgcagcac atcccccttt cgccagctgg cgtaatagcg   8340
aagaggcccg caccgatcgc ccttcccaac agttgcgcag cctgaatggc gaatggcgcg   8400
acgcgccctg tagcggcgca ttaagcgcgg cgggtgtggt ggttacgcgc agcgtgaccg   8460
ctacacttgc cagcgcccta gcgcccgctc ctttcgcttt cttcccttcc tttctcgcca   8520
cgttcgccgg ctttccccgt caagctctaa atcgggggct ccctttaggg ttccgattta   8580
gtgctttacg gcacctcgac cccaaaaaac ttgattaggg tgatggttca cgtagtgggc   8640
catcgccctg atagacggtt tttcgccctt tgacgttgga gtccacgttc tttaatagtg   8700
gactcttgtt ccaaactgga acaacactca accctatctc ggtctattct tttgatttat   8760
aagggatttt gccgatttcg gcctattggt taaaaaatga gctgatttaa caaaaattta   8820
acgcgaattt taacaaaata ttaacgttta caatttccca ggtggcactt ttcggggaaa   8880
```

```
tgtgcgcgga acccctattt gtttattttt ctaaatacat tcaaatatgt atccgctcat    8940
gagacaataa ccctgataaa tgcttcaata atattgaaaa aggaagagta tgagtattca    9000
acatttccgt gtcgccctta ttcccttttt tgcggcattt tgccttcctg tttttgctca    9060
cccagaaacg ctggtgaaag taaaagatgc tgaagatcag ttgggtgcac gagtgggtta    9120
catcgaactg gatctcaaca gcggtaagat ccttgagagt tttcgccccg aagaacgttt    9180
tccaatgatg agcactttta aagttctgct atgtggcgcg gtattatccc gtattgacgc    9240
cgggcaagag caactcggtc gccgcataca ctattctcag aatgacttgg ttgagtactc    9300
accagtcaca gaaaagcatc ttacggatgg catgacagta agagaattat gcagtgctgc    9360
cataaccatg agtgataaca ctgcggccaa cttacttctg acaacgatcg gaggaccgaa    9420
ggagctaacc gcttttttgc acaacatggg ggatcatgta actcgccttg atcgttggga    9480
accggagctg aatgaagcca taccaaacga cgagcgtgac accacgatgc ctgtagcaat    9540
ggcaacaacg ttgcgcaaac tattaactgg cgaactactt actctagctt cccggcaaca    9600
attaatagac tggatggagg cggataaagt tgcaggacca cttctgcgct cggcccttcc    9660
ggctggctgg tttattgctg ataaatctgg agccggtgag cgtgggtctc gcggtatcat    9720
tgcagcactg gggccagatg gtaagccctc ccgtatcgta gttatctaca cgacggggag    9780
tcaggcaact atggatgaac gaaatagaca gatcgctgag ataggtgcct cactgattaa    9840
gcattggtaa ctgtcagacc aagtttactc atatatactt tagattgatt taaaacttca    9900
tttttaattt aaaaggatct aggtgaagat cctttttgat aatctcatga ccaaaatccc    9960
ttaacgtgag ttttcgttcc actgagcgtc agaccccgta gaaaagatca aaggatcttc   10020
ttgagatcct ttttttctgc gcgtaatctg ctgcttgcaa acaaaaaaac caccgctacc   10080
agcggtggtt tgtttgccgg atcaagagct accaactctt tttccgaagg taactggctt   10140
cagcagagcg cagataccaa atactgtcct tctagtgtag ccgtagttag gccaccactt   10200
caagaactct gtagcaccgc ctacatacct cgctctgcta atcctgttac cagtggctgc   10260
tgccagtggc gataagtcgt gtcttaccgg gttggactca agacgatagt taccggataa   10320
ggcgcagcgg tcgggctgaa cggggggttc gtgcacacag cccagcttgg agcgaacgac   10380
ctacaccgaa ctgagatacc tacagcgtga gctatgagaa agcgccacgc ttcccgaagg   10440
gagaaaggcg gacaggtatc cggtaagcgg cagggtcgga acaggagagc gcacgaggga   10500
gcttccaggg ggaaacgcct ggtatcttta tagtcctgtc gggtttcgcc acctctgact   10560
tgagcgtcga tttttgtgat gctcgtcagg ggggcggagc ctatggaaaa acgccagcaa   10620
cgcggccatt tttacggttc ctggcctttt gctggccttt tgctcacatg ttctttcctg   10680
cgttatcccc tgattctgtg gataaccgta ttaccgcctt tgagtgagct gataccgctc   10740
gccgcagccg aacgaccgag cgcagcgagt cagtgagcga ggaagcggaa gagcgcccaa   10800
tacgcaaacc gcctctcccc gcgcgttggc cgattcatta atgcagctgg cacgacaggt   10860
ttcccgactg gaaagcgggc agtga                                         10885
```

<210> SEQ ID NO 22
<211> LENGTH: 279
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 22

```
gtattttctt cttcttgctg gtttagtcat gttttctggg agcttagggg cttattttat     60

tttgttttgt tttctaatca acagagatgg gcaaacccat tatttttttc tttagacttg    120

ggatggtgat agctgggcag cgtcagaaac tgtgtgtgga tatagataag agctcaggac    180

tatgctgagc tgtgatgagg gaggggccta gctaaaggca gtgagagtca gaatgctcct    240

gctattgcct tctcagtccc cacgcttggt ttctacaca                           279


<210> SEQ ID NO 23
<211> LENGTH: 151
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 23

ctacctgcct tggcacagtt tttctttact tttacctgac tgatgaaaca attaattgct     60

tacataaaca tgagtgctct agttataaat tccagtgtaa aaaacaccct ggtttcgata    120

ttcatctttt gagcctttta ttttggtcag a                                   151


<210> SEQ ID NO 24
<211> LENGTH: 131
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 24

tattaataaa gcctgattct gccgcttcta ggtatagagg ccacctgcaa gataaatatt     60

tgattcacaa taactaatca ttctatggca attgataaca acaaatatat atatatatat    120

atatatacgt t                                                         131


<210> SEQ ID NO 25
<211> LENGTH: 315
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 25

gtcacattct gtctcaggca tccattttct ttatgatgcc gtttgaggtg gagttttagt     60

caggtggtca gcttctcctt ttttttgcca tctgccctgt aagcatcctg ctggggaccc    120

agataggagt catcactcta ggctgagaac atctgggcac acaccctaag cctcagcatg    180

actcatcatg actcagcatt gctgtgcttg agccagaagg tttgcttaga aggttacaca    240

gaaccagaag gcgggggtgg ggcactgacc ccgacagggg cctggccaga actgctcatg    300

cttggactat gggag                                                     315


<210> SEQ ID NO 26
<211> LENGTH: 207
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 26
```

```
agcctgccag cctataaccc atctgggccc tgatagctgg tggccagccc tgaccccacc     60

ccaccctccc tggaacctct gatagacaca tctggcacac cagctcgcaa agtcaccgtg    120

agggtcttgt gtttgctgag tcaaaattcc ttgaaatcca agtccttaga gactcctgct    180

cccaaattta cagtcataga cttcttc                                         207


<210> SEQ ID NO 27
<211> LENGTH: 131
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 27

ttctccccac atagatcatc tcagcagggt tcaggaagat aaaggaggat caaggtcgaa     60

ggtaggaact aaggaagaac actgggcaag tggatccagg ttgtccaacg ctgaaagtag    120

gaatctaagc a                                                          131


<210> SEQ ID NO 28
<211> LENGTH: 299
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 28

aaaaaatgga acccaaaata ttctacatag tttccatgtc acagccaggg ctgggcagtc     60

tcctgttatt tcttttaaaa taaatatatc atttaaatgc ataaataagc aaaccctgct    120

cgggaatggg agggagagtc tctggagtcc acccccttctc ggccctggct ctgcagatag    180

tgctatcaaa gccctgacag agccctgccc attgctgggc cttggagtga gtcagcctag    240

tagagaggca gggcaagcca tctcatagct gctgagtggg agagagaaaa gggctcatt     299


<210> SEQ ID NO 29
<211> LENGTH: 183
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 29

tagttgtttg ttttttgtca ttgtgactat caataacatt ctcactcttt catcagtaat     60

cactcaggtt attctgtgac caacagactg tgggaaaaat cagagaagga ggcatcctca    120

tgcttactag cctaaactga aattgctata gcagagtgaa ccagaaggtt tacagatatt    180

ttc                                                                   183


<210> SEQ ID NO 30
<211> LENGTH: 10284
<212> TYPE: DNA
<213> ORGANISM: Artificial
<220> FEATURE:
<223> OTHER INFORMATION: Lentiviral vector

<400> SEQUENCE: 30

gcgcaacgca attaatgtga gttagctcac tcattaggca ccccaggctt tacactttat     60

gcttccggct cgtatgttgt gtggaattgt gagcggataa caatttcaca caggaaacag    120
```

-continued

```
ctatgaccat gattacgcca agcgcgcaat taaccctcac taaagggaac aaaagctgga    180
gctgcaagct tggccattgc atacgttgta tccatatcat aatatgtaca tttatattgg    240
ctcatgtcca acattaccgc catgttgaca ttgattattg actagttatt aatagtaatc    300
aattacgggg tcattagttc atagcccata tatggagttc cgcgttacat aacttacggt    360
aaatggcccg cctggctgac cgcccaacga cccccgccca ttgacgtcaa taatgacgta    420
tgttcccata gtaacgccaa tagggacttt ccattgacgt caatgggtgg agtatttacg    480
gtaaactgcc cacttggcag tacatcaagt gtatcatatg ccaagtacgc cccctattga    540
cgtcaatgac ggtaaatggc ccgcctggca ttatgcccag tacatgacct tatgggactt    600
tcctacttgg cagtacatct acgtattagt catcgctatt accatggtga tgcggttttg    660
gcagtacatc aatgggcgtg gatagcggtt tgactcacgg ggatttccaa gtctccaccc    720
cattgacgtc aatgggagtt tgttttggca ccaaaatcaa cgggactttc caaaatgtcg    780
taacaactcc gccccattga cgcaaatggg cggtaggcgt gtacggtggg aggtctatat    840
aagcagagct cgtttagtga accggggtct ctctggttag accagatctg agcctgggag    900
ctctctggct aactagggaa cccactgctt aagcctcaat aaagcttgcc ttgagtgctt    960
caagtagtgt gtgcccgtct gttgtgtgac tctggtaact agagatccct cagacccttt   1020
tagtcagtgt ggaaaatctc tagcagtggc gcccgaacag ggacttgaaa gcgaaaggga   1080
aaccagagga gctctctcga cgcaggactc ggcttgctga agcgcgcacg gcaagaggcg   1140
aggggcggcg actggtgagt acgccaaaaa ttttgactag cggaggctag aaggagagag   1200
atgggtgcga gagcgtcagt attaagcggg ggagaattag atcgcgatgg gaaaaaattc   1260
ggttaaggcc agggggaaag aaaaaatata aattaaaaca tatagtatgg gcaagcaggg   1320
agctagaacg attcgcagtt aatcctggcc tgttagaaac atcagaaggc tgtagacaaa   1380
tactgggaca gctacaacca tcccttcaga caggatcaga agaacttaga tcattatata   1440
atacagtagc aaccctctat tgtgtgcatc aaaggataga gataaaagac accaaggaag   1500
ctttagacaa gatagaggaa gagcaaaaca aaagtaagac caccgcacag caagcggccg   1560
ctgatcttca gacctggagg aggagatatg agggacaatt ggagaagtga attatataaa   1620
tataaagtag taaaaattga accattagga gtagcaccca ccaaggcaaa gagaagagtg   1680
gtgcagagag aaaaaagagc agtgggaata ggagctttgt tccttgggtt cttgggagca   1740
gcaggaagca ctatgggcgc agcgtcaatg acgctgacgg tacaggccag acaattattg   1800
tctggtatag tgcagcagca gaacaatttg ctgagggcta ttgaggcgca acagcatctg   1860
ttgcaactca cagtctgggg catcaagcag ctccaggcaa gaatcctggc tgtggaaaga   1920
tacctaaagg atcaacagct cctggggatt tggggttgct ctggaaaact catttgcacc   1980
actgctgtgc cttggaatgc tagttggagt aataaatctc tggaacagat ttggaatcac   2040
acgacctgga tggagtggga cagagaaatt aacaattaca caagcttaat acactcctta   2100
attgaagaat cgcaaaacca gcaagaaaag aatgaacaag aattattgga attagataaa   2160
tgggcaagtt tgtggaattg gtttaacata acaaattggc tgtggtatat aaaattattc   2220
ataatgatag taggaggctt ggtaggttta agaatagttt ttgctgtact ttctatagtg   2280
aatagagtta ggcagggata ttcaccatta tcgtttcaga cccacctccc aaccccgagg   2340
ggacccgacg ggcccgaagg aatagaagaa gaaggtggag agagagacag agacagatcc   2400
attcgattag tgaacggatc tcgacggtat cgatctcgac acaaatggca gtattcatcc   2460
acaattttaa aagaaaaggg gggattgggg ggtacagtgc aggggaaaga atagtagaca   2520
```

```
taatagcaac agacatacaa actaaagaat tacaaaaaca aattacaaaa attcaaaatt   2580
ttcgggttta ttacagggac agcagagatc cagtttgggt cgaggatatc ggatcggaat   2640
tctctagatg atcaggatcc ctcgagccct tatcgatcac gagactagcc tcgactacta   2700
gtggagatcc cccgggctgc agagccagaa gcaccataag ggacatgata agggagccag   2760
cagacctctg atctcttcct gaatgctaat cttaaacatc ctgaggaaga atgggacttc   2820
catttggggt gggcctatga tagggtaata agacagtagt gaatatcaag ctacaaaaag   2880
ccccctttca aattcttctc agtcctaact tttcatacta agcccagtcc ttccaaagca   2940
gactgtgaaa gagtgatagt tccgggagac tagcactgca gattccgggt cactgtgagt   3000
gggggaggca gggaagaagg gctcacagga cagtcaaacc atgccccctg tttttccttc   3060
ttcaagtaga cctctataag acaacagaga caactaaggc tgagtggcca ggcgaggaga   3120
aaccatctcg ccgtaaaaca tggaaggaac acttcagggg aaaggtggta tctctaagca   3180
agagaactga gtggagtcaa ggctgagaga tgcaggataa gcaaatgggt agtgaaaaga   3240
cattcatgag gacagctaaa acaataagta atgtaaaata cagcatagca aaactttaac   3300
ctccaaatca agcctctact tgaatccttt tctgagggat gaataaggca taggcatcag   3360
gggctgttgc caatgtgcat tagctgtttg cagcctcacc ttctttcatg gagtttaaga   3420
tatagtgtat tttcccaagg tttgaactag ctcttcattt ctttatgttt taaatgcact   3480
gacctcccac attccctttt tagtaaaata ttcagaaata atttaaatac atcattgcaa   3540
tgaaaataaa tgttttttat taggcagaat ccagatgctc aaggcccttc ataatatccc   3600
ccagtttagt agttggactt agggaacaaa ggaaccttta atagaaattg gacagcaaga   3660
aagcgagctt agtgatactt gtgggccagg gcattagcca caccagccac cactttctga   3720
taggcagcct gcactggtgg ggtgaattct ttgccaaagt gatgggccag cacacagacc   3780
agcacgttgc ccaggagctg tgggaggaag ataagaggta tgaacatgat tagcaaaagg   3840
gcctagcttg gactcagaat aatccagcct tatcccaacc ataaaataaa agcagaatgg   3900
tagctggatt gtagctgcta ttagcaatat gaaacctctt acatcagtta caatttatat   3960
gcagaaatat ttatatgcag aaatattgct attgccttaa cccagaaatt atcactgtta   4020
ttctttagaa tggtgcaaag aggcatgata cattgtatca ttattgccct gaaagaaaga   4080
gattagggaa agtattagaa ataagataaa caaaaaagta tattaaaaga agaaagcatt   4140
ttttaaaatt acaaatgcaa aattaccctg atttggtcaa tatgtgtacc ctgttacttc   4200
tccccttcct atgacatgaa cttaaccata gaaaagaagg ggaaagaaaa catcaagggt   4260
cccatagact caccctgaag ttctcaggat ccacgtgcag cttgtcacag tgcagctcac   4320
tcagctgggc aaaggtgccc ttgaggttgt ccaggtgagc caggccatca ctaaaggcac   4380
cgagcacttt cttgccatga gccttcacct tagggttgcc cataacagca tcaggagtgg   4440
acagatcccc aaaggactca aagaacctct gggtccaagg gtagaccacc agcagcctaa   4500
gggtgggaaa atagaccaat aggcagagag agtcagtgcc tatcagaaac ccaagagtct   4560
tctctgtctc cacatgccca gtttctattg gtctccttaa acctgtcttg taaccttgat   4620
accaacctgc ccagggcctc accaccaacg gcatccacgt tcaccttgtc ccacagggca   4680
gtaacggcag acttctcctc aggagtcagg tgcaccatgg tgtctgtttg aggttgctag   4740
tgaacacagt tgtgtcagaa gcaaatgtaa gcaatagatg gctctgccct gacttttatg   4800
cccagccctg gctcctgccc tccctgctcc tgggagtaga ttggccaacc ctagggtgtg   4860
```

```
gctccacagg gtgaggtcta agtgatgaca gccgtacctg tccttggctc ttctggcact   4920
ggcttaggag ttggacttca aaccctcagc cctccctcta agatatatct cttggcccca   4980
taccatcagt acaaattgct actaaaaaca tcctcctttg caagtgtatt tacccgacgc   5040
gtcggcgata agcttgatcc atcgatgttt agtcatgttt tctgggagct taggggctta   5100
ttttattttg ttttgttttc taatcaacag agatgggcaa acccattatt tttttcttta   5160
gacttgggat ggtgatagct gggcagcgtc agaaactgtg tgtggatata gataagagct   5220
caggactatg ctgagctgtg atgagggagg ggcctagcta aaggcagtga gagtcagaat   5280
gctcctgcta ttgccttcta cctgccttgg cacagttttt ctttactttt acctgactga   5340
tgaaacaatt aattgcttac ataaacatga gtgctctagt tataaattcc agtgtaaaaa   5400
acaccctggt ttcgatattc gttttagtca ggtggtcagc ttctcctttt ttttgccatc   5460
tgccctgtaa gcatcctgct ggggacccag ataggagtca tcactctagg ctgagaacat   5520
ctgggcacac accctaagcc tcagcatgac tcatcatgac tcagcattgc tgtgcttgag   5580
ccagaaggtt tgcttagaag gttacacaga accagaaggc gggggtgggg cactgacccc   5640
gacaggggcc tggccagaac tgctcatgct tggactatga gcctataacc catctgggcc   5700
ctgatagctg gtggccagcc ctgaccccac cccaccctcc ctggaacctc tgatagacac   5760
atctggcaca ccagctcgca aagtcaccgt gagggtcttg tgtttgctga gtcaaaattc   5820
cttgaaatcc aagtcctttt ttaaaataaa tatatcattt aaatgcataa ataagcaaac   5880
cctgctcggg aatgggaggg agagtctctg gagtccaccc cttctcggcc ctggctctgc   5940
agatagtgct atcaaagccc tgacagagcc ctgcccattg ctgggccttg gagtgagtca   6000
gcctagtaga gaggcagggc aagccatctc atagctgctg agtgggagag actatcaata   6060
acattctcac tctttcatca gtaatcactc aggttattct gtgaccaaca gactgtggga   6120
aaaatcagag aaggaggcat cctcatgctt actagcctaa ggcctactcg accacgaggg   6180
aattccgata atcaacctct ggattacaaa atttgtgaaa gattgactgg tattcttaac   6240
tatgttgctc cttttacgct atgtggatac gctgctttaa tgcctttgta tcatgctatt   6300
gcttcccgta tggctttcat tttctcctcc ttgtataaat cctggttgct gtctctttat   6360
gaggagttgt ggcccgttgt caggcaacgt ggcgtggtgt gcactgtgtt tgctgacgca   6420
acccccactg gttggggcat tgccaccacc tgtcagctcc tttccgggac tttcgctttc   6480
cccctcccta ttgccacggc ggaactcatc gccgcctgcc ttgcccgctg ctggacaggg   6540
gctcggctgt tgggcactga caattccgtg gtgttgtcgg ggaaatcatc gtcctttcct   6600
tggctgctcg cctgtgttgc cacctggatt ctgcgcggga cgtccttctg ctacgtccct   6660
tcggccctca atccagcgga ccttccttcc cgcggcctgc tgccggctct gcggcctctt   6720
ccgcgtcttc gccttcgccc tcagacgagt cggatctccc tttgggccgc ctccccgcat   6780
cgataccgtc gacctcgaga cctagaaaaa catggccaat tcgagctcgg tacctttaag   6840
accaatgact tacaaggcag ctgtagatct tagccacttt ttaaaagaaa aggggggact   6900
ggaagggcta attcactccc aacgaagaca agatcccagg gatgtacgtc cctaacccgc   6960
tagggggcag cacccaggcc tgcactgccg cctgccggca ggggtccagt cctgcttttt   7020
gcttgtactg ggtctctctg gttagaccag atctgagcct gggagctctc tggctaacta   7080
gggaacccac tgcttaagcc tcaataaagc ttgccttgag tgcttcaagt agtgtgtgcc   7140
cgtctgttgt gtgactctgg taactagaga tccctcagac ccttttagtc agtgtggaaa   7200
atctctagca gtagtagttc atgtcatctt attattcagt atttataact tgcaaagaaa   7260
```

```
tgaatatcag agagtgagag gaacttgttt attgcagctt ataatggtta caaataaagc   7320
aatagcatca caaatttcac aaataaagca tttttttcac tgcattctag ttgtggtttg   7380
tccaaactca tcaatgtatc ttatcatgtc tggctctagc tatcccgccc ctaactccgc   7440
ccatcccgcc cctaactccg cccagttccg cccattctcc gccccatggc tgactaattt   7500
ttttatttta tgcagaggcc gaggccgcct cggcctctga gctattccag aagtagtgag   7560
gaggcttttt tggaggccta ggcttttgcg tcgagacgta cccaattcgc cctatagtga   7620
gtcgtattac gcgcgctcac tggccgtcgt tttacaacgt cgtgactggg aaaaccctgg   7680
cgttacccaa cttaatcgcc ttgcagcaca tccccctttc gccagctggc gtaatagcga   7740
agaggcccgc accgatcgcc cttcccaaca gttgcgcagc ctgaatggcg aatggcgcga   7800
cgcgccctgt agcggcgcat taagcgcggc gggtgtggtg gttacgcgca gcgtgaccgc   7860
tacacttgcc agcgccctag cgcccgctcc tttcgctttc ttcccttcct ttctcgccac   7920
gttcgccggc tttccccgtc aagctctaaa tcgggggctc cctttagggt tccgatttag   7980
tgctttacgg cacctcgacc ccaaaaaact tgattagggt gatggttcac gtagtgggcc   8040
atcgccctga tagacggttt ttcgcccttt gacgttggag tccacgttct ttaatagtgg   8100
actcttgttc caaactggaa caacactcaa ccctatctcg gtctattctt ttgatttata   8160
agggattttg ccgatttcgg cctattggtt aaaaaatgag ctgatttaac aaaaatttaa   8220
cgcgaatttt aacaaaatat taacgtttac aatttcccag gtggcacttt tcggggaaat   8280
gtgcgcggaa cccctatttg tttatttttc taaatacatt caaatatgta tccgctcatg   8340
agacaataac cctgataaat gcttcaataa tattgaaaaa ggaagagtat gagtattcaa   8400
catttccgtg tcgcccttat tccctttttt gcggcatttt gccttcctgt ttttgctcac   8460
ccagaaacgc tggtgaaagt aaaagatgct gaagatcagt tgggtgcacg agtgggttac   8520
atcgaactgg atctcaacag cggtaagatc cttgagagtt ttcgccccga agaacgtttt   8580
ccaatgatga gcacttttaa agttctgcta tgtggcgcgg tattatcccg tattgacgcc   8640
gggcaagagc aactcggtcg ccgcatacac tattctcaga atgacttggt tgagtactca   8700
ccagtcacag aaaagcatct tacggatggc atgacagtaa gagaattatg cagtgctgcc   8760
ataaccatga gtgataacac tgcggccaac ttacttctga caacgatcgg aggaccgaag   8820
gagctaaccg cttttttgca caacatgggg gatcatgtaa ctcgccttga tcgttgggaa   8880
ccggagctga atgaagccat accaaacgac gagcgtgaca ccacgatgcc tgtagcaatg   8940
gcaacaacgt tgcgcaaact attaactggc gaactactta ctctagcttc ccggcaacaa   9000
ttaatagact ggatggaggc ggataaagtt gcaggaccac ttctgcgctc ggcccttccg   9060
gctggctggt ttattgctga taaatctgga gccggtgagc gtgggtctcg cggtatcatt   9120
gcagcactgg ggccagatgg taagccctcc cgtatcgtag ttatctacac gacggggagt   9180
caggcaacta tggatgaacg aaatagacag atcgctgaga taggtgcctc actgattaag   9240
cattggtaac tgtcagacca agtttactca tatatacttt agattgattt aaaacttcat   9300
ttttaattta aaaggatcta ggtgaagatc ctttttgata atctcatgac caaaatccct   9360
taacgtgagt tttcgttcca ctgagcgtca gaccccgtag aaaagatcaa aggatcttct   9420
tgagatcctt tttttctgcg cgtaatctgc tgcttgcaaa caaaaaaacc accgctacca   9480
gcggtggttt gtttgccgga tcaagagcta ccaactcttt ttccgaaggt aactggcttc   9540
agcagagcgc agataccaaa tactgtcctt ctagtgtagc cgtagttagg ccaccacttc   9600
```

```
aagaactctg tagcaccgcc tacatacctc gctctgctaa tcctgttacc agtggctgct   9660

gccagtggcg ataagtcgtg tcttaccggg ttggactcaa gacgatagtt accggataag   9720

gcgcagcggt cgggctgaac ggggggttcg tgcacacagc ccagcttgga gcgaacgacc   9780

tacaccgaac tgagatacct acagcgtgag ctatgagaaa gcgccacgct tcccgaaggg   9840

agaaaggcgg acaggtatcc ggtaagcggc agggtcggaa caggagagcg cacgagggag   9900

cttccagggg gaaacgcctg gtatctttat agtcctgtcg ggtttcgcca cctctgactt   9960

gagcgtcgat ttttgtgatg ctcgtcaggg gggcggagcc tatggaaaaa cgccagcaac  10020

gcggccattt ttacggttcc tggccttttg ctggcctttt gctcacatgt tctttcctgc  10080

gttatcccct gattctgtgg ataaccgtat taccgccttt gagtgagctg ataccgctcg  10140

ccgcagccga acgaccgagc gcagcgagtc agtgagcgag gaagcggaag agcgcccaat  10200

acgcaaaccg cctctccccg cgcgttggcc gattcattaa tgcagctggc acgacaggtt  10260

tcccgactgg aaagcgggca gtga                                         10284
```

```
<210> SEQ ID NO 31
<211> LENGTH: 230
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 31

gtttagtcat gttttctggg agcttagggg cttattttat tttgttttgt tttctaatca     60

acagagatgg gcaaacccat tattttttc tttagacttg ggatggtgat agctgggcag    120

cgtcagaaac tgtgtgtgga tatagataag agctcaggac tatgctgagc tgtgatgagg    180

gaggggccta gctaaaggca gtgagagtca gaatgctcct gctattgcct               230
```

```
<210> SEQ ID NO 32
<211> LENGTH: 124
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 32

tctacctgcc ttggcacagt ttttctttac ttttacctga ctgatgaaac aattaattgc     60

ttacataaac atgagtgctc tagttataaa ttccagtgta aaaaacaccc tggtttcgat    120

attc                                                                 124
```

```
<210> SEQ ID NO 33
<211> LENGTH: 259
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 33

gttttagtca ggtggtcagc ttctcctttt ttttgccatc tgccctgtaa gcatcctgct     60

ggggacccag ataggagtca tcactctagg ctgagaacat ctgggcacac accctaagcc    120

tcagcatgac tcatcatgac tcagcattgc tgtgcttgag ccagaaggtt tgcttagaag    180

gttacacaga accagaaggc gggggtgggg cactgacccc gacaggggcc tggccagaac    240
```

tgctcatgct tggactatg 259

<210> SEQ ID NO 34
<211> LENGTH: 159
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 34
agcctataac ccatctgggc cctgatagct ggtggccagc cctgacccca ccccaccctc 60
cctggaacct ctgatagaca catctggcac accagctcgc aaagtcaccg tgagggtctt 120
gtgtttgctg agtcaaaatt ccttgaaatc caagtcctt 159

<210> SEQ ID NO 35
<211> LENGTH: 211
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 35
ttttaaaata aatatatcat ttaaatgcat aaataagcaa accctgctcg ggaatgggag 60
ggagagtctc tggagtccac cccttctcgg ccctggctct gcagatagtg ctatcaaagc 120
cctgacagag ccctgcccat tgctgggcct tggagtgagt cagcctagta gagaggcagg 180
gcaagccatc tcatagctgc tgagtgggag a 211

<210> SEQ ID NO 36
<211> LENGTH: 111
<212> TYPE: DNA
<213> ORGANISM: Artificial
<220> FEATURE:
<223> OTHER INFORMATION: Artificial a human beta-globin locus control region (LCR) reduced length hypersensitive site (HS) sequences

<400> SEQUENCE: 36
gactatcaat aacattctca ctctttcatc agtaatcact caggttattc tgtgaccaac 60
agactgtggg aaaaatcaga gaaggaggca tcctcatgct tactagccta a 111

<210> SEQ ID NO 37
<211> LENGTH: 10041
<212> TYPE: DNA
<213> ORGANISM: Artificial
<220> FEATURE:
<223> OTHER INFORMATION: Lentiviral vector

<400> SEQUENCE: 37
gcgcaacgca attaatgtga gttagctcac tcattaggca ccccaggctt tacactttat 60
gcttccggct cgtatgttgt gtggaattgt gagcggataa caatttcaca caggaaacag 120
ctatgaccat gattacgcca agcgcgcaat taaccctcac taaagggaac aaaagctgga 180
gctgcaagct tggccattgc atacgttgta tccatatcat aatatgtaca tttatattgg 240
ctcatgtcca acattaccgc catgttgaca ttgattattg actagttatt aatagtaatc 300
aattacgggg tcattagttc atagcccata tatggagttc cgcgttacat aacttacggt 360
aaatggcccg cctggctgac cgcccaacga cccccgccca ttgacgtcaa taatgacgta 420
tgttcccata gtaacgccaa tagggacttt ccattgacgt caatgggtgg agtatttacg 480

```
gtaaactgcc cacttggcag tacatcaagt gtatcatatg ccaagtacgc cccctattga    540
cgtcaatgac ggtaaatggc ccgcctggca ttatgcccag tacatgacct tatgggactt    600
tcctacttgg cagtacatct acgtattagt catcgctatt accatggtga tgcggttttg    660
gcagtacatc aatgggcgtg gatagcggtt tgactcacgg ggatttccaa gtctccaccc    720
cattgacgtc aatgggagtt tgttttggca ccaaaatcaa cgggactttc caaaatgtcg    780
taacaactcc gccccattga cgcaaatggg cggtaggcgt gtacggtggg aggtctatat    840
aagcagagct cgtttagtga accggggtct ctctggttag accagatctg agcctgggag    900
ctctctggct aactagggaa cccactgctt aagcctcaat aaagcttgcc ttgagtgctt    960
caagtagtgt gtgcccgtct gttgtgtgac tctggtaact agagatccct cagacccttt   1020
tagtcagtgt ggaaaatctc tagcagtggc gcccgaacag ggacttgaaa gcgaaaggga   1080
aaccagagga gctctctcga cgcaggactc ggcttgctga agcgcgcacg gcaagaggcg   1140
aggggcggcg actggtgagt acgccaaaaa ttttgactag cggaggctag aaggagagag   1200
atgggtgcga gagcgtcagt attaagcggg ggagaattag atcgcgatgg gaaaaaattc   1260
ggttaaggcc agggggaaag aaaaaatata aattaaaaca tatagtatgg gcaagcaggg   1320
agctagaacg attcgcagtt aatcctggcc tgttagaaac atcagaaggc tgtagacaaa   1380
tactgggaca gctacaacca tcccttcaga caggatcaga agaacttaga tcattatata   1440
atacagtagc aaccctctat tgtgtgcatc aaaggataga gataaaagac accaaggaag   1500
ctttagacaa gatagaggaa gagcaaaaca aaagtaagac caccgcacag caagcggccg   1560
ctgatcttca gacctggagg aggagatatg agggacaatt ggagaagtga attatataaa   1620
tataaagtag taaaaattga accattagga gtagcaccca ccaaggcaaa gagaagagtg   1680
gtgcagagag aaaaaagagc agtgggaata ggagctttgt tccttgggtt cttgggagca   1740
gcaggaagca ctatgggcgc agcgtcaatg acgctgacgg tacaggccag acaattattg   1800
tctggtatag tgcagcagca gaacaatttg ctgagggcta ttgaggcgca acagcatctg   1860
ttgcaactca cagtctgggg catcaagcag ctccaggcaa gaatcctggc tgtggaaaga   1920
tacctaaagg atcaacagct cctggggatt tggggttgct ctggaaaact catttgcacc   1980
actgctgtgc cttggaatgc tagttggagt aataaatctc tggaacagat ttggaatcac   2040
acgacctgga tggagtggga cagagaaatt aacaattaca caagcttaat acactcctta   2100
attgaagaat cgcaaaacca gcaagaaaag aatgaacaag aattattgga attagataaa   2160
tgggcaagtt tgtggaattg gtttaacata acaaattggc tgtggtatat aaaattattc   2220
ataatgatag taggaggctt ggtaggttta agaatagttt ttgctgtact ttctatagtg   2280
aatagagtta ggcagggata ttcaccatta tcgtttcaga cccacctccc aaccccgagg   2340
ggacccgacg ggcccgaagg aatagaagaa gaaggtggag agagagacag agacagatcc   2400
attcgattag tgaacggatc tcgacggtat cgatctcgac acaaatggca gtattcatcc   2460
acaattttaa aagaaaaggg gggattgggg ggtacagtgc aggggaaaga atagtagaca   2520
taatagcaac agacatacaa actaaagaat tacaaaaaca aattacaaaa attcaaaatt   2580
ttcgggttta ttacagggac agcagagatc cagtttgggt cgaggatatc ggatcggaat   2640
tctctagatg atcaggatcc ctcgagccct tatcgatcac gagactagcc tcgactacta   2700
gtggagatcc cccgggctgc agagccagaa gcaccataag ggacatgata agggagccag   2760
cagacctctg atctcttcct gaatgctaat cttaaacatc ctgaggaaga atgggacttc   2820
catttggggt gggcctatga tagggtaata agacagtagt gaatatcaag ctacaaaaag   2880
```

```
ccccctttca aattcttctc agtcctaact tttcatacta agcccagtcc ttccaaagca   2940
gactgtgaaa gagtgatagt tccgggagac tagcactgca gattccgggt cactgtgagt   3000
gggggaggca gggaagaagg gctcacagga cagtcaaacc atgccccctg tttttccttc   3060
ttcaagtaga cctctataag acaacagaga caactaaggc tgagtggcca ggcgaggaga   3120
aaccatctcg ccgtaaaaca tggaaggaac acttcagggg aaaggtggta tctctaagca   3180
agagaactga gtggagtcaa ggctgagaga tgcaggataa gcaaatgggt agtgaaaaga   3240
cattcatgag gacagctaaa acaataagta atgtaaaata cagcatagca aaactttaac   3300
ctccaaatca agcctctact tgaatccttt tctgagggat gaataaggca taggcatcag   3360
gggctgttgc caatgtgcat tagctgtttg cagcctcacc ttctttcatg gagtttaaga   3420
tatagtgtat tttcccaagg tttgaactag ctcttcattt ctttatgttt taaatgcact   3480
gacctcccac attccctttt tagtaaaata ttcagaaata atttaaatac atcattgcaa   3540
tgaaaataaa tgttttttat taggcagaat ccagatgctc aaggcccttc ataatatccc   3600
ccagtttagt agttggactt agggaacaaa ggaaccttta atagaaattg gacagcaaga   3660
aagcgagctt agtgatactt gtgggccagg gcattagcca caccagccac cactttctga   3720
taggcagcct gcactggtgg ggtgaattct ttgccaaagt gatgggccag cacacagacc   3780
agcacgttgc ccaggagctg tgggaggaag ataagaggta tgaacatgat tagcaaaagg   3840
gcctagcttg gactcagaat aatccagcct tatcccaacc ataaaataaa agcagaatgg   3900
tagctggatt gtagctgcta ttagcaatat gaaacctctt acatcagtta caatttatat   3960
gcagaaatat ttatatgcag aaatattgct attgccttaa cccagaaatt atcactgtta   4020
ttctttagaa tggtgcaaag aggcatgata cattgtatca ttattgccct gaaagaaaga   4080
gattagggaa agtattagaa ataagataaa caaaaaagta tattaaaaga agaaagcatt   4140
ttttaaaatt acaaatgcaa aattaccctg atttggtcaa tatgtgtacc ctgttacttc   4200
tccccttcct atgacatgaa cttaaccata gaaaagaagg ggaaagaaaa catcaagggt   4260
cccatagact caccctgaag ttctcaggat ccacgtgcag cttgtcacag tgcagctcac   4320
tcagctgggc aaaggtgccc ttgaggttgt ccaggtgagc caggccatca ctaaaggcac   4380
cgagcacttt cttgccatga gccttcacct tagggttgcc cataacagca tcaggagtgg   4440
acagatcccc aaaggactca aagaacctct gggtccaagg gtagaccacc agcagcctaa   4500
gggtgggaaa atagaccaat aggcagagag agtcagtgcc tatcagaaac ccaagagtct   4560
tctctgtctc cacatgccca gtttctattg gtctccttaa acctgtcttg taaccttgat   4620
accaacctgc ccagggcctc accaccaacg gcatccacgt tcaccttgtc ccacagggca   4680
gtaacggcag acttctcctc aggagtcagg tgcaccatgg tgtctgtttg aggttgctag   4740
tgaacacagt tgtgtcagaa gcaaatgtaa gcaatagatg gctctgccct gacttttatg   4800
cccagccctg gctcctgccc tccctgctcc tgggagtaga ttggccaacc ctagggtgtg   4860
gctccacagg gtgaggtcta agtgatgaca gccgtacctg tccttggctc ttctggcact   4920
ggcttaggag ttggacttca aaccctcagc cctccctcta agatatatct cttggcccca   4980
taccatcagt acaaattgct actaaaaaca tcctcctttg caagtgtatt tacccgacgc   5040
gtcggcgata agcttgatcc atcgatatgt tttctgggag cttaggggct tattttattt   5100
tgttttgttt tctaatcaac agagatgggc aaacccatta ttttttttctt tagacttggg   5160
atggtgatag ctgggcagcg tcagaaactg tgtgtggata tagataagag ctcaggacta   5220
```

```
tgctgagctg tgatgaggga ggggcctagc taaaggcagt gagagtcaga atgctcctgc   5280
tattgccttt tttttgccat ctgccctgta agcatcctgc tggggaccca gataggagtc   5340
atcactctag gctgagaaca tctgggcaca caccctaagc ctcagcatga ctcatcatga   5400
ctcagcattg ctgtgcttga gccagaaggt ttgcttagaa ggttacacag aaccagaagg   5460
cgggggtggg gcactgaccc cgacaggggc ctggccagaa ctgctcatgc ttggactatg   5520
ccaccctccc tggaacctct gatagacaca tctggcacac cagctcgcaa agtcaccgtg   5580
agggtcttgt gtttgctgag tcaaaattcc ttgaaatcca agttaaatat atcatttaaa   5640
tgcataaata agcaaaccct gctcgggaat gggagggaga gtctctggag tccacccctt   5700
ctcggccctg gctctgcaga tagtgctatc aaagccctga cagagccctg cccattgctg   5760
ggccttggag tgagtcagcc tagtagagag gcagggcaag ccatctcata gctggactat   5820
caataacatt ctcactcttt catcagtaat cactcaggtt attctgtgac caacagactg   5880
tgggaaaaat cagagaagga ggcatcctca tgcttacggc ctactcgacc acgagggaat   5940
tccgataatc aacctctgga ttacaaaatt tgtgaaagat tgactggtat tcttaactat   6000
gttgctcctt ttacgctatg tggatacgct gctttaatgc ctttgtatca tgctattgct   6060
tcccgtatgg ctttcatttt ctcctccttg tataaatcct ggttgctgtc tctttatgag   6120
gagttgtggc ccgttgtcag gcaacgtggc gtggtgtgca ctgtgtttgc tgacgcaacc   6180
cccactggtt ggggcattgc caccacctgt cagctccttt ccgggacttt cgctttcccc   6240
ctccctattg ccacggcgga actcatcgcc gcctgccttg cccgctgctg gacaggggct   6300
cggctgttgg gcactgacaa ttccgtggtg ttgtcgggga aatcatcgtc ctttccttgg   6360
ctgctcgcct gtgttgccac ctggattctg cgcgggacgt ccttctgcta cgtcccttcg   6420
gccctcaatc cagcggacct tccttcccgc ggcctgctgc cggctctgcg gcctcttccg   6480
cgtcttcgcc ttcgccctca gacgagtcgg atctcccttt gggccgcctc cccgcatcga   6540
taccgtcgac ctcgagacct agaaaaacat ggccaattcg agctcggtac ctttaagacc   6600
aatgacttac aaggcagctg tagatcttag ccacttttta aaagaaaagg ggggactgga   6660
agggctaatt cactcccaac gaagacaaga tcccagggat gtacgtccct aacccgctag   6720
ggggcagcac ccaggcctgc actgccgcct gccggcaggg gtccagtcct gctttttgct   6780
tgtactgggt ctctctggtt agaccagatc tgagcctggg agctctctgg ctaactaggg   6840
aacccactgc ttaagcctca ataaagcttg ccttgagtgc ttcaagtagt gtgtgcccgt   6900
ctgttgtgtg actctggtaa ctagagatcc ctcagaccct tttagtcagt gtggaaaatc   6960
tctagcagta gtagttcatg tcatcttatt attcagtatt tataacttgc aaagaaatga   7020
atatcagaga gtgagaggaa cttgtttatt gcagcttata atggttacaa ataaagcaat   7080
agcatcacaa atttcacaaa taaagcattt ttttcactgc attctagttg tggtttgtcc   7140
aaactcatca atgtatctta tcatgtctgg ctctagctat cccgccccta actccgccca   7200
tcccgcccct aactccgccc agttccgccc attctccgcc ccatggctga ctaatttttt   7260
ttatttatgc agaggccgag gccgcctcgg cctctgagct attccagaag tagtgaggag   7320
gctttttttgg aggcctaggc ttttgcgtcg agacgtaccc aattcgccct atagtgagtc   7380
gtattacgcg cgctcactgg ccgtcgtttt acaacgtcgt gactgggaaa accctggcgt   7440
tacccaactt aatcgccttg cagcacatcc ccctttcgcc agctggcgta atagcgaaga   7500
ggcccgcacc gatcgccctt cccaacagtt gcgcagcctg aatggcgaat ggcgcgacgc   7560
gccctgtagc ggcgcattaa gcgcggcggg tgtggtggtt acgcgcagcg tgaccgctac   7620
```

```
acttgccagc gccctagcgc ccgctccttt cgctttcttc ccttcctttc tcgccacgtt   7680
cgccggcttt ccccgtcaag ctctaaatcg ggggctccct ttagggttcc gatttagtgc   7740
tttacggcac ctcgacccca aaaaacttga ttagggtgat ggttcacgta gtgggccatc   7800
gccctgatag acggtttttc gccctttgac gttggagtcc acgttcttta atagtggact   7860
cttgttccaa actggaacaa cactcaaccc tatctcggtc tattcttttg atttataagg   7920
gattttgccg atttcggcct attggttaaa aaatgagctg atttaacaaa aatttaacgc   7980
gaattttaac aaaatattaa cgtttacaat ttcccaggtg gcacttttcg gggaaatgtg   8040
cgcggaaccc ctatttgttt atttttctaa atacattcaa atatgtatcc gctcatgaga   8100
caataaccct gataaatgct tcaataatat tgaaaaagga agagtatgag tattcaacat   8160
ttccgtgtcg cccttattcc cttttttgcg gcattttgcc ttcctgtttt tgctcaccca   8220
gaaacgctgg tgaaagtaaa agatgctgaa gatcagttgg gtgcacgagt gggttacatc   8280
gaactggatc tcaacagcgg taagatcctt gagagttttc gccccgaaga acgttttcca   8340
atgatgagca cttttaaagt tctgctatgt ggcgcggtat tatcccgtat tgacgccggg   8400
caagagcaac tcggtcgccg catacactat tctcagaatg acttggttga gtactcacca   8460
gtcacagaaa agcatcttac ggatggcatg acagtaagag aattatgcag tgctgccata   8520
accatgagtg ataacactgc ggccaactta cttctgacaa cgatcggagg accgaaggag   8580
ctaaccgctt ttttgcacaa catgggggat catgtaactc gccttgatcg ttgggaaccg   8640
gagctgaatg aagccatacc aaacgacgag cgtgacacca cgatgcctgt agcaatggca   8700
acaacgttgc gcaaactatt aactggcgaa ctacttactc tagcttcccg gcaacaatta   8760
atagactgga tggaggcgga taaagttgca ggaccacttc tgcgctcggc ccttccggct   8820
ggctggttta ttgctgataa atctggagcc ggtgagcgtg ggtctcgcgg tatcattgca   8880
gcactggggc cagatggtaa gccctcccgt atcgtagtta tctacacgac ggggagtcag   8940
gcaactatgg atgaacgaaa tagacagatc gctgagatag gtgcctcact gattaagcat   9000
tggtaactgt cagaccaagt ttactcatat atactttaga ttgatttaaa acttcatttt   9060
taatttaaaa ggatctaggt gaagatcctt tttgataatc tcatgaccaa aatcccttaa   9120
cgtgagtttt cgttccactg agcgtcagac cccgtagaaa agatcaaagg atcttcttga   9180
gatccttttt ttctgcgcgt aatctgctgc ttgcaaacaa aaaaaccacc gctaccagcg   9240
gtggtttgtt tgccggatca agagctacca actctttttc cgaaggtaac tggcttcagc   9300
agagcgcaga taccaaatac tgtccttcta gtgtagccgt agttaggcca ccacttcaag   9360
aactctgtag caccgcctac atacctcgct ctgctaatcc tgttaccagt ggctgctgcc   9420
agtggcgata agtcgtgtct taccgggttg gactcaagac gatagttacc ggataaggcg   9480
cagcggtcgg gctgaacggg gggttcgtgc acacagccca gcttggagcg aacgacctac   9540
accgaactga gatacctaca gcgtgagcta tgagaaagcg ccacgcttcc cgaagggaga   9600
aaggcggaca ggtatccggt aagcggcagg gtcggaacag gagagcgcac gagggagctt   9660
ccagggggaa acgcctggta tctttatagt cctgtcgggt ttcgccacct ctgacttgag   9720
cgtcgatttt tgtgatgctc gtcagggggg cggagcctat ggaaaaacgc cagcaacgcg   9780
gccattttta cggttcctgg ccttttgctg gccttttgct cacatgttct ttcctgcgtt   9840
atcccctgat tctgtggata accgtattac cgcctttgag tgagctgata ccgctcgccg   9900
cagccgaacg accgagcgca gcgagtcagt gagcgaggaa gcggaagagc gcccaatacg   9960
```

```
caaaccgcct ctccccgcgc gttggccgat tcattaatgc agctggcacg acaggtttcc  10020

cgactggaaa gcgggcagtg a                                            10041


<210> SEQ ID NO 38
<211> LENGTH: 219
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 38

atgttttctg ggagcttagg ggcttatttt attttgtttt gttttctaat caacagagat     60

gggcaaaccc attatttttt tctttagact tgggatggtg atagctgggc agcgtcagaa    120

actgtgtgtg gatatagata agagctcagg actatgctga gctgtgatga gggaggggcc    180

tagctaaagg cagtgagagt cagaatgctc ctgctattg                           219


<210> SEQ ID NO 39
<211> LENGTH: 235
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 39

cctttttttt gccatctgcc ctgtaagcat cctgctgggg acccagatag gagtcatcac     60

tctaggctga gaacatctgg gcacacaccc taagcctcag catgactcat catgactcag    120

cattgctgtg cttgagccag aaggtttgct tagaaggtta cacagaacca gaaggcgggg    180

gtggggcact gaccccgaca ggggcctggc cagaactgct catgcttgga ctatg         235


<210> SEQ ID NO 40
<211> LENGTH: 102
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 40

ccaccctccc tggaacctct gatagacaca tctggcacac cagctcgcaa agtcaccgtg     60

agggtcttgt gtttgctgag tcaaaattcc ttgaaatcca ag                       102


<210> SEQ ID NO 41
<211> LENGTH: 192
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 41

ttaaatatat catttaaatg cataaataag caaaccctgc tcgggaatgg gagggagagt     60

ctctggagtc cacccccttct cggccctggc tctgcagata gtgctatcaa agccctgaca   120

gagccctgcc cattgctggg ccttggagtg agtcagccta gtagagaggc agggcaagcc    180

atctcatagc tg                                                        192


<210> SEQ ID NO 42
<211> LENGTH: 103
```

-continued

```
<212> TYPE: DNA
<213> ORGANISM: Artificial
<220> FEATURE:
<223> OTHER INFORMATION: Artificial a human beta-globin locus control
      region (LCR) reduced length hypersensitive site (HS) sequences

<400> SEQUENCE: 42

gactatcaat aacattctca ctctttcatc agtaatcact caggttattc tgtgaccaac     60

agactgtggg aaaaatcaga gaaggaggca tcctcatgct tac                      103
```